US009938537B2

(12) United States Patent
Johal et al.

(10) Patent No.: US 9,938,537 B2
(45) Date of Patent: Apr. 10, 2018

(54) COMPOSITIONS AND METHODS CONFERRING RESISTANCE OF MAIZE TO CORN ROOTWORM II

(71) Applicants: E. I. du Pont de Nemours and Company, Wilmington, DE (US); Pioneer Hi-Bred International, Inc., Johnston, IA (US); Purdue Research Foundation, West Lafayette, IN (US)

(72) Inventors: Gurmukh S. Johal, West Lafayette, IN (US); Bailin Li, Hockessin, DE (US); Dilbag S. Multani, Urbandale, IA (US)

(73) Assignees: Purdue Research Foundation, West Lafayette, IN (US); Pioneer Hi-Bred International, Inc., Johnston, IA (US); E.I. du Pont de Nemours and Company, Wilmington, DE (US)

( * ) Notice: Subject to any disclaimer, the term of this patent is extended or adjusted under 35 U.S.C. 154(b) by 1 day.

(21) Appl. No.: 14/430,017

(22) PCT Filed: Sep. 20, 2013

(86) PCT No.: PCT/US2013/061033
§ 371 (c)(1),
(2) Date: Mar. 20, 2015

(87) PCT Pub. No.: WO2014/047508
PCT Pub. Date: Mar. 27, 2014

(65) Prior Publication Data
US 2015/0240257 A1 Aug. 27, 2015

Related U.S. Application Data

(60) Provisional application No. 61/703,396, filed on Sep. 20, 2012, provisional application No. 61/703,414, filed on Sep. 20, 2012, provisional application No. 61/781,057, filed on Mar. 14, 2013, provisional application No. 61/781,124, filed on Mar. 14, 2013.

(51) Int. Cl.
*C12N 15/82* (2006.01)
*A01H 1/04* (2006.01)
*A01H 5/10* (2018.01)
*C07K 14/415* (2006.01)

(52) U.S. Cl.
CPC ........... *C12N 15/8286* (2013.01); *A01H 1/04* (2013.01); *A01H 5/10* (2013.01); *C07K 14/415* (2013.01)

(58) Field of Classification Search
None
See application file for complete search history.

(56) References Cited

U.S. PATENT DOCUMENTS

| 2006/0150283 A1* | 7/2006 | Alexandrov ......... C07K 14/415 800/288 |
| --- | --- | --- |
| 2008/0313777 A1 | 12/2008 | Dhugga et al. |
| 2010/0257621 A1 | 10/2010 | Ketkar et al. |
| 2011/0239329 A1 | 9/2011 | Dhugga et al. |
| 2012/0210462 A1 | 8/2012 | Bermudez et al. |

FOREIGN PATENT DOCUMENTS

WO WO 2011/044254 * 4/2011
WO WO-2012/058223 A1 5/2012

OTHER PUBLICATIONS

Barros-Rios et al (2011, Phytochem. 72:365-371).*
Purdue University, 2009, https://extension.entm.purdue.edu/fieldcropsipm/insects/corn-rootworms.php.*
International Search Report and Written Opinion issued by the International Searching Authority dated Dec. 23, 2013 for international application PCT/US2013/61033, filed Sep. 20, 2013, and published as WO 2014/047508 on Mar. 27, 2014 (Applicant—Pioneer Hi-Bred Int'l, Inc. // Inventor—Johal, et al.) (13 pages).
International Preliminary Report on Patentability dated Apr. 2, 2015 for international application PCT/US2013/61033, filed on Sep. 20, 2013, and published as WO 2014/047508 on Mar. 27, 2014 (Applicant—Pioneer Hi-Bred Int'l, Inc. // Inventor—Johal, et al.) (7 pages).
Dhillon B, Moose SP; and Johal GS. (2007). crw1—A novel maize mutant exceptionally susceptible to Western Corn Rootworm. Maize Genetics Conference Abstracts. Mar. 22-25, St. Charles, Illinois, available at http://www.maizegdb.org/data_center/reference?id=1079616 (2 pages).
Zhong, et al., "Transcriptional Activation of Secondary Wall Biosynthesis by Rice and Maize NAC and MYB Transcription Factors", Plant Cell Physiol. 52(10): 1856-1871 (2011).
UniProt G3M8D2 (2011) retrieved from http://www.uniprot.org/uniprot/G3M8D2 (5 pages).
UniProt Q9SNM6 (2000) retrieved from http://www.uniprot.org/uniprot/Q9SNM6 (7 pages).
UniProt C5YM23 (2009) retrieved from http://www.uniprot.org/uniprot/C5YM23 (6 pages).
UniProt Q5NKS7 (2005) retrieved from http://www.uniprot.org/uniprot/Q5NKS7 (6 pages).
UniProt I1MKD6 (2012) retrieved from http://www.uniprot.org/uniprot/I1MKD6.txt?version=3 (1 page).
UniProt I1KHQ4 (2012) retrieved from http://www.uniprot.org/uniprot/I1KHQ4 (6 pages).

(Continued)

*Primary Examiner* — Anne Kubelik
(74) *Attorney, Agent, or Firm* — Ballard Spahr LLP

(57) ABSTRACT

Methods and compositions for increasing a plant's resistance to an insect pest such as the corn rootworm are provided. Methods are provided for overexpression of Crw2, or variants thereof, in a host plant or plant cell to increase resistance to an insect pest in a plant such as maize. Methods are also provided for identifying variants of Crw2 that when incorporated into a plant via transgenic or traditional breeding means increase resistance to an insect pest in a plant such as maize. Also provided are methods for increasing resistance by overexpressing Crw1 and Crw2.

4 Claims, 30 Drawing Sheets

(56) References Cited

OTHER PUBLICATIONS

UniProt Q84WP6 (2006) retrieved from http://www.uniprot.org/uniprot/Q84WP6 (9 pages).
UniProt Q9LPI7 (2008) retrieved from http://www.uniprot.org/uniprot/Q9LPI7 (9 pages).
UniProt Q9M274 (2006) retrieved from http://www.uniprot.org/uniprot/Q9M274 (9 pages).
UniProt B4FPS5 (2008) retrieved from http://www.uniprot.org/uniprot/B4FPS5 (7 pages).
UniProt Q5NKQ3 (2005) retrieved from http://www.uniprot.org/uniprot/Q5NKQ3 (6 pages).
UniProt F6HU82 (2011) retrieved from http://www.uniprot.org/uniprot/F6HU82 (6 pages).
UniProt G4V2G0 (2011) retrieved from http://www.uniprot.org/uniprot/G4V2G0 (5 pages).
UniProt D9ZJ90 (2010) retrieved from http://www.uniprot.org/uniprot/D9ZJ90 (5 pages).
UniProt F2DV83 (2011) retrieved from http://www.uniprot.org/uniprot/F2DV83 (5 pages).
UniProt C4J6G0 (2009) retrieved at http://www.uniprot.org/uniprot/C4J6G0 (5 pages).
UniProt Q5Z8T7 (2004) retrieved from http://www.uniprot.org/uniprot/Q5Z8T7 (7 pages).
UniProt Q6Z0Z4 (2004) retrieved from http://www.uniprot.org/uniprot/Q6Z0Z4 (7 pages).
UniProt C5Z9B2 (2009) retrieved from http://www.uniprot.org/uniprot/C5Z9B2 (5 pages).
UniProt C5XTX5 (2009) retrieved from http://www.uniprot.org/uniprot/C5XTX5 (5 pages).
UniProt I1K5F9 (2012) retrieved from http://www.uniprot.org/uniprot/I1K5F9 (6 pages).
UniProt I1KQG2 (2012) retrieved from http://www.uniprot.org/uniprot/I1KQG2 (6 pages).
UniProt Q9LV23 (2000) retrieved from http://www.uniprot.org/uniprot/Q9LV23 (6 pages).
UniProt Q9LV22 (2000) retrieved from http://www.uniprot.org/uniprot/Q9LV22 (7 pages).
UniProt F2DBB4 (2011) retrieved from http://www.uniprot.org/uniprot/F2DBB4 (5 pages).
UniProt I1GWV1 (2012) retrieved from http://www.uniprot.org/uniprot/I1GWV1 (5 pages).
NCBI GI No. 356511269 retrieved from http://www.ncbi.nlm.nih.gov/protein/356511269#seguence_356511269 (2 pages).
Barros-Rios et al., "Cell wall composition as a maize defense mechanism against corn borers" (2011), Phytochem. 72:365-371.
Christensen et al., "Maize polyubiquitin genes: structure, thermal perturbation of expression and transcript splicing, and promoter activity following transfer to protoplasts by electroporation" (1992), Plant Mol. Biol. 18: 675-689.
Guo et al., "Protein Tolerance to random amino acid change" (2004), Proc. Natl. Acad. Sci. USA 101: 9205-9210.
Kjaersgaard et al., "Senescence-associated Barley NAC (NAM, ATAF 1 ,2, CUC) Transcription Factor Interacts with Radical-induced Cell Death 1 through a Disordered Regulatory Domain" (2011), J. Bioi. Chem 286:35418-35429.
Weiner et al, "NAC transcription factors: from structure to function in stress-associated networks" Plant Transcription Factors, (2016) Chapter 13; 199-212.
Non Final Rejection was dated Feb. 14, 2017 by the USPTO for U.S. Appl. No. 14/430,002, filed Mar. 20, 2015 and published as US 2015-0275228 A1 dated Oct. 1, 2015 (Applicant—Pioneer Hi-Bred International Inc.) (16 pages).
MBS Genetics, LLC. 2011 Genetic Handbook (136 pages).
Ooka et al., Comprehensive Analysis of NAC Family Genes in Oryza sativa and Arabidopsis thaliana. DNA Res. 2003; 10:239-47.
Venkata et al., crw1—A Novel Maize Mutant Highly Susceptible to Foliar Damage by the Western Corn Rootworm Beetle. PLos One. 2013; 8(8):e71296 (11 pages).
Zukoff et al., Western Corn Rootworm Larval Movement in SmartStax Seed Blend Scenarios. J Econ Entomol. 2012; 105(4):1248-60.

* cited by examiner

FIG. 1A

```
                1.........11.........21.........31.........41.........51.........60
Crw2            ATGAAGCAGCCGAGGGCCGGAGGGCCGCAGGAGCCGGCGCCAGGTGGGCAACGCCGCCATGGTCGTC
crw2-Mutag      ATGAAGCAGCCGAGGGCCGGGGGCCGCAGGAGCCGGCGCCGGGTGGGCAACGCCGCCATGGTCGTC
                ***************     ***************************************

61........71.........81.........91........101........111.......120
Crw2            ACCATGGTCGTCTCCCCTCGCGTCCTCGGTCCTCACGTACATCAAGGCGGATACTGCTCCAACCCT
crw2-Mutag      ACCATGGTCGTCTCCCCTCGCGTCCTCGGTCCTCACGTACATCAAGGCGGATACTGCTCCAACCCT
                ***************************************************************

121.......131........141........151........161........171.......180
Crw2            TTCCCCAAGGCGGTGGCGGAGGTGGAGGTGGACGAGGACTACGAGGACTACGACACAGCACGGTACAAG
crw2-Mutag      TTCCCCAAGGCGGTGGCGGAGGTGGAGGTGGACGAGGACTACGAGGACTACGACACGGCACGGTACAAG
                ***************************************************        *******

181.......191........201........211........221........231.......240
Crw2            CTGACGGGCCCCGTGGGCGGAGGAGGACTTCGACCCGTCCGCCCCACTGCTACAACACC
crw2-Mutag      CTGACGGGCGGCCCCGTGGCCGAGGACGACTTCGACCACTTCGACCCACCCCCACTGCTACAACACC
                ***********    *********                                 ********

241.......251........261........271........281........291.......300
Crw2            AGCAAGCGGTCGGAGCGGTCGCCGCCGGGTGCCGCCGTGGGCGACATCCGGCGGTGGCGACGGCAACCACCACTCG
crw2-Mutag      AGCAAGCGGTCGGAGCGGTCGCCGCCGGGTGCCGCCGTGGGCGACATCCGGCGGTGGACGGTGGACGGCAACCACCACTCG
                ***************************************************       ******************
```

FIG. 1B

```
        301.....311.....321.....331.....341.....351.....360
Crw2       CGGATCTACATCAGCCCGCTGTCCCGCGAGTGGCGGGACCAAGCCGTACGCGGGCGGCAC
crw2-Mutag CGGATCTACATCAGCCCGCTGTCCCGCGAGTGGCGGGACCAAGCCGTACGCGGGCGGCAC
           ************************************************************

361.....371.....381.....391.....401.....411.....420
Crw2       GACGCCCGTGGCCATGGACGACGTGCGGAGTTCACGCTGGTCCCCTTCGGCGGCCCCAAC
crw2-Mutag GACGCCGGTGGCCATGGACGACGTGCGGAGTTCACGCTGGTCCCCTTCGGCGGCCCCAAC
           ************************************************************

421.....431.....441.....451.....461.....471.....480
Crw2       GACACGGCCGTGCCGGCGCTCTGCACGCGGCACCCCACTCCGTCCGGGCTTCCTCTTCTCC
crw2-Mutag GACACGGCCGTGCCGGCGCTCTGCACGCGGCACCCCACTCCGTCCGGGCTTCCTCTTCTCC
           ************************************************************

481.....491.....501.....511.....521.....531.....540
Crw2       AGCGGCGGGTTCGCGGGCAACCTGTACCACGACTACGCCGACGTGCGGTGCCGCTCTTC
crw2-Mutag AGCGGCGGGTTCGCGGGCAACCTGTACCACGACTACGCCGACGTGCGGTGCCGCTCTTC
           ************************************************************

541.....551.....561.....571.....581.....591.....600
Crw2       GCCAGCACCAACCACCACCTGGGCGGGGAGGTCCAGTTCCTGCTGGCCGACATCAAGGACTGG
crw2-Mutag GCCAGCACCAACCACCACCTGGGCGGGGAGGTCCAGTTCCTGCTGGCCGACATCAAGGACTGG
           ************************************************************
```

FIG. 1C

```
Crw2        601.......611.......621.......631.......641.......651.......660
            TGGGCCGACAAGTTCCGCCCGCTCTTCCGCCAGCTCTCCCGCTACGACGTCATCGACGTG
crw2-Mutag  TGGGCCGACAAGTTCCGCCCGCTCTTCCGCCAGCTCTCCCGCTACGACGTCATCGACGTG
            ************************************************************

Crw2        661.......671.......681.......691.......701.......711.......720
            AACAACGACCGCGAGGTGCACTGCTTCCGGATCATCATCGGCTCCACCTTCCACCGC
crw2-Mutag  AACAACGACCGCGAGGTGCACTGCTTCCGGATCATCATCGGCTCCACCTTCCACCGC
            ************************************************************

Crw2        721.......731.......741.......751.......761.......771.......780
            GCCATGGGCATCGACCCCCTCGACCTCGGCGGCGTCACGGTGGCCGACTTCAAGCGC
crw2-Mutag  GCCATGGGCATCGACCCCCTCGACCTCGGCGGCGTCACGGTGGCCGACTTCAAGCGC
            ************************************************************

Crw2        781.......791.......801.......811.......821.......831.......840
            CTGCTCCGGCCGGTTCCGGCGGTGGAGCGCGCGTCCGCCGTCGCGGGTCGGGGCGCCCGG
crw2-Mutag  CTGCTCCGGCCGGTTCCGGCGGTGGAGCGCGCGTCCGCCGTCGCGGGTCGGGGCGCCCGG
            ************************************************************

Crw2        841.......851.......861.......871.......881.......891.......900
            CGCCGGGACCGGCCCCGCCTTCCTCATCATCCGCGCAAGAGCTCCGCCGCTTCGTCAAC
crw2-Mutag  CGCCGGGACCGGCCCCGCCTTCCTCATCATCCGCGCAAGAGCTCCGCCGCTTCGTCAAC
            ************************************************************
```

FIG. 1D

```
crw2        901....... 911....... 921....... 931....... 941....... 951....... 960
crw2-Mutag  GAGGCGCGCCATGGGCGGGCCGGCGCGGCGGCCCGGTTCGAGTGCGGATCGCCGAGCCC
            GAGGCGCGCCATGGGCGGGCCGGCGCGGCGGCCCGGTTCGACGTGCGGATCGCCGAGCCC
            ************************************************************ crw2        961....... 971....... 981....... 991....... 1001...... 1011...... 1020
crw2-Mutag  GACAACCACACGGACATGCCCAACTTCGGCGAGGCTGGTGAACTTCGGCGACGTGATGATG
            GACAACCACACGGACATGCCCAACTTCGGCGAGGCTGGTGAACTTCGGCGACGTGATGATG
            ************************************************************ crw2        1021...... 1031...... 1041...... 1051...... 1061...... 1071...... 1080
crw2-Mutag  GGCGTGCACGGGCGCCGGGCTCACCAACATGGTGTTCCTGCCCAGCCGCGTGCTGCTGGTG
            GGCGTGCACGGGCGCCGGGCTCACCAACATGGTGTTCCTGCCCAGCCGCGTGCTGCTGGTG
            ************************************************************ crw2        1081...... 1091...... 1101...... 1111...... 1121...... 1131...... 1140
crw2-Mutag  CAGGTGGTTGCCGTTCGGCGGGCTGGAGTGGGCTCACCGGTCACCTTCAAGGACCCCGCA
            CAGGTGGTTGCCGTTCGGCGGGCTGGAGTGGGCTCACCGGTCACCTTCAAGGACCCCGCA
            ************************************************************ crw2        1141...... 1151...... 1161...... 1171...... 1181...... 1191...... 1200
crw2-Mutag  AGGGAC------------------------------------------------------
            AGGGACGAGATAATTGCCATTATGGACGAAGAGGGAAGGGATTCGACGAAATGGAGGCG
            ******
```

FIG. 1E

```
Crw2          1201........1211........1221........1231........1241........1251........1260
crw2-Mutag    ----------------------------------------------------------------

Crw2          1261........1271........1281........1291........1301........1311........1320
              TTGCCGTTGGCTTCTCTGTTTTTGGAGACGGCACGCGACAGCCAAACTCCAAAACGGATACG
crw2-Mutag    ------------------------------------------ATGACGTCACGTACATGGAGTACAACGT
                                                         ****************************

Crw2          1321........1331........1341........1351........1361........1371........1380
              AGACAGCTCTTGGGGCTGCCGTAAACAGGGACGTCACGTACATGGAGTACAACGTTCACCTGAAGCA
crw2-Mutag    GTCGCTGGAGGAGAGCTCGCTCAGGGACCCTCTACCCGGAGGACCACTTCTACCTGAAGCA
              ****************************************************

Crw2          1381........1391........1401........1411........1421........1431........1440
              GTCGCTGGAGGAGAGCTCGCTCAGGGACCCTCTACCCGGAGGACCACTTCTACCTGAAGCA
              CCCCTACGACGTGCACAAGAAGGGTGGACGGCCATCAAGACGGTGTACCTGGACAAGCA
crw2-Mutag    CCCCTACGACGTGCACAAGAAGGGTGGACGGCCATCAAGACGGTGTACCTGGACAAGCA
              ****************************************************

Crw2          1441........1451........1461........1471........1481........1491........1500
              GAACGTCAGGTCAGGCTCAACCTCACCAGGTTCACCAGGACGCTGGAGCAGGCGCGAGATCTCTT
crw2-Mutag    GAACGTCAGGTCAGGCTCAACCTCACCAGGTTCACCAGGACGCTGGAGCAGGCGCGAGATCTCTT
              ****************************************************
```

FIG. 1F

```
Crw2        1501......1511......1521......1531......1541......1551......1560
            GCCGACGCCATGATGACTGATGATGATGACCTCCCCCCTCTTTCCTTCCTGCTCTGCTGCAAGTTTCAT
crw2-Mutag  GCCGACGCCATGATGACTGATGATGATGACCTCCCCCCTCTTTCCTTCCTGCTCTGCTGCAAGTTTCAT
            *******************************************************************

Crw2        1561......1571......1581......1591......1601......1611......1620
            TCACTTCAGATCAGCTGCTCACTTCACGCCGGTGTCTCTCTTTTTTTTTCT
crw2-Mutag  TCACTTCAGATCAGCTGCTCACTTCACGCCGGTGTCTCTCTTTTTTTTTCT
            *******************************************************************

Crw2        1621......1631......1641......1651......1661......1671......1680
            GTTGTTGTTCTATACATATACTTGTTCCTCTCCCTTCCCTCTCCTCTCTCTAGTCTCT
crw2-Mutag  GTTGTTGTTCTATACATATACTTGTTCCTCTCCCTTCCCTCTCCTCTCTCTAGTCTCT
            *******************************************************************

Crw2        1681......1691......1701......1711......1721......1731......1740
            CCCTCTCCACTCTTGTGGTGGCAAGATTCATTTCTTTCATTGTTTTTGTTTTTGTTGTTG
crw2-Mutag  CCCTCTCCACTCTTGTGGTGGCAAGATTCATTTCTTTCATTGTTTTTGTTTTTGTTGTTG
            *******************************************************************

Crw2        1741......1751......1761......1771......1781......1791......1800
            TTGTTGAGGAAGGATAGGAACAAAAACAAGTATTGTCGTGTCCAAGGTTAATCTACACA
crw2-Mutag  TTGTTGAGGAAGGATAGGAACAAAAACAAGTATTGTCGTGTCCAAGGTTAATCTACACA
            *******************************************************************
```

FIG. 1G

```
                1801........1811........1821........1831........1841........1851........1860
Crw2            AACACACACTGTAAATGATTGATTGATTGCTGTCAGTAGAGGCGAACACAAGGAATAGGT
crw2-Mutag      AACACACACTGTAAATGATTGATTGATTGCTGTCAGTAGAGGCGAACACAAGGAATAGGT
                ************************************************************

1861......1870
Crw2            AAAAAAAAAA
crw2-Mutag      AAAAAAAAAA
                **********
```

FIG. 2A

```
                 1.........11.........21.........31.........41.........51.........60
Crw2         ATGAAGCCAGCCCAGGCCCCCCAGCAGCCCCCGGGTGGCCAACGCCCCCATGGTCGTC
Crw2-BMS     ATGAAGCAGCCGAGGCCGGGGGCGGCAGGAGCGGCGGTGGCGTGGCAACGCCGCCATGGTGGTC
             * * * * * * * * * * * * * * * * * * * * * * * * * * * * * * * * * * * * * * * * * * * * * * * * * * * * * * * * * * *

61.........71.........81.........91.........101........111........120
Crw2         ACCATGGTCGTCTCCCTCTGGGTCCTCACGTACATCAAGGCGATACTGCTCCAACCCT
Crw2-BMS     ACCATGGTCGTCTCCCTCTGCCTCACGTACATCAAGGCGGATACTGCTCCAACCCT
             * * * * * * * * * * * * * * * * * * * * * * * * * * * * * * * * * * * * * * * * * * * * * * * * * * * * * * * * *

FIG. 2B

```
              301.......311.......321.......331.......341.......351.......360
crw2          CGGATCTACATCAGCCCGCTGTCCCGGAGTGGGGGACTGGGCCAAGCCGTACGGCGCGGGCAC
crw2-EMS      CGGATCTACATCAGCCCGCTGTCCCGCGAGTGGGGCGACTGGGCCAAGCCGTACGGCGCGGGCAC
              ************************************************************

361.......371.......381.......391.......401.......411.......420
crw2          GACGCCCGTGGCCATGGACGACGTGCCGGAGTTCACGCTGCCCCCTTCGGCGGCCCCCAAC
crw2-EMS      GACGCCCGTGGCCATGGACGACGTGCCGGAGTTCACGCTGCCCCCTTCGGCGGCCCCCAAC
              ************************************************************

421.......431.......441.......451.......461.......471.......480
crw2          GACACGGCCGTGCCGCGCTGCTCTGCACGCGCACCCACTCCGTCCCGGGCTTCCTCTTCTCC
crw2-EMS      GACACGGCCGTGCCGCGCTGCTCTGCACGCGCACCCACTCCGTCCCGGGCTTCCTCTTCTCC
              ************************************************************

481.......491.......501.......511.......521.......531.......540
crw2          AGCGGCGGGTTCGCGGGCAACCTGTACCACGACTACCCGGACGTGCTGGTGCCGCTCTTC
crw2-EMS      AGCGGCGGGTTCGCGGGCAACCTGTACCACGACTACCCGGACGTGCTGGTGCCGCTCTTC
              ************************************************************

541.......551.......561.......571.......581.......591.......600
crw2          GCCAGCACCAACCACCTGGGCGGGGAGGTCCAGTTCCTGCTGGCCGACATCAAGGACTGG
crw2-EMS      GCCAGCACCAACCACCTGGGCGGGGAGGTCCAGTTCCTGCTGGCCGACATCAAGGACTGG
              ************************************************************
```

FIG. 2C

```
           601........611........621........631........641........651........660
Crw2       TGGGCCGACAAGTTCCGCCCGCTCTTCCGGCTCTCCCGCTACGACGTCATCGACGTG
crw2-EMS   TGGGCCGACAAGTTCCGCCCGCTCTTCCGGCTCTCCCGCTACGACGTCATCGACGTG
           ************************************************************

661........671........681........691........701........711........720
Crw2       AACAACGACCGGCGGAGGTGCACTGCTTCCCGCGGATCATCATCGGCTTCCACCTTCCACCGC
crw2-EMS   AACAACGACCGGCGGAGGTGCACTGCTTCCCGCGGATCATCATCGGCTTCCACCTTCCACCGC
           ************************************************************

721........731........741........751........761........771........780
Crw2       GCCATGGGCATCGACCCCTGCGCTCGGCCCGGCGTCACGGTGGCCGACTTCAAGCGC
crw2-EMS   GCCATGGGCATCGACCCCTGCGCTCGGCCCGGCGTCACGGTGGCCGACTTCAAGCGC
           ************************************************************

781........791........801........811........821........831........840
Crw2       CTGCTCCGCGCGGCCGTTCCGGCTGGAAGCGCGCCGTCGCGGTCGCGGAGGCGCCCCGG
crw2-EMS   CTGCTCCGCGCGGCCGTTCCGGCTGGAAGCGCGCCGTCGCGGTCGCGGAGGCGCCCCGG
           ************************************************************

841........851........861........871........881........891........900
Crw2       CGCCGGGACCGGCCCCGCCCTCCTCATCATCTCGCCGCAAGAGCTCGCGCCTTCGTCAAC
crw2-EMS   CGCCGGGACCGGCCCCGCCCTCCTCATCATCTCGTGCAAGAGCTCGCGCCTTCGTCAAC
           ************************************************************  ←
```

FIG. 2D

```
            901.......911.......921.......931.......941.......951.......960
Crw2        GAGGCGCGGCCATGGCGCGGCGGCGGCGGCCCGGTTCGACGTGCGGTGCGGATGCGGAGCCC
crw2-EMS    GAGGCGCGGCCATGGCGCGGCGGCGGCGGCCCGGTTCGACGTGCGGTGCGGATGCGGAGCCC
            ************************************************************

961.......971.......981.......991......1001......1011......1020
Crw2        GACAACCACACGGACATGCCCAACTTCGCGAGGCTGGTGAACTCGGCGGACGTGATGATG
crw2-EMS    GACAACCACACGGACATGCCCAACTTCGCGAGGCTGGTGAACTCGGCGGACGTGATGATG
            ************************************************************

1021......1031......1041......1051......1061......1071......1080
Crw2        GGCGTGCACGGCGCCGGGGCTCACCAACATGGTGTTCCTGCCCAGCCGGCCGTGCTGGTG
crw2-EMS    GGCGTGCACGGCGCCGGGGCTCACCAACATGGTGTTCCTGCCCAGCCGGCCGTGCTGGTG
            ************************************************************

1081......1091......1101......1111......1121......1131......1140
Crw2        CAGGTGGTGCCGTTCGGCGGGCTGGAGTGGCTCACCGCGTCACCCGCGTCAAGGACCCGCA
crw2-EMS    CAGGTGGTGCCGTTCGGCGGGCTGGAGTGGCTCACCGCGTCACCCGCGTCAAGGACCCGCA
            ************************************************************

1141......1151......1161......1171......1181......1191......1200
Crw2        AGGGACATGGACGTCACGTACAGTGAGTACAACGTGTCGCTGGAGGAGAGCTCGGCTCAGG
crw2-EMS    AGGGACATGGACGTCACGTACAGTGAGTACAACGTGTCGCTGGAGGAGAGCTCGGCTCAGG
            ************************************************************
```

FIG. 2E

```
Crw2      1201....:....1211....:....1221....:....1231....:....1241....:....1251....:....1260
          GACCTCTACCCGGAGGACCACTTCTACCTGAAGCACCCTACGACGTGCACAAGAAGGGG
crw2-EMS  GACCTCTACCCGGAGGACCACTTCTACCTGAAGCACCCTACGACGTGCACAAGAAGGGG
          ************************************************************

Crw2      1261....:....1271....:....1281....:....1291....:....1301....:....1311....:....1320
          TGGGACGGCCATCAAGAGACGGTGTACCTGGACAAGCAGAAGCGTCAGGCTCAACCTCACCAGG
crw2-EMS  TGGGACGGCCATCAAGACAAGGTGTACCTGGACAAGCAGAAGCGTCAGGCTCAACCTCACCAGG
          ************************************************************

Crw2      1321....:....1331....:....1341....:....1351....:....1361....:....1371....:....1380
          TTCACCAGGACGCTGGAGCAGGCGGAGATCTCTTGCCGACGGCCATGACTGATGATGACC
crw2-EMS  TTCACCAGGACGCTGGAGCAGGCGGAGATCTCTTGCCGACGGCCATGACTGATGATGACC
          ************************************************************

Crw2      1381....:....1391....:....1401....:....1411....:....1421....:....1431....:....1440
          TCCCCCTCTTTCCTCTGCTCTGCAGGTTTCATTCACTTCAGATCAGCTGCTCACCTC
crw2-EMS  TCCCCCTCTTTCCTCTGCTCTGCAGGTTTCATTCACTTCAGATCAGCTGCTCACCTC
          ************************************************************

Crw2      1441....:....1451....:....1461....:....1471....:....1481....:....1491....:....1500
          ACTTCACGCCGTGTCTCTCTCTCTTTTTTTTTTTTCTGTTGTTCTATACATATACTTGT
crw2-EMS  ACTTCACGCCGTGTCTCTCTCTCTTTTTTTTTTTTCTGTTGTTCTATACATATACTTGT
          ************************************************************
```

FIG. 2F

```
          1501........1511........1521........1531........1541........1551........1560
crw2      TTCCTCTTCTCCTTTCCTTTCCCCTCTCTCTAGTCTCCCTCTCCACTCTTGTGGTGGCAAG
crw2-EMS  TTCCTCTTCTCCTTTCCTTTCCCCTCTCTCTAGTCTCCCTCTCCACTCTTGTGGTGGCAAG
          ************************************************************

1561........1571........1581........1591........1601........1611........1620
crw2      ATTCATTTCTTTCATTGTTTTGTTTTTGTTTTTGTTGTTGTTGAGGAAGGATAGGAACAAAA
crw2-EMS  ATTCATTTCTTTCATTGTTTTGTTTTTGTTTTTGTTGTTGTTGAGGAAGGATAGGAACAAAA
          ************************************************************

1621........1631........1641........1651........1661........1671........1680
crw2      ACAAGGTATTGTCGTGTCCAAGGTTAAATCTACACAAACACACACTGTAAATGATTGATTG
crw2-EMS  ACAAGGTATTGTCGTGTCCAAGGTTAAATCTACACAAACACACACTGTAAATGATTGATTG
          ************************************************************

1681........1691........1701........1711.....17211725
crw2      ATTGCTGTCAGTAGAGAGGCGAACACAAGGAATAGGTAAAAAAAAAA
crw2-EMS  ATTGCTGTCAGTAGAGAGGCGAACACAAGGAATAGGTAAAAAAAAAA
          ***********************************************
```

FIG. 4D

```
      ..PYAR.....AM..VRE.............C..H.......FS.GG...N..H Consensus #1(SEQIDNO45)
      TKPYARRHDAVAMDDVREFTLKPFG------XXTAVPPICTRNHSVPAFLFSXGGFAGNLYH Majority(SEQIDNO46)
               190       200       210       220       230       240
               |         |         |         |         |         |
113   TKPYARRHDAVAMDDVREFTLVPFG---GPNDTAVPPICTRTHSVPGFLFSGGFAGNLYH   Zm(SEQIDNO2)
149   TKPYARYHDPVAMAHVREYTLKPLP---E---AAPAPACTRNHSVPGFLFSNGGFSGNLYH  Zm(SEQIDNO7)
148   TKPYARYHDPVAMAHVREYTLKALP---EPGAAAAPACTRNHSVPGFLFSGGFSGNLYH   Zm(SEQIDNO8)
119   TKPYARLHDAVAMDDVREFTLVPFG---GANHTAVPPICTRNHSVPAFLFSSGGFAGNLYH  Os(SEQIDNO9)
149   TKPYARYHDPVAMAVVREFTLKPVT---E---S-SPACTRNHSVPARYFSNGGFSGNLYH   Os(SEQIDNO10)
118   TKPYARLHDPVAMAHVREFTTVPFGPGSPNGTVVPPICTRNHSVPGFLFSSGGFAGNLYH   Sb(SEQIDNO11)
162   TKPYARYHDPVAMAHVREYTLKPLP------AAEAPACTRNHSVPGFLFSNGGFSGNLYH   Sb(SEQIDNO12)
116   LKPYARRDDVDAMIRVREWSVKAVN---VSQKAPQCTQYHNIPAVLFSTGGYAGNHFH     Gm(SEQIDNO13)
126   LKPYARRGDIDAMNRVREWSVKAVN---ASQKAPQCTQSHNITAVLFSTGGYSGNHFH     Gm(SEQIDNO14)
45    IRPYARKGDTVAMKRVREWTVKLEQNADQLENANFSRCVRNHSVPAMIFSLGGYSMNNFH   At(SEQIDNO15)
136   MRPYARKDQVPAMKRVREWTVKLVQ------NASLSRCVRNHSVPAILFSLGGFSLNNFH   At(SEQIDNO16)
118   TKPYARRHDAVAMDDVREFALIPFG---GGNDSAVPPICTRNHSVPGFLFSSGGFAGNLYH  Hv(SEQIDNO17)
119   TKPYARRHDAVAMDDVREFTLIPFDFESSNIVVPPICTRNHSVPAFLFSSGGFAGNLYH    Bd(SEQIDNO18)
118   TKPYARLHDAVAMDDVREYTLVPFG---GANDTAVPPICTRHSAPAFLFSNGGFAGNLYH   Pn(SEQIDNO20)
116   TKPYARRHDAVAMDDVREFTLVPFG---GANDTAVPPICTRNHSVPGFLFSGGFAGNLYH   En(SEQIDNO22)
126   LKPYARRDDVDAMIRVREWSVKAVN---VSQKAPQCTQYHNIPAVLFSTGGYAGNHFH     Gm(SEQIDNO23)
```

```
                          ..GVHGAG.TN..FLP.FLP.A...Q..P.GG....W....F..P......Y..Y.....E Consensus #1(SEQIDNO45)
                          MMGVHGAGLTNMVFLPSRAVLQVVPFGG---LEWTRVTFKDPAKDMDVNYMEYNVSLEE Majority(SEQIDNO46)

|         |         |         |         |         |
                         430       440       450       460       470       480

339  MMGVHGAGLTNMVFLPSRAVLQVVPFGG---LEWTRVTFKDPARDMDVTYMEYNVSLEE  Zm(SEQIDNO2)
           371  MMGVHGAGLTNMVFLPRGAVLQVVPFGG---LEWTGVTFKDPAADMEVSYMGYDVTLEE  Zm(SEQIDNO7)
           375  MMGVHGAGLTNMVFLPRGAVLQVVPFGG---LEWTGVTFKEPAADMEVSYMDYHVRLEE  Zm(SEQIDNO8)
           344  MMGVHGAGLTNMVFLPSRAVLQVVPFGG---LEWTRVTFKDPAKDMDVNYMEYNVSFDE  Os(SEQIDNO9)
           369  MMGVHGAGLTNMVFLPSRAVLQVVPFGG---LEWTTVTFKNPAKDMEVTYMDYNVQLEE  Os(SEQIDNO10)
           346  MMGVHGAGLTNMVFLPSRAVLQVVPFGG---LEWTRVTFKDPARDMDVTYMEYNVSLEE  Sb(SEQIDNO11)
           383  MMGVHGAGLTNMVFLPRGAVLQVVPFGG---LEWTSVTFKDPAADMEVNYMDYNVKLEE  Sb(SEQIDNO12)
           335  LLGVHGAGLTNILFLPENAVFVQVVPYGG VTLDWATNDFGNPSKDMNIKYLEYKISLEE  Gm(SEQIDNO13)
           345  LLGVHGAGLTNILFLPENAVFIQVVPYGGFTLDWATNDFGKPSKDMNLKYLEYKIGLKE  Gm(SEQIDNO14)
           271  MLGVHGAGLTNMVFLPENAVVIQVTPIGG---FEWAKTDFEKPSEGMNLRYLEYKIAVEE  At(SEQIDNO15)
           352  MLGVHGAMTNMVFLPDNAIVIQIIPIGG---FEWAKMDFEYPSKGMNLRYLEYKITAEE  At(SEQIDNO16)
           343  MMGVHGAGLTNMVFLPSRAVLQVVPFGG---LEWTSRVTFKDPAKDFDVTYMEYNVSLEE  Hv(SEQIDNO17)
           340  MMGVHGAGLTNMVFLPSRAVLQVVPFGG---LEWTSRVTFKDPAKDMDVNYMEYNVSLEE  Bd(SEQIDNO18)
           343  MMGVHGAGLTNMVFLPSRAVLQVVPFGG---LEWTSRVTFKDPAKDYDVNYMEYNVSLEE  Pn(SEQIDNO20)
           346  MMGVHGAGLTNILFLPENAVFVQVVPYGGVTLDWATNDFGNPSKDMNIKYLEYKISLEE  En(SEQIDNO22)
           345  LLGVHGAGLTNILFLPENAVFVQVVPYGGVTLDWATNDFGNPSKDMNIKYLEYKISLEE  Gm(SEQIDNO23)
```

FIG. 4J

Consensus #1(SEQIDNO45)
Majority(SEQIDNO46)

| | |
|---|---|
| 455 | Zm(SEQIDNO2) |
| 488 | Zm(SEQIDNO7) |
| 491 | Zm(SEQIDNO8) |
| 460 | Os(SEQIDNO9) |
| 485 | Os(SEQIDNO10) |
| 462 | Sb(SEQIDNO11) |
| 499 | Sb(SEQIDNO12) |
| 452 | Gm(SEQIDNO13) |
| 462 | Gm(SEQIDNO14) |
| 384 | At(SEQIDNO15) |
| 470 V | At(SEQIDNO16) |
| 461 SH | Hv(SEQIDNO17) |
| 455 | Bd(SEQIDNO18) |
| 459 | Pn(SEQIDNO20) |
| 462 | En(SEQIDNO22) |
| 462 | Gm(SEQIDNO23) |

FIG. 6 A and B

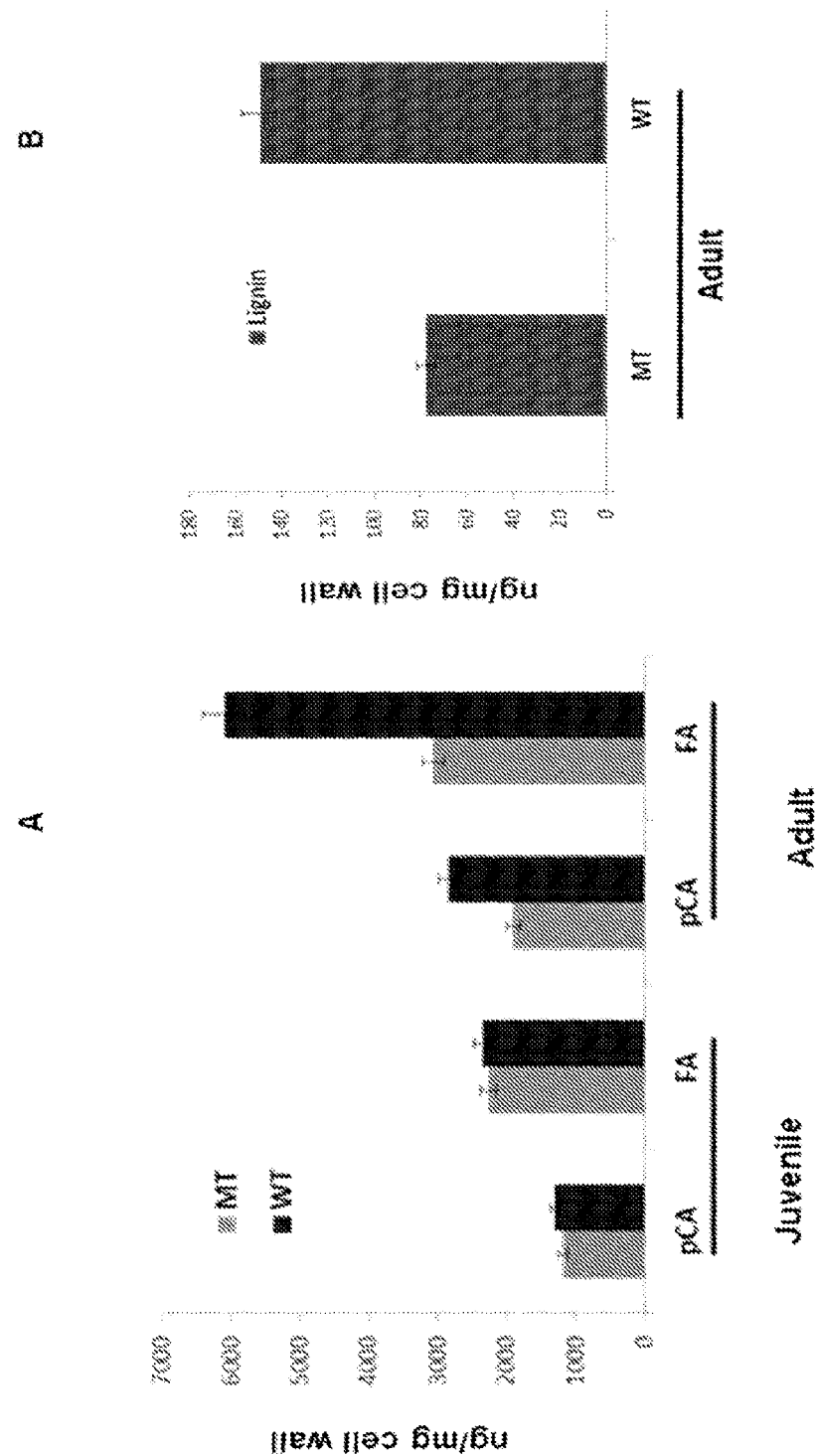
FIGS. 10A and B

US 9,938,537 B2

COMPOSITIONS AND METHODS CONFERRING RESISTANCE OF MAIZE TO CORN ROOTWORM II

CROSS REFERENCE TO RELATED APPLICATIONS

The application is a National Phase Under 35 U.S.C. § 371 of PCT/US2013/061033 filed in the Patent Cooperation Treaty U.S. Receiving Office on Sep. 20, 2013, which claims the benefit of U.S. Provisional Application No. 61/703,396, filed Sep. 20, 2012, U.S. Provisional Application No. 61/781,057, filed Mar. 14, 2013, U.S. Provisional Application No. 61/703,414, filed Sep. 20, 2012; and U.S. Provisional Application No. 61/781,124, filed Mar. 14, 2013; the entire contents of which are herein incorporated by reference.

REFERENCE TO SEQUENCE LISTING

The Sequence Listing submitted Jun. 14, 2017 as a text file named "36446_0196U1 Substitute Sequence Listing," created on May 15, 2017, and having a size of 157,648 bytes is hereby incorporated by referenced pursuant to 37 C.F.R. § 1.52(e)(5).

FIELD

The field relates to plant breeding and genetics and, in particular, relates to recombinant DNA constructs useful in maize plants for conferring resistance to corn rootworm.

BACKGROUND

The larval forms of three species of *Diabrotica* beetles, the Western corn rootworm (*Diabrotica virgifera virgifera* LeConte), the Northern corn rootworm (*Diabrotica barberi* Smith and *Diabrotica barberi* Lawrence), and the Southern corn rootworm (*Diabrotica undecimpunctata howardi* Barber), represent serious insect pests of corn in the Midwestern United States. Approximately 30 million acres (120,000 $km^2$) of corn (out of 80 million grown) are infested with corn rootworms, the larvae of which can cause losses estimated by the United States Department of Agriculture on the order of about $1 billion per year.

There are many different management practices aimed at the control of corn rootworms, including corn variety selection, early planting, insecticides, crop rotation, and the use of transgenic corn varieties; however, none on its own has proven to effectively manage the pest. An additional complication exists in that corn rootworm insects have shown a remarkable ability to evolve resistance to several control measures, including insecticides, cultural practices, and resistance genes that have been introduced into plants.

Thus, there is a constant need for new mechanisms of corn rootworm resistance in maize that can be incorporated into an integrated pest management strategy.

SUMMARY

Methods of increasing resistance to herbivory by an insect pest in a maize plant are provided in which polynucleotides encoding CRW2 are expressed in maize plants. In addition, methods of increasing resistance to herbivory by an insect pest in a maize plant are provided in which polynucleotides encoding CRW1 and CRW2 are expressed in maize plants.

Also provided are methods of identifying variants of ZmCrw2 (or ZmCRW2) that give maize plants increased resistance to herbivory by an insect pest and then further introducing the variants into the maize plants. The variants can be identified through gene shuffling experiments or can be naturally occurring allelic variants identified through linkage mapping or whole genome association analyses. Variants arising from gene shuffling can be transgenically introduced into maize plants to give them the increased resistance, while allelic variants identified using the methods presented herein can be incorporated into maize plants using molecular breeding.

In some embodiments, the insect pest is Coleopteran.

In other embodiments, the Coleopteran insect pest is of the genus *Diabrotica*. In still other embodiments, the insect pest is a corn rootworm, including without limitation, the Western corn rootworm (*Diabrotica virgifera virgifera* LeConte), the Northern corn rootworm (*Diabrotica barberi* Smith and *Diabrotica barberi* Lawrence), and/or the Southern corn rootworm (*Diabrotica undecimpunctata howardi* Barber).

In other embodiments, the Coleopteran insect pest is of the genus *Popiffia*, and the insect pest is the Japanese beetle.

In some embodiments, the insect pest is Lepidopteran. The Lepidopteran insect pest may be European corn borer (*Ostrinia* sp.), fall webworm (*Hyphantria cunea*), or cattail caterpillar (*Simyra insularis*).

Isolated polynucleotides or cDNAs, recombinant constructs containing said polynucleotides, and plants and plant cells containing said recombinant constructs are also provided.

BRIEF DESCRIPTION OF THE DRAWINGS AND SEQUENCE LISTING

The disclosure can be more fully understood from the following detailed description and the accompanying drawings and Sequence Listing which form a part of this application.

FIGS. 1A-1G shows the alignment between ZmCrw2 (SEQ ID NO:1) and the crw2-Mutag mutant allele (SEQ ID NO:3).

FIGS. 2A-2F shows the alignment between ZmCrw2 (SEQ ID NO:1) and the crw2-EMS mutant allele (SEQ ID NO:5).

FIGS. 4A-4J show an alignment of the ZmCrw2 protein (SEQ ID NO:2) and its homologs (SEQ ID NOs: 7, 8, 9, 10, 11, 12, 13, 14, 15, 16, 17, 18, 20, 22, and 23).

Figure 6:
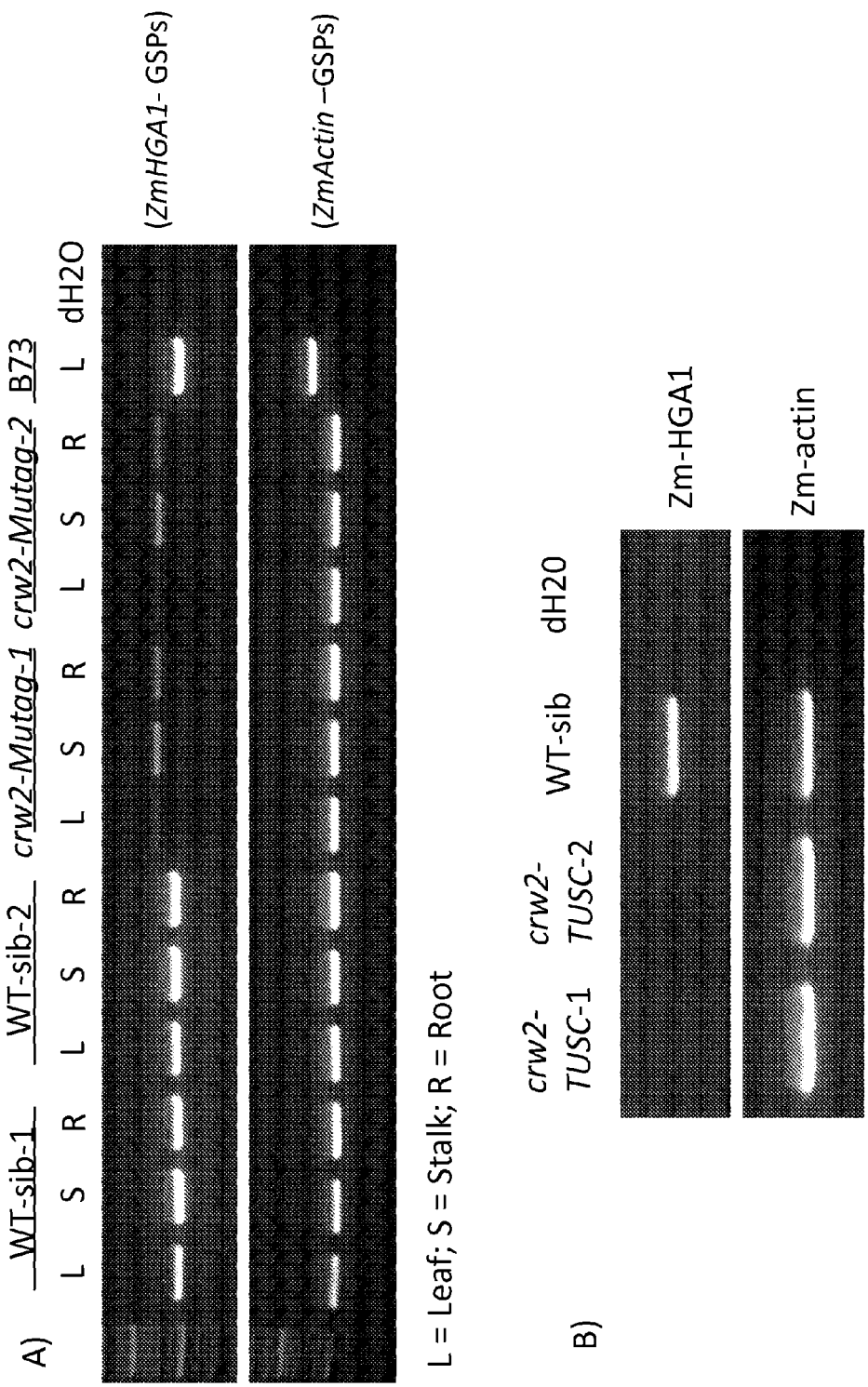

FIG. 6(A) shows gene expression of crw2-Mutag mutant allele in 10 day old seedlings. Total RNA samples were collected from leaf, stalk, and root tissues, and RT-PCR analysis was performed using gene specific primers. The crw2-Mutag mutant showed differential expression in three tissues and has a transcript that is 145 bp longer than in the WT-sibs. FIG. 6 (B) shows RT-PCR analysis of the crw2-TUSC mutant as compared to its WT-sibs. In this figure, "−1" and "−2" refer to two separate samples that were tested for each allele.

Figure 7:
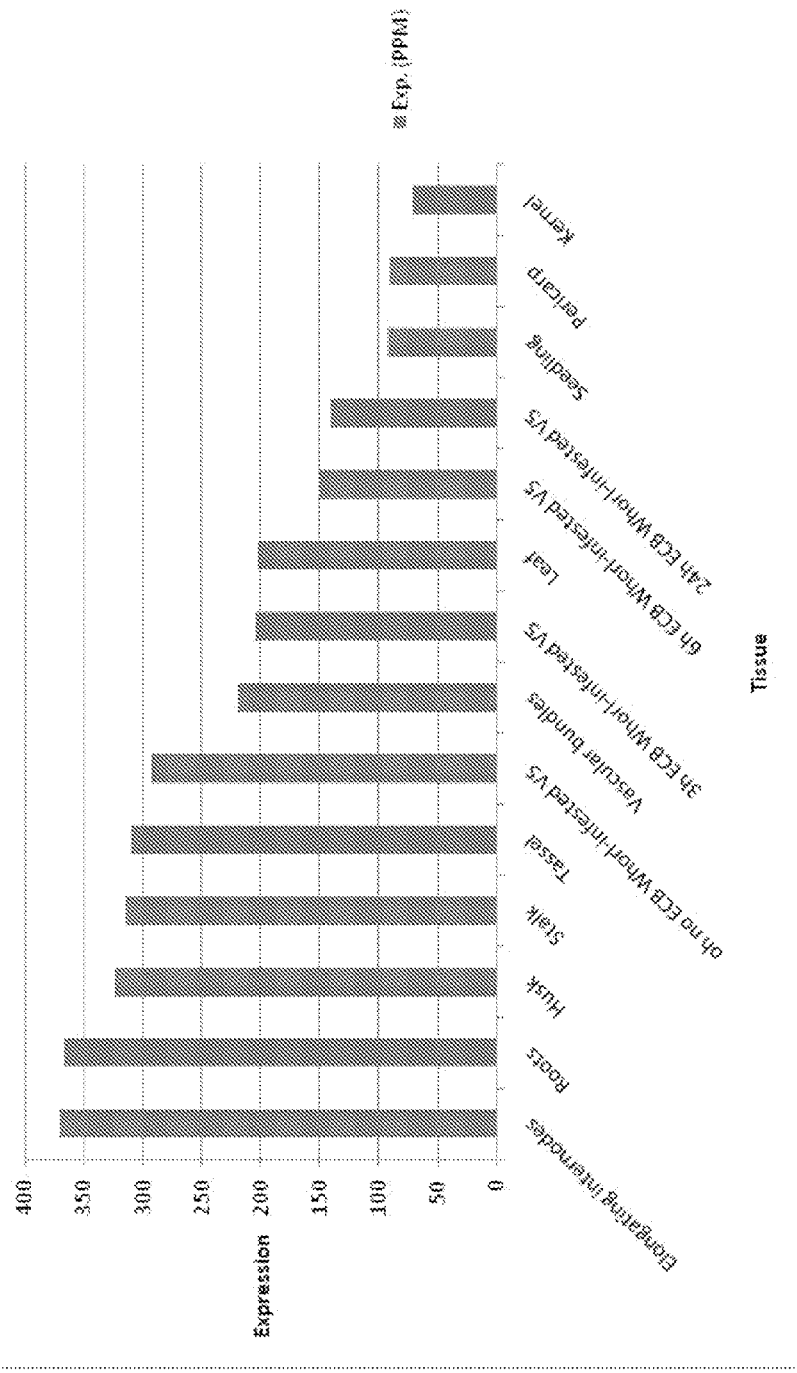

FIG. 7 shows expression of the ZmCrw2 gene in different plant tissues compiled from the Lynx database.

Figure 8:
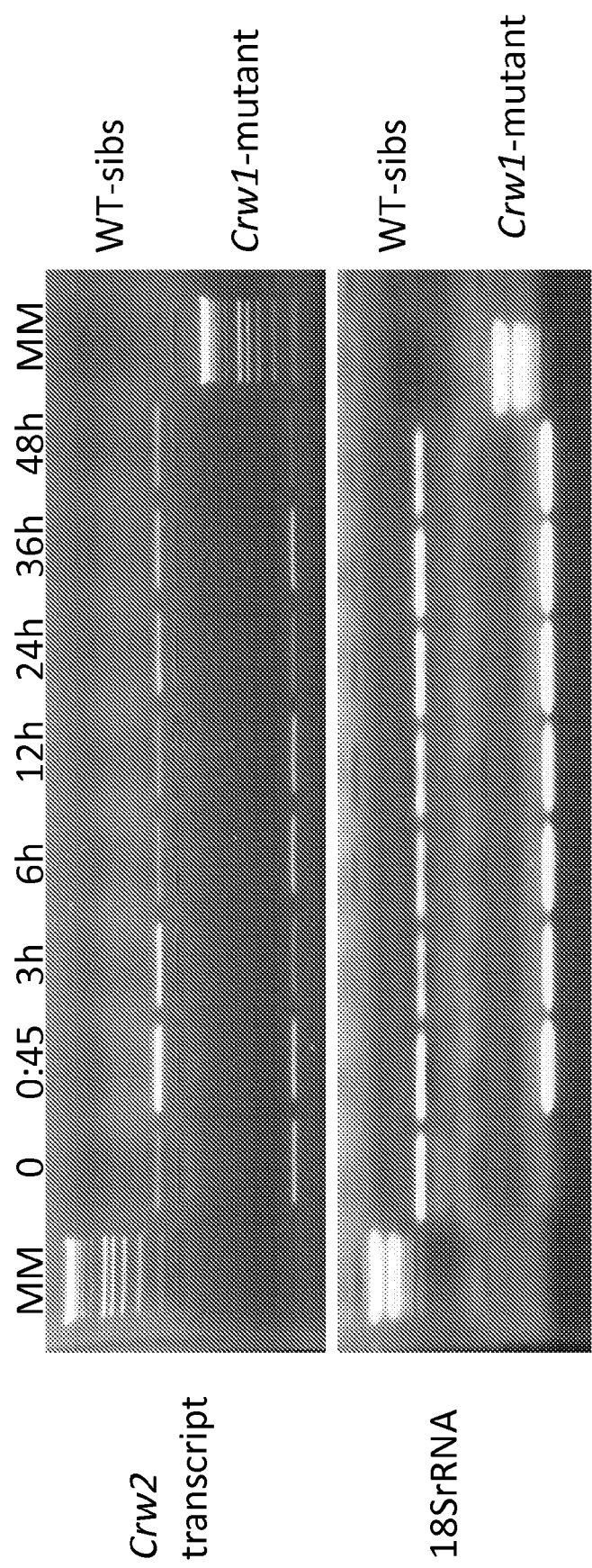

FIG. 8 shows Crw2 transcript levels in a Crw1 mutant in comparison to its WT at various time points after WCR beetle feeding. There is a rapid up-regulation in the levels of the Crw2 transcript in WT plants within 45 minutes of WCR feeding (upper panel). Such up-regulation is not observed in the Crw1 mutant upon WCR feeding (lower panel). The 18S rRNA control with the same loading scheme is represented in B.

Figure 9:
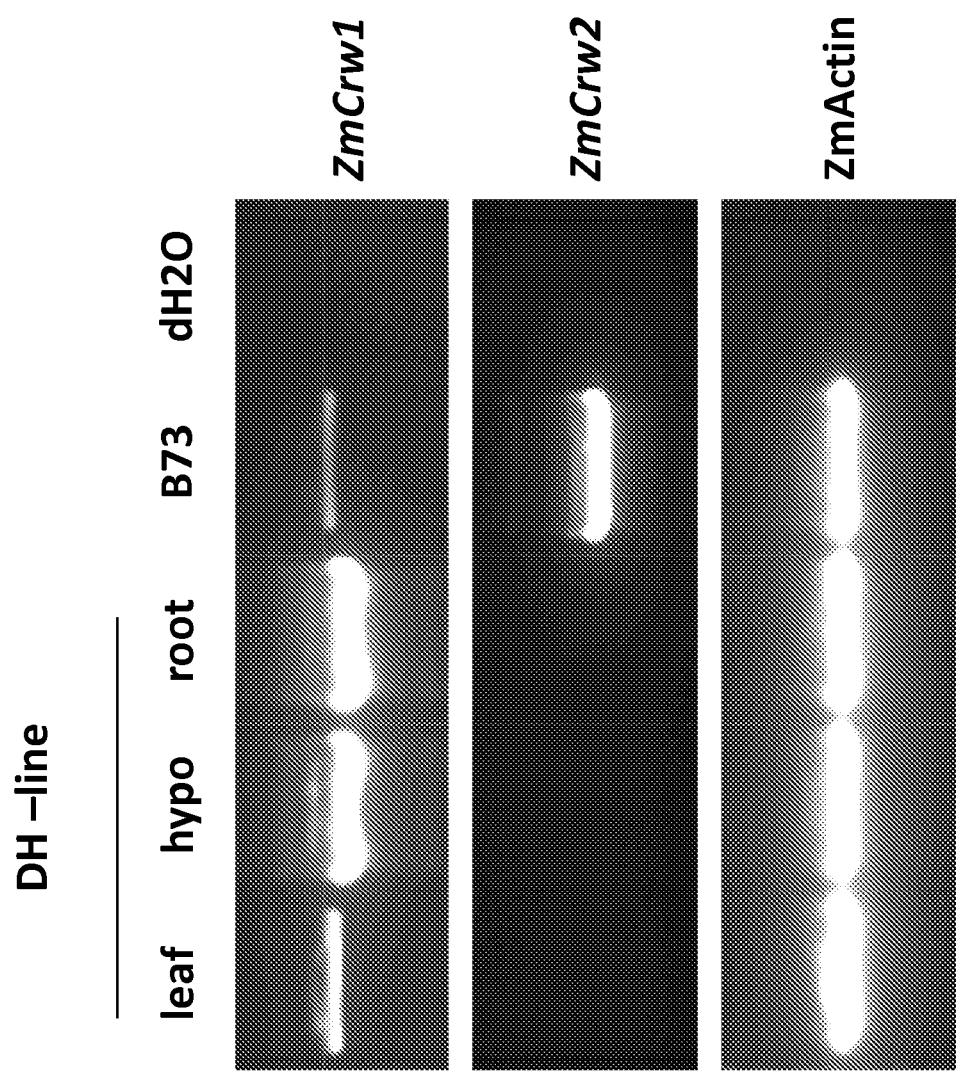

FIG. 9 shows the expression of ZmCrw1 and ZmCrw2 (as assessed using RT-PCR) in a doubled haploid line that is highly susceptible to herbivory by the WCR beetle. Results show that ZmCrw1 is expressed in the doubled haploid line while ZmCrw2 is not (FIG. 9).

FIGS. 10A and B shows that a Crw2 mutant ("MT") has (A) lower levels of cell wall bound p-coumaric acid (pCA) and ferulic acid (FA) and (B) lower levels of lignin, in comparison to wild-type ("WT") during adult stages (p<0.05; unpaired t test).

SEQ ID NO:1 is the nucleotide sequence of the coding region of the wild-type Zea mays Crw2 (ZmCrw2) cDNA.

SEQ ID NO:2 is the amino acid sequence of the wild-type Zea mays CRW2 (ZmCRW2) protein, which is also referred to as a glycosyltransferase (UniProt entry B6TY42).

SEQ ID NO:3 is the nucleotide sequence of the cDNA of the mutant crw2-Mutag allele.

SEQ ID NO:4 is the amino acid sequence of the polypeptide encoded by the mutant crw2-Mutag allele.

SEQ ID NO:5 is the nucleotide sequence of the cDNA of the mutant crw2-EMS allele.

SEQ ID NO:6 is the amino acid sequence of the polypeptide encoded by the mutant crw2-EMS allele.

SEQ ID NO:7 is the amino acid sequence of the Zea mays putative uncharacterized protein (UniProt entry C0PDR7).

SEQ ID NO:8 is the amino acid sequence of the Zea mays putative uncharacterized protein (UniProt entry C4J6G0).

SEQ ID NO:9 is the amino acid sequence of the Oryza sativa putative HGA1 (Identifier 0s06g49320; UniProt entry Q5Z8T7).

SEQ ID NO:10 is the amino acid sequence of the Oryza sativa putative HGA1 (Identifier 0s02g0135500; UniProt entry Q6Z0Z4).

SEQ ID NO:11 is the amino acid sequence of the Sorghum bicolor putative uncharacterized protein Sb10g029380 (UniProt entry C5Z9B2).

SEQ ID NO:12 is the amino acid sequence of the Sorghum bicolor putative uncharacterized protein Sb04g002850 (UniProt entry C5XTX5).

SEQ ID NO:13 is the amino acid sequence of the Glycine max uncharacterized protein (Identifier Glyma05g34170; UniProt entry I1K5F9).

SEQ ID NO:14 is the amino acid sequence of the Glycine max uncharacterized protein (Identifier Glyma08G05490; UniProt entry I1KQG2).

SEQ ID NO:15 is the amino acid sequence of the Arabidopsis thaliana glycosyltransferase family 61 protein (TAIR Identifier: At3g18170; NCBI GI No. G130684813).

SEQ ID NO:16 is the amino acid sequence of the Arabidopsis thaliana At3g18180 locus also referred to as glycosyltransferase family 61 protein (UniProt entry Q9LV22).

SEQ ID NO:17 is the amino acid sequence of the Hordeum vulgare predicted protein (UniProt entry F2DBB4).

SEQ ID NO:18 is the amino acid sequence of the Brachypodium distachyon uncharacterized protein also known as BRADI1G34670 (UniProt entry I1GWV1).

SEQ ID NO:19 is the nucleotide sequence of a homolog of ZmCrw2 from Paspalum notatum (identified in an internal proprietary database and referred to herein as PnCrw2).

SEQ ID NO:20 is the amino acid sequence of the polypeptide encoded by SEQ ID NO:19. The polypeptide is herein referred to as PnCRW2.

SEQ ID NO:21 is the nucleotide sequence of a homolog of ZmCrw2 from Eragrostis nindensis (identified in an internal proprietary database and referred to herein as EnCrw2).

SEQ ID NO:22 is the amino acid sequence of the polypeptide encoded by SEQ ID NO:21. The polypeptide is referred to herein as EnCRW2.

SEQ ID NO:23 is the amino acid sequence of an uncharacterized glycosyltransferase AGO61-like from Glycine max (NCBI GI No. 356511269).

SEQ ID NO:24 is the nucleotide sequence of the forward gene specific primer PHN151293 used for RT-PCR analysis.

SEQ ID NO:25 is the nucleotide sequence of the reverse gene specific primer PHN151298 used for RT-PCR analysis.

SEQ ID NO:26 is the amino acid sequence of the wild-type Zea mays CRW1 (ZmCRW1) protein.

SEQ ID NO:27 is the amino acid sequence of a secondary wall NAC transcription factor 2 from Oryza sativa (UniProt entry G3M8D2).

SEQ ID NO:28 is the amino acid sequence of a putative NAM protein (OsNAC7) from Oryza sativa (Identifier 0s06g04090.1; UniProt entry Q9SNM6).

SEQ ID NO:29 is the amino acid sequence of a putative uncharacterized protein from Sorghum bicolor (Identifier Sb07g001550.1; UniProt entry C5YM23).

SEQ ID NO:30 is the amino acid sequence of a putative NAM protein from Sorghum bicolor (Identifier Sb10g002120.1; UniProt entry Q5NKS7).

SEQ ID NO:31 is the amino acid sequence of an uncharacterized protein from Glycine max (Identifier Glyma16g02200.1; UniProt entry I1MKD6).

SEQ ID NO:32 is the amino acid sequence of an uncharacterized protein from Glycine max (Identifier Glyma07g05660.1; UniProt entry I1 KHQ4).

SEQ ID NO:33 is the amino acid sequence of a NAC domain-containing protein 43 from Arabidopsis thaliana (Identifier At2g46770.1; UniProt entry Q84WP6).

SEQ ID NO:34 is the amino acid sequence of a NAC domain-containing protein 12 from Arabidopsis thaliana (At1g32770.1; UniProt entry Q9LPI7).

SEQ ID NO:35 is the amino acid sequence of a NAC domain-containing protein 66 from Arabidopsis thaliana (Identifier At3g61910.1; UniProt entry Q9M274).

SEQ ID NO:36 is the amino acid sequence of a secondary wall NAC transcription factor 2 from Zea mays (UniProt entry B4FPS5)

SEQ ID NO:37 is the amino acid sequence of a putative NAM protein from Zea mays (UniProt entry Q5NKQ3).

SEQ ID NO:38 is the amino acid sequence of a CRW1 homolog from Brachypodium distachyon (NCBI GI No. 357139497 and herein referred to as BdCRW1).

SEQ ID NO:39 is the amino acid sequence of a putative uncharacterized protein from Vitis vinifera (UniProt entry F6HU82).

SEQ ID NO:40 is the amino acid sequence of a CRW1 homolog from Glycine max (NCBI GI No. 356522480 and herein referred to as GmCRW1).

SEQ ID NO:41 is the amino acid sequence of a NAC domain-containing protein from Gossypium hirsutum (UniProt entry G4V2G0).

SEQ ID NO:42 is the amino acid sequence of a NAC domain class transcription factor (NAC12) from Pyrus malus (UniProt entry D9ZJ90).

SEQ ID NO:43 is the amino acid sequence of a predicted protein from *Hordeum vulgare* (UniProt entry F2DV83).

SEQ ID NO:44 is the amino acid sequence of a CRW1 homolog from *Arabidopsis thaliana* (NCBI GI No. 3510262; UniProt entry Q84WP6).

The sequence descriptions and Sequence Listing attached hereto comply with the rules governing nucleotide and/or amino acid sequence disclosures in patent applications as set forth in 37 C.F.R. § 1.821 1.825.

The Sequence Listing contains the one letter code for nucleotide sequence characters and the three letter codes for amino acids as defined in conformity with the IUPAC IUBMB standards described in Nucleic Acids Res. 13:3021 3030 (1985) and in the Biochemical J. 219 (No. 2):345 373 (1984) which are herein incorporated by reference. The symbols and format used for nucleotide and amino acid sequence data comply with the rules set forth in 37 C.F.R. § 1.822.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

The terms "monocot" and "monocotyledonous plant" are used interchangeably herein.

The terms "dicot" and "dicotyledonous plant" are used interchangeably herein.

The terms "full complement" and "full-length complement" are used interchangeably herein, and refer to a complement of a given nucleotide sequence, wherein the complement and the nucleotide sequence consist of the same number of nucleotides and are 100% complementary.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, or by agricultural observations such as osmotic stress tolerance or yield.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, plant propagules, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different transgenes.

"Transgenic plant" also includes reference to plants which comprise more than one heterologous polynucleotide within their genome. Each heterologous polynucleotide may confer a different trait to the transgenic plant.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single or double-stranded, optionally containing synthetic, non-natural or altered nucleotide bases. Nucleotides (usually found in their 5' monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Coding region" refers to the portion of a messenger RNA (or the corresponding portion of another nucleic acid molecule such as a DNA molecule) which encodes a protein or polypeptide. "Non-coding region" refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

Promoters that cause a gene to be expressed in most cell types at most times are commonly referred to as "constitutive promoters."

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Overexpression" refers to the production of a gene product in transgenic organisms that exceeds levels of production in a null segregating (or non-transgenic) organism from the same experiment.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

The term "locus" generally refers to a genetically defined region of a chromosome carrying a gene or, possibly, two or more genes so closely linked that genetically they behave as a single locus responsible for a phenotype. When used herein with respect to ZmCrw2, the "ZmCrw2 locus" shall refer to the defined region of the chromosome carrying the ZmCrw2 gene including its associated regulatory sequences. Similarly, when used herein with respect to ZmCrw1, the "ZmCrw1 locus" shall refer to the defined region of the chromosome carrying the ZmCrw1 gene including its associated regulatory sequences.

A "gene" shall refer to a specific genetic coding region within a locus, including its associated regulatory sequences. One of ordinary skill in the art would understand that the associated regulatory sequences will be within a distance of about 4 kb from the Zmcrw2 coding sequence, with the promoter located upstream.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "favorable allele" is the allele at a particular locus that confers, or contributes to, a desirable phenotype, or alternatively, is an allele that allows the identification of plants that do not have the desirable phenotype so that they can be removed from a breeding program or planting. A favorable allele of a marker is a marker allele that segregates with the favorable phenotype, or alternatively, segregates with the unfavorable plant phenotype, therefore providing the benefit of identifying plants.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells, that can be cultured into a whole plant.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal W method of alignment.

The Clustal W method of alignment (described by Higgins and Sharp, CABIOS. 5:151-153 (1989); Higgins, D. G. et al., Comput. Appl. Biosci. 8:189-191 (1992)) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB.

After alignment of the sequences, using the Clustal W program, it is possible to obtain "percent identity" and "divergence" values by viewing the "sequence distances" table on the same program; unless stated otherwise, percent identities and divergences provided and claimed herein were calculated in this manner. Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Isolated polynucleotides, cDNAs, polypeptides, recombinant DNA constructs useful for increasing a plant's resistance to an insect pest are provided herein. Also provided are compositions (such as plants or seeds) comprising these recombinant DNA constructs and methods utilizing these recombinant DNA constructs.

CRW2 crw2-Mutag (corn rootworm susceptible) and crw2-EMS are maize mutants whose leaves are devoured by the Western corn rootworm (WCR) beetle. The polypeptide encoded by Crw2 is a glycosyltransferase. Glycosyltransferases are members of a large superfamily that can transfer single or multiple activated sugars to a wide range of small molecular acceptors in plants. Recent studies have shown that glycosyltransferases in plants may have roles in numerous processes of plant growth, development, and response to the environment (Wang, J. and Hou, B. (2009) *Front. Biol. China* 4:39-46).

The mutant alleles of ZmCrw2 (SEQ ID NO:1) are inherited in a recessive fashion and inheritance is controlled by a single gene. ZmCRW2 (SEQ ID NO:2) is a glycosyltransferase from *Zea mays*. CRW2 can refer to the ZmCRW2 (SEQ ID N0:2) or any of its homologs (SEQ ID NOs: 7, 8, 9, 10, 11, 12, 13, 14, 15, 16, 17, 18, 20, 22, and 23).

CRW1 crw1 (corn rootworm susceptible) is a maize mutant whose leaves are devoured by the Western corn rootworm (WCR) beetle (Dhillon B, Moose S P; and Johal G S. (2007). crw1—A novel maize mutant exceptionally susceptible to Western Corn Rootworm. *Maize Genetics Conference*. March 22-25, St. Charles, Ill. Abstract and Presentation available online), which is unusual because the WCR beetle normally feeds on maize pollen and silks and not leaves. Thus, it appears that a mechanism that normally renders maize leaves unpalatable to the WCR beetle is compromised in the mutant.

ZmCrw1 is inherited in a recessive fashion and is controlled by a single gene. CRW1 (SEQ ID NO:26) is a NAC transcription factor from *Zea mays*. CRW1 can refer to the ZmCRW1 (SEQ ID NO:26) or any of its homologs (SEQ ID NOs:27-44).

Isolated Polynucleotides, cDNAs and Polypeptides

The present disclosure includes the following isolated polynucleotides, cDNAs and polypeptides:

An isolated polynucleotide or cDNA comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:2, 7, 8, 9, 10, 11, 12, 13, 14, 15, 16, 17, 18, 20, 22, and 23, and combinations thereof; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. The polypeptide is preferably a CRW2 polypeptide.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:2, 7, 8, 9, 10, 11, 12, 13, 14, 15, 16, 17, 18, 20, 22, and 23, and combinations thereof. The polypeptide is preferably a CRW2 polypeptide.

An isolated polynucleotide or cDNA comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal W method of alignment, when compared to SEQ ID NO:1, 19, or 21; or (ii) a full complement of the nucleic acid sequence of (i). Any of the foregoing isolated polynucleotides may be utilized in any recombinant DNA constructs of the present disclosure.

An isolated polynucleotide or cDNA comprising a nucleotide sequence, wherein the nucleotide sequence is hybridizable under stringent conditions with a DNA molecule comprising the full complement of SEQ ID NO:1, 19, or 21.

An isolated polynucleotide or cDNA comprising a nucleotide sequence, wherein the nucleotide sequence is derived from SEQ ID NO:1, 19, or 21 by alteration of one or more nucleotides by at least one method selected from the group consisting of: deletion, substitution, addition and insertion.

An isolated polynucleotide or cDNA comprising a nucleotide sequence, wherein the nucleotide sequence corresponds to an allele of SEQ ID NO:1, 19, or 21.

An isolated polynucleotide or cDNA comprising: (i) a nucleic acid sequence encoding a polypeptide having an amino acid sequence of at least 90% sequence identity, based on the Clustal W method of alignment, when compared to SEQ ID NO:20 or 22; or (ii) a full complement of the nucleic acid sequence of (i).

It is understood, as those skilled in the art will appreciate, that the disclosure encompasses more than the specific exemplary sequences.

Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N terminal and C terminal portions of the polypeptide molecule would also not be expected to alter the activity of the polypeptide. Each of the proposed modifications is well within the routine skill in the art, as is determination of retention of biological activity of the encoded products.

The protein of the current disclosure may also be a protein which comprises an amino acid sequence comprising deletion, substitution, insertion and/or addition of one or more amino acids in an amino acid sequence presented in SEQ ID NO: 2, 7, 8, 9, 10, 11, 12, 13, 14, 15, 16, 17, 18, 20, 22, and 23. The substitution may be conservative, which means the replacement of a certain amino acid residue by another residue having similar physical and chemical characteristics. Non-limiting examples of conservative substitution include replacement between aliphatic group-containing amino acid residues such as Ile, Val, Leu or Ala, and replacement between polar residues such as Lys-Arg, Glu-Asp or Gln-Asn replacement.

Proteins derived by amino acid deletion, substitution, insertion and/or addition can be prepared when DNAs encoding their wild-type proteins are subjected to, for example, well-known site-directed mutagenesis (see, e.g., Nucleic Acid Research, Vol. 10, No. 20, p. 6487-6500, 1982, which is hereby incorporated by reference in its entirety). As used herein, the term "one or more amino acids" is intended to mean a possible number of amino acids which may be deleted, substituted, inserted and/or added by site-directed mutagenesis.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

Techniques for allowing deletion, substitution, insertion and/or addition of one or more amino acids in the amino acid sequences of biologically active peptides such as enzymes while retaining their activity include site-directed mutagenesis mentioned above, as well as other techniques such as those for treating a gene with a mutagen, and those in which a gene is selectively cleaved to remove, substitute, insert or add a selected nucleotide or nucleotides, and then ligated.

The protein of the present disclosure may also be a protein which is encoded by a nucleic acid comprising a nucleotide sequence comprising deletion, substitution, insertion and/or addition of one or more nucleotides in the nucleotide sequence of SEQ ID NO:1, 19, or 21. Nucleotide deletion, substitution, insertion and/or addition may be accomplished by site-directed mutagenesis or other techniques as mentioned above.

The protein of the present disclosure may also be a protein which is encoded by a nucleic acid comprising a nucleotide sequence hybridizable under stringent conditions with the complementary strand of the nucleotide sequence of SEQ ID NO:1, 19, or 21.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., *Molecular Cloning: A Laboratory Manual, third edition*, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

It is also possible to use a commercially available hybridization kit which uses no radioactive substance as a probe. Specific examples include hybridization with an ECL direct labeling & detection system (Amersham). Stringent conditions include, for example, hybridization at 42° C. for 4 hours using the hybridization buffer included in the kit, which is supplemented with 5% (w/v) Blocking reagent and 0.5 M NaCl, and washing twice in 0.4% SDS, 0.5×SSC at 55° C. for 20 minutes and once in 2×SSC at room temperature for 5 minutes.

Recombinant DNA Constructs

In one aspect, the present disclosure includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 2, 7, 8, 9, 10, 11, 12, 13, 14, 15, 16, 17, 18, 20, 22, and 23, and combinations thereof; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO:1, 19, or 21, and combinations thereof; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes a CRW2 polypeptide. The CRW2 polypeptide may be from *Arabidopsis thaliana*, *Zea mays*, *Glycine max*, *Glycine tabacina*, *Glycine soja*, *Glycine tomentella*, *Oryza sativa*, *Brachypodium distachyon*, *Vitis vinifera*, *Gossypium mexicanum*, *Pyrus malus*, *Hordeum vulgare*, *Brassica napus*, *Sorghum bicolor*, *Saccharum officinarum*, *Triticum aestivum*, *Paspalum notatum*, and *Eragrostis nindensis*.

A recombinant DNA construct comprising an isolated polynucleotide comprising: (i) a nucleic acid sequence encoding a polypeptide having an amino acid sequence of at least 90% sequence identity, based on the Clustal W method of alignment, when compared to SEQ ID NO:20 or 22; or (ii) a full complement of the nucleic acid sequence of (i), operably linked to at least one regulatory element is provided herein. The at least one regulatory element may be a promoter. For example, a promoter may be any one disclosed herein, such as a root-specific promoter or the maize ubiquitin promoter.

Regulatory Sequences

A recombinant DNA construct of the present disclosure may comprise at least one regulatory sequence.

A regulatory sequence may be a promoter.

A number of promoters can be used in recombinant DNA constructs of the present disclosure. The promoters can be selected based on the desired outcome, and may include constitutive, tissue-specific, inducible, or other promoters for expression in the host organism.

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), the constitutive synthetic core promoter SCP1 (International Publication No. 03/033651) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Tissue-specific promoters useful in the current disclosure may include root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790; GI No. 1063664.

Promoters may be derived in their entirety from a native gene, or be composed of different elements derived from different promoters found in nature, or even comprise synthetic DNA segments.

Recombinant DNA constructs of the present disclosure may also include other regulatory sequences, including but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395-4405 (1988); Callis et al., *Genes Dev.* 1:1183-1200 (1987).

Any plant can be selected for the identification of regulatory sequences and genes encoding CRW2 polypeptides to be used in recombinant DNA constructs and other compositions (e.g. transgenic plants, seeds and cells) and methods of the present disclosure. Examples of suitable plants for the isolation of genes and regulatory sequences and for compositions and methods of the present disclosure would include but are not limited to alfalfa, apple, apricot, Arabidopsis, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, switchgrass, tangerine, tea, tobacco, tomato, triticale, turf, turnip, a vine, watermelon, wheat, yams, and zucchini.

Compositions

A composition of the present disclosure includes a transgenic microorganism, cell, plant, and seed comprising the recombinant DNA construct. The cell may be eukaryotic, e.g., a yeast, insect or plant cell, or prokaryotic, e.g., a bacterial cell.

A composition of the present disclosure is a plant comprising in its genome any of the recombinant DNA constructs of the present disclosure. Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit increased resistance to herbivory by an insect pest, or used in a breeding program to produce hybrid seed, which can be grown to produce plants that would exhibit increased resistance to herbivory by an insect pest. The seeds may be maize seeds.

The plant may be a monocotyledonous or dicotyledonous plant, for example, a maize or soybean plant, such as a maize hybrid plant or a maize inbred plant. The plant may also be sunflower, sorghum, canola, wheat, alfalfa, cotton, rice, barley, millet, sugar cane or switchgrass.

The recombinant DNA construct may be stably integrated into the genome of the plant.

Particular embodiments include but are not limited to the following:

1. A plant (for example, a maize plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 2, 7, 8, 9, 10, 11, 12, 13, 14, 15, 16, 17, 18, 20, 22, and 23, and wherein said plant exhibits increased resistance to herbivory by an insect pest when compared to a control plant not comprising said recombinant DNA construct.

2. A plant (for example, a maize plant) comprising in its genome a recombinant DNA construct comprising a polynucleotide operably linked to at least one regulatory sequence, wherein said polynucleotide encodes a CRW2 polypeptide, and wherein said plant exhibits increased resistance to herbivory by an insect pest when compared to a control plant not comprising said recombinant DNA construct.

3. A plant (for example, a maize plant) comprising in its genome a recombinant DNA construct comprising a polynucleotide operably linked to at least one regulatory element, wherein said polynucleotide comprises a nucleotide sequence, wherein the nucleotide sequence is: (a) hybridizable under stringent conditions with a DNA molecule comprising the full complement of SEQ ID NO:1, 19, or 21; or (b) derived from SEQ ID NO:1, 19, or 21 by alteration of one or more nucleotides by at least one method selected from the group consisting of: deletion, substitution, addition and insertion; and wherein said plant exhibits increased resistance to herbivory by an insect pest, when compared to a control plant not comprising said recombinant DNA construct.

4. A plant (for example, a maize plant) comprising in its genome (A) a first recombinant DNA construct comprising a polynucleotide operably linked to at least one regulatory element, wherein said polynucleotide is selected from the group consisting of: (i) a polynucleotide encoding a polypeptide having the amino acid sequence set forth in SEQ ID NO:2, 7, 8, 9, 10, 11, 12, 13, 14, 15, 16, 17, 18, 20, 22, and 23; (ii) a polynucleotide encoding a polypeptide having an amino acid sequence of at least 80% sequence identity, based on the Clustal W method of alignment, when compared to SEQ ID NO:2, 7, 8, 9, 10, 11, 12, 13, 14, 15, 16, 17, 18, 20, 22, and 23; and (iii) a polynucleotide having a nucleotide sequence that is fully complementary to the nucleotide sequence of a polynucleotide of (i) or (ii); and (B) a second recombinant DNA construct comprising a polynucleotide operably linked to at least one regulatory element, wherein said polynucleotide is selected from the group consisting of: (iv) a polynucleotide encoding a polypeptide having the amino acid sequence set forth in SEQ ID NO:26, 27, 28, 29, 30, 31, 32, 33, 34, 35, 36, 37, 38, 39, 40, 41, 42, 43, and 44; (v) a polynucleotide encoding a polypeptide having an amino acid sequence of at least 80% sequence identity, based on the Clustal W method of alignment, when compared to SEQ ID NO:26, 27, 28, 29, 30, 31, 32, 33, 34, 35, 36, 37, 38, 39, 40, 41, 42, 43, and 44, and (vi) a polynucleotide having a nucleotide sequence that is fully complementary to the nucleotide sequence of a polynucleotide of (i) or (ii); and wherein said plant exhibits increased resistance to herbivory by an insect pest when compared to a control plant not comprising said recombinant DNA construct.

5. Any progeny of the plants in the embodiments described herein, any seeds of the plants in the embodiments described herein, any seeds of progeny of the plants in embodiments described herein, and cells from any of the above plants in embodiments described herein and progeny thereof.

A plant cell comprising a recominant DNA construct comprising a recombinant DNA construct comprising an isolated polynucleotide comprising: (i) a nucleic acid sequence encoding a polypeptide having an amino acid sequence of at least 90% sequence identity, based on the Clustal W method of alignment, when compared to SEQ ID NO:20 or 22; or (ii) a full complement of the nucleic acid sequence of (i), operably linked to at least one regulatory element is provided herein. The at least one regulatory element may be a promoter. For example, a promoter may be any one disclosed herein, such as a root-specific promoter or the maize ubiquitin promoter. Also provided is a plant comprising such a plant cell.

Such a plant may display increased resistance to herbivory by an insect pest. The insect pest may be a Coleopteran insect pest. The Coleopteran insect pest may be of the genus *Diabrotica* or *Popiffia*. The insect pest may be a Lepidoperan insect pest. The Lepidopteran insect pest may be European corn borer. The plant may be a monocot. The plant may be maize.

A plant comprising in its genome a recombinant DNA construct comprising a polynucleotide operably linked to at least one regulatory element, wherein said polynucleotide encodes a polypeptide having an amino acid sequence of at least 50% sequence identity, based on the Clustal W method of alignment, when compared to SEQ ID NO:2, 7, 8, 9, 10, 11, 12, 13, 14, 15, 16, 17, 18, 20, 22, and 23, and wherein said plant exhibits increased resistance to herbivory by an insect pest when compared to a control plant not comprising said recombinant DNA construct is provided herein. The at least one regulatory element may be a promoter. For example, a promoter may be any one disclosed herein, such as a root-specific promoter or the maize ubiquitin promoter. Also provided is a plant comprising such a plant cell. Such a plant may display increased resistance to herbivory by an insect pest. The insect pest may be a Coleopteran insect pest. The Coleopteran insect pest may be of the genus *Diabrotica* or *Popiffia*. The insect pest may be a Lepidoperan insect pest. The Lepidopteran insect pest may be European corn borer. The plant may be a monocot. The plant may be maize.

Also provided is a plant comprising in its genome: (a) a first recombinant DNA construct comprising a polynucleotide operably linked to at least one regulatory element, wherein said polynucleotide is selected from the group consisting of: (i) a polynucleotide encoding a polypeptide having the amino acid sequence set forth in SEQ ID NO:2, 7, 8, 9, 10, 11, 12, 13, 14, 15, 16, 17, 18, 20, 22, and 23; (ii) a polynucleotide encoding a polypeptide having an amino acid sequence of at least 80% sequence identity, based on the Clustal W method of alignment, when compared to SEQ ID NO:2, 7, 8, 9, 10, 11, 12, 13, 14, 15, 16, 17, 18, 20, 22, and 23, and (iii) a polynucleotide having a nucleotide sequence that is fully complementary to the nucleotide sequence of a polynucleotide of (i) or (ii); and (b) a second recombinant DNA construct comprising a polynucleotide operably linked to at least one regulatory element, wherein said polynucleotide is selected from the group consisting of: (iv) a polynucleotide encoding a polypeptide having the amino acid sequence set forth in SEQ ID NO:26, 27, 28, 29, 30, 31, 32, 33, 34, 35, 36, 37, 38, 39, 40, 41, 42, 43, and 44; (v) a polynucleotide encoding a polypeptide having an amino acid sequence of at least 80% sequence identity, based on the Clustal W method of alignment, when compared to SEQ ID NO:26, 27, 28, 29, 30, 31, 32, 33, 34, 35, 36, 37, 38, 39, 40, 41, 42, 43, and 44, and (vi) a polynucleotide having a nucleotide sequence that is fully complementary to the nucleotide sequence of a polynucleotide of (i) or (ii); and wherein said plant exhibits increased resistance to herbivory by an insect pest when compared to a control plant not comprising said recombinant DNA construct. The at least one regulatory element may be a promoter. For example, a promoter may be any one disclosed herein, such as a root-specific promoter or the maize ubiquitin promoter. A plant comprising such a plant cell is further provided herein. Such a plant may display increased resistance to herbivory by an insect pest. The insect pest may be a Coleopteran insect pest. The Coleopteran insect pest may be of the genus *Diabrotica* or *Popillia*. The insect pest may be a Lepidopteran insect pest. The Lepidopteran insect pest may be European corn borer. The plant may be a monocot. The plant may be maize.

In any of the embodiments described herein, the CRW1 and/or CRW2 polypeptide may be from *Arabidopsis thaliana, Zea mays, Glycine max, Glycine tabacina, Glycine soja, Glycine tomentella, Oryza sativa, Brachypodium distachyon, Vitis vinifera, Gossypium mexicanum, Pyrus malus, Hordeum vulgare, Brassica napus, Sorghum bicolor, Saccharum officinarum*, or *Triticum aestivum*.

In any of the embodiments described herein, the recombinant DNA construct may comprise at least a promoter functional in a plant as a regulatory sequence.

In any of the embodiments described herein, the plant (for example, the maize plant) may exhibit less yield loss relative to the control plants, for example, at least 25%, at least 20%, at least 15%, at least 10% or at least 5% less yield loss, under similar environmental conditions and pest pressure.

"Insect pest pressure" refers to the level of infestation of an insect.

"Insect" and "insect pest" are used interchangeably herein.

The insect may be in the adult or larval stage. The adult stage is of particular interest.

The insect may be in the order Coleoptera, and the Coleopteran insect may be of the genus *Diabrotica* or *Popiffia*.

*Diabrotica* is a widespread genus of beetles that includes several destructive agricultural pest species including, for example, corn rootworms. Corn rootworms are one of the most economically destructive insects of maize in the United States. The Western corn rootworm, *D. virgifera virgifera*, and the Northern corn rootworm, *D. barberi*, are the most devastating rootworm species in Iowa, a major corn-growing area. A third species, the Southern corn rootworm, *D. undecimpunctata howardi*, causes much economic damage in other regions.

*Popillia* is a genus of scarab beetles, and the most familiar is the Japanese beetle (*Popillia japonica*). The Japanese beetle is a significant insect pest responsible for crop losses around the world.

The insect may be in the order Lepidoptera, and the Lepidopteran insect may be in the genus *Ostrinia*, *Hyphantria*, or *Simyra*. *Ostrinia* is a genus of moths, and one such member is the European Corn Borer, a serious pest of maize.

An insect pest as set forth in the methods of the disclosure may include but is not limited to any species of corn rootworm (such as but not limited to the Western corn rootworm), the Japanese beetle, European Corn Borer, fall webworm (*Hyphantria cunea*), or cattail caterpillar (*Simyra insularis*).

"Herbivory" as used herein is the consumption of living plant tissue by insects. The plant tissue may be tissue from any plant part including but not limited to leaves, stem, roots, reproductive parts, etc. Chronic attack by herbivores can have dramatic cumulative effects on the size, longevity, or reproductive output of individual plants.

"Susceptibility" refers to the inability of a plant variety to restrict the growth and development of a specified pest.

"Resistance" refers to the ability of a plant variety to restrict the growth and development of a specified pest and/or the damage they cause when compared to susceptible plant varieties under similar environmental conditions and pest pressure.

Typically, when a transgenic plant comprising a recombinant DNA construct in its genome exhibits increased resistance to herbivory by an insect pest relative to a reference or control plant, the reference or control plant does not comprise in its genome the recombinant DNA construct.

One of ordinary skill in the art is familiar with protocols for evaluating insect response (i.e. attractiveness or repulsiveness) to plant tissue and for evaluating a plant's level of resistance to an insect pest.

In addition, as presented herein, one can perform a feeding choice assay as a way to assess the level of a plant's resistance (e.g. a maize plant) to an insect pest such as the corn rootworm beetle. In this assay, a PVC box containing a detachable lid is used to contain the insects and plant hosts, and equal weights of freshly harvested mature leaves of the plant hosts are affixed to moist filter paper in a randomized manner. Insects are starved overnight and placed in the box with the tissue. Leaf feeding can be scored on a scale from 0 to 5, with 0 indicating no damage and 5 indicating complete decimation.

One can also evaluate a plant's resistance to an insect pest by the plant's ability to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under sufficient pest presure.

One of ordinary skill in the art would readily recognize a suitable control or reference plant to be utilized when assessing or measuring a phenotype of a transgenic plant in any embodiment of the present disclosure in which a control plant is utilized (e.g., compositions or methods as described herein). For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct (i.e., the progeny not comprising the recombinant DNA construct is the control or reference plant).
2. Introgression of a recombinant DNA construct into an inbred line, such as in maize, or into a variety, such as in soybean: the introgressed line would typically be measured relative to the parent inbred or variety line (i.e., the parent inbred or variety line is the control or reference plant).
3. Two hybrid lines, where the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).
4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

Furthermore, one of ordinary skill in the art would readily recognize that a suitable control or reference plant to be utilized when assessing or measuring a phenotype of a transgenic plant would not include a plant that had been previously selected, via mutagenesis or transformation, for the desired phenotype.

Methods

Methods include but are not limited to methods for increasing resistance to herbivory by an insect pest in a plant, methods for evaluating resistance to an insect pest in a plant, methods of identifying variants and/or naturally occurring alleles of Crw2 that give plants increased resistance to herbivory by an insect pest, and methods for producing seed. The plant may be a monocotyledonous or dicotyledonous plant, for example, a maize or soybean plant. The plant may also be sunflower, sorghum, canola, wheat, alfalfa, cotton, rice, barley, millet, sugar cane or sorghum. The seed may be a maize or soybean seed, for example, a maize hybrid seed or maize inbred seed.

Methods include but are not limited to the following:

A method for transforming a cell (or microorganism) comprising transforming a cell (or microorganism) with any of the isolated polynucleotides or recombinant DNA constructs of the present disclosure. The cell (or microorganism) transformed by this method is also included. In particular embodiments, the cell is eukaryotic cell, e.g., a yeast, insect or plant cell, or prokaryotic, e.g., a bacterial cell. The microorganism may be *Agrobacterium*, e.g. *Agrobacterium tumefaciens* or *Agrobacterium rhizogenes*.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method, and transgenic seed obtained from this transgenic plant. The transgenic plant obtained by this method may be used in other methods of the present disclosure.

A method for isolating a polypeptide of the disclosure from a cell or culture medium of the cell, wherein the cell comprises a recombinant DNA construct comprising a polynucleotide of the disclosure operably linked to at least one regulatory sequence, and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure; and (b) growing the transformed host cell under conditions that are suitable for expression of the recombinant DNA construct wherein expression of the recombinant DNA construct results in production of altered levels of the polypeptide of the disclosure in the transformed host cell.

A method of increasing resistance to herbivory by an insect pest in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 2, 7, 8, 9, 10, 11, 12, 13, 14, 15, 16, 17, 18, 20, 22, and 23; and (b) regenerating a transgenic plant from the regenerable plant cell after step (a), wherein the transgenic plant comprises in its genome the recombinant DNA construct and exhibits increased resistance to a plant pest when compared to a control plant not comprising the recombinant DNA construct. The method may further comprise (c) obtaining a progeny plant derived from the transgenic plant, wherein said progeny plant comprises in its genome the recombinant DNA construct and exhibits increased resistance to herbivory by an insect pest when compared to a control plant not comprising the recombinant DNA construct. The at least one regulatory element may be a promoter. For example, a promoter may be a root-specific promoter or the maize ubiquitin promoter. The insect pest may be a Coleopteran insect pest. The insect pest may be a Coleopteran insect pest of the genus *Diabrotica* or *Popiffia*. The insect pest may be a Lepidoperan insect pest. The Lepidoperan insect pest may be the European corn borer.

A method of increasing resistance to herbivory by an insect pest in a plant, comprising: (A) introducing into a regenerable plant cell: (i) a first recombinant DNA construct comprising a polynucleotide operably linked to at least one regulatory element, wherein said polynucleotide is selected from the group consisting of: (a) a polynucleotide encoding a polypeptide having the amino acid sequence set forth in SEQ ID NO:2, 7, 8, 9, 10, 11, 12, 13, 14, 15, 16, 17, 18, 20, 22, and 23; (b) a polynucleotide encoding a polypeptide having an amino acid sequence of at least 80% sequence identity, based on the Clustal W method of alignment, when compared to SEQ ID NO:2, 7, 8, 9, 10, 11, 12, 13, 14, 15, 16, 17, 18, 20, 22, and 23, and (c) a polynucleotide having a nucleotide sequence that is fully complementary to the nucleotide sequence of a polynucleotide of (i) or (ii); and (ii) a second recombinant DNA construct comprising a polynucleotide operably linked to at least one regulatory element, wherein said polynucleotide is selected from the group consisting of: (a) a polynucleotide encoding a polypeptide having the amino acid sequence set forth in SEQ ID NO:26, 27, 28, 29, 30, 31, 32, 33, 34, 35, 36, 37, 38, 39, 40, 41, 42, 43, and 44; (b) a polynucleotide encoding a polypeptide having an amino acid sequence of at least 80% sequence identity, based on the Clustal W method of alignment, when compared to SEQ ID NO:26, 27, 28, 29, 30, 31, 32, 33, 34, 35, 36, 37, 38, 39, 40, 41, 42, 43, and 44, and (c) a polynucleotide having a nucleotide sequence that is fully complementary to the nucleotide sequence of a polynucleotide of (i) or (ii); and (B) regenerating a transgenic plant from the regenerable plant cell after step (A), wherein the transgenic plant comprises in its genome the recombinant DNA construct and exhibits increased resistance to a plant pest when compared to a control plant not comprising the recombinant DNA construct. The method may further comprise (C) obtaining a progeny plant derived from the transgenic plant, wherein said progeny plant comprises in its genome the recombinant DNA construct and exhibits increased resistance to herbivory by an insect pest when compared to a control plant not comprising the recombinant DNA construct. The at least one regulatory element may be a promoter. For example, a promoter may be any one disclosed herein, such as a root-specific promoter or the maize ubiquitin promoter. A plant comprising such a plant cell is further provided herein. Such a plant may display increased resistance to herbivory by an insect pest. The insect pest may be a Coleopteran insect pest. The Coleopteran insect pest may be of the genus *Diabrotica* or *Popillia*. The insect pest may be a Lepidoperan insect pest. The Lepidopteran insect pest may be European corn borer. The plant may be a monocot. The plant may be maize.

A method of increasing resistance to herbivory by an insect pest in a plant, the method comprising: (a) introducing into a regenerable plant cell a recombinant DNA construct comprising a polynucleotide operably linked to at least one regulatory element, wherein said polynucleotide comprises a nucleotide sequence, wherein the nucleotide sequence is: (a) hybridizable under stringent conditions with a DNA molecule comprising the full complement of SEQ ID NO:1, 19, or 21; or (b) derived from SEQ ID NO:1, 19, or 21 by alteration of one or more nucleotides by at least one method selected from the group consisting of: deletion, substitution, addition and insertion; and (b) regenerating a transgenic plant from the regenerable plant cell after step (a), wherein the transgenic plant comprises in its genome the recombinant DNA construct and exhibits increased resistance to herbivory by an insect pest in a plant when compared to a control plant not comprising the recombinant DNA construct. The method may further comprise (c) obtaining a progeny plant derived from the transgenic plant, wherein said progeny plant comprises in its genome the recombinant DNA construct and exhibits increased resistance to herbivory by an insect pest in a plant, when compared to a control plant not comprising the recombinant DNA construct.

A method of evaluating resistance to an insect pest in a plant, comprising (a) obtaining a transgenic plant, wherein the transgenic plant comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 2, 7, 8, 9, 10, 11, 12, 13, 14, 15, 16, 17, 18, 20, 22, and 23; (b) obtaining a progeny plant derived from said transgenic plant, wherein the progeny plant comprises in its genome the recombinant DNA construct; and (c) evaluating the progeny plant for resistance to an insect pest in a plant compared to a control plant not comprising the recombinant DNA construct.

In another embodiment, a method of evaluating resistance to an insect pest in a plant, comprising: (a) obtaining a transgenic plant, wherein the transgenic plant comprises in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 2, 7, 8, 9, 10, 11, 12, 13, 14, 15, 16, 17, 18, 20, 22, and 23; (b) growing the transgenic plant of part (a) under conditions wherein the polynucleotide is expressed; and (c) evaluating the transgenic plant of part (b) for resistance to an insect pest in a plant compared to a control plant not comprising the recombinant DNA construct.

A method of evaluating resistance to an insect pest in a plant, the method comprising: (a) obtaining a transgenic plant, wherein the transgenic plant comprises in its genome a recombinant DNA construct comprising a polynucleotide operably linked to at least one regulatory element, wherein said polynucleotide comprises a nucleotide sequence, wherein the nucleotide sequence is: (a) hybridizable under stringent conditions with a DNA molecule comprising the full complement of SEQ ID NO:1, 19, or 21; or (b) derived from SEQ ID NO:1, 19, or 21 by alteration of one or more nucleotides by at least one method selected from the group consisting of: deletion, substitution, addition and insertion; (b) obtaining a progeny plant derived from said transgenic plant, wherein the progeny plant comprises in its genome the recombinant DNA construct; and (c) evaluating the progeny plant for increased resistance to herbivory by an insect pest in a plant, when compared to a control plant not comprising the recombinant DNA construct.

In any of the preceding methods or any other embodiments of methods of the present disclosure, in said introducing step said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, said regenerating step may comprise the following: (i) culturing said transformed plant cells in a media comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, at least one regulatory element may be a promoter. For example, a promoter may be a root-specific promoter or the maize ubiquitin promoter. An insect pest may be a Coleopteran insect pest. The insect pest may be a Coleopteran insect pest of the genus *Diabrotica* or *Popiffia*. The insect pest may be a Lepidoperan insect pest. The Lepidoperan insect pest may be the European corn borer. Phenotyping may be established using a feeding choice assay.

The introduction of recombinant DNA constructs of the present disclosure into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation. Techniques for plant transformation and regeneration have been described in International Patent Publication WO 2009/006276, the contents of which are herein incorporated by reference. The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

In another embodiment, a method of identifying a variant of Crw2 that gives plants increased resistance to herbivory by an insect pest in provided. Such method comprises: (a) combining through gene shuffling one or more nucleotide sequences encoding one or more fragments of SEQ ID NO: 2, 7, 8, 9, 10, 11, 12, 13, 14, 15, 16, 17, 18, 20, 22, and 23, or a protein that is at least 70% identical to SEQ ID NO: 2, 7, 8, 9, 10, 11, 12, 13, 14, 15, 16, 17, 18, 20, 22, and 23, or a fragment thereof; (b) transforming the shuffled sequences from step (a) into a population of regenerable plant cells; (c) regenerating a population of transformed plants from the population of transformed regenerable plant cells of step (b); (d) screening the population of transformed plants from step (c) for increased resistance to said insect pest; and (e) identifying the variant from the transformed plant exhibiting the increased resistance. The method can further comprise: (f) introducing into a regenerable plant cell a recombinant construct comprising a variant of Crw2 that gives plants increased resistance to herbivory by an insect pest; (g) regenerating a transgenic plant from the regenerable plant cell after step (f), wherein the transgenic plant comprises in its genome the recombinant DNA construct; and (h) selecting a transgenic plant of (g), wherein the transgenic plant comprises the recombinant DNA construct and exhibits increased resistance to said insect pest, when compared to a control plant not comprising the recombinant DNA construct.

The terms "gene shuffling" and "directed evolution" can be used interchangeably herein. The method of "gene shuffling" consists of iterations of DNA shuffling followed by appropriate screening and/or selection to generate variants of Crw2 nucleic acids or portions thereof having a modified biological activity (Castle et al., (2004) Science 304(5674): 1151-4; U.S. Pat. Nos. 5,811,238 and 6,395,547).

Methods of identifying allelic variants of Crw2 in maize that are associated with increased resistance to herbivory by an insect pest by way of traditional linkage mapping are also provided. In some embodiments, the allelic variants are identified by (a) crossing two maize plants with differing levels of resistance to said insect pest; (b) evaluating allelic variations in the progeny plants with respect to the polynucleotide sequence encoding a protein comprising SEQ ID NO:2, 20, or 22 or in the genomic region that regulates the expression of the polynucleotide encoding the protein; (c) phenotyping the progeny plants for resistance to said insect pest; (d) associating allelic variations with said resistance; and (e) identifying the alleles that are associated with increased resistance to said insect pest. A method comprising identifying an allelic variant of Crw2 in a maize plant that is associated with increased resistance to herbivory by an insect pest is provided herein in which the method comprises the steps of: a) crossing two maize plants with differing levels of resistance to said insect pest; b) evaluating allelic variations in the progeny plants with respect to the polynucleotide sequence encoding a protein comprising SEQ ID NO:2 or in the genomic region that regulates the expression of the polynucleotide encoding the protein; c) phenotyping the progeny plants for resistance to said insect pest; d) associating allelic variations with said resistance; and e) identifying the alleles that are associated with increased resistance to said insect pest. The phenotyping step (c) could be performed using any method of assessing resistance to an insect pest that is known in the art, for example, resistance for each plant in the population is obtained from historical data or could be performed using a feeding choice assay presented herein.

In other embodiments the allelic variants are identified through whole genome association analysis by: (a) obtaining a population of maize plants, wherein said maize plants exhibit differing levels of resistance to said insect pest; (b) evaluating allelic variations with respect to the polynucleotide sequence encoding a protein comprising SEQ ID NO:2, or in the genomic region that regulates the expression of the polynucleotide encoding the protein; (c) associating allelic variations with said resistance; and (d) identifying an allelic variant that is associated with increased resistance to the insect pest. Resistance could be assessed using any method known to one or ordinary skill in the art or the feeding choice assay. Alternatively, historical phenotypic data regarding the resistance could also be used.

Also provided are methods of identifying a maize plant that exhibits increased resistance to herbivory by an insect pest, the method comprising: (a) detecting the presence of at least one allelic variant of Crw2 that is associated with increased resistance to said insect pest, in the genome of the maize plant (wherein the allelic variant can be identified using the methods described above); and (b) identifying a maize plant that comprises said at least one allelic variant. The method can further comprise: (c) crossing said maize plant to a second maize plant; and (d) identifying and selecting progeny plants arising from said cross that have said allelic variant.

In any of the methods presented above, the insect pest may be in the order Coleoptera, and the Coleopteran insect may be of the genus *Diabrotica* or *Popilia*.

Alternatively, the insect pest may be in the order Lepidoptera, and the Lepidopteran insect may be of the genus *Ostrinia*, *Hyphantria*, or *Simyra*.

The insect pest may be any species of corn rootworm, the Japanese beetle, European Corn Borer, fall webworm (*Hyphantria cunea*), or cattail caterpillar (*Simyra insularis*).

In any of the methods presented above, the evaluation of resistance to an insect pest can comprise any protocol known to one of ordinary skill in the art. The feeding choice assay presented herein could also be used.

In any of the methods presented above, the plant is a monocot plant and can be maize.

EXAMPLES

The present disclosure is further illustrated in the following Examples, in which parts and percentages are by weight and degrees are Celsius, unless otherwise stated. It should be understood that these Examples, while indicating embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

Example 1

Foliar Feeding Choice Assay

A feeding choice assay was performed to assess the level of resistance to corn rootworm beetles in Crw2 mutant and wild-type plants. A PVC box containing a detachable lid was used, and equal weights of freshly harvested mature leaves from both mutant and wild-type plants are affixed to moist filter paper in a randomized manner. Western corn rootworm beetles and southern corn rootworm beetles, which had been starved overnight, were placed into the box. Previous observations showed that the establishment of feeding preference is usually preceded by random scouting and within the first 45 minutes, and that preferential feeding usually continues until the leaves of choice are completely devoured. Leaf feeding was scored on a scale from 0 to 5, with 0 indicating no damage and 5 indicating complete decimation.

Example 2

Cloning and Validation of the Crw2 Gene

A maize mutant showing enhanced susceptibility to WCR adults was isolated from an EMS population and named crw2-EMS. Independently, another WCR-susceptible mutant named crw2-Mutag was identified in an F2 population derived from a Mu-active line. The Crw2 mutants showed enhanced susceptibility to WCR adults as well as to Japanese beetles and European Corn Borer (ECB when evaluated in field testing. Both crw2-EMS and crw2-Mutag segregated as monogenic recessive, mapped to the same region of chromosome 5, and were allelic to each other in reciprocal crosses. A candidate gene was isolated from the crw2-Mutag mutant using co-segregation analysis, and the gene (SEQ ID NO:1) was found to encode a putative Homogalacturonan (HGA1), which is also annotated as "Glycosyltransferase AER61" or a "putative uncharacterized protein". The candidate gene comprised two exons and one intron and encoded a product 445 amino acids (aa) in length (SEQ ID NO:2) with one transmembrane helix (TMH) of 20aa (from amino acid 13-32 of the peptide). The transmembrane helix is expected to localize the protein to ER/Golgi, with the first 12 amino acids of the peptide facing the organelle interior and the rest (from aa 33-455) hanging outside into the cytoplasm. Cloning and sequence of crw2-Mutag (SEQ ID NO:3 is the nucleotide sequence of the cDNA and SEQ ID NO:4 is the amino acid sequence of the encoded polypeptide) revealed that the Mu-element added 145 bp (See alignment FIGS. 1A-1G).

Figure 3:
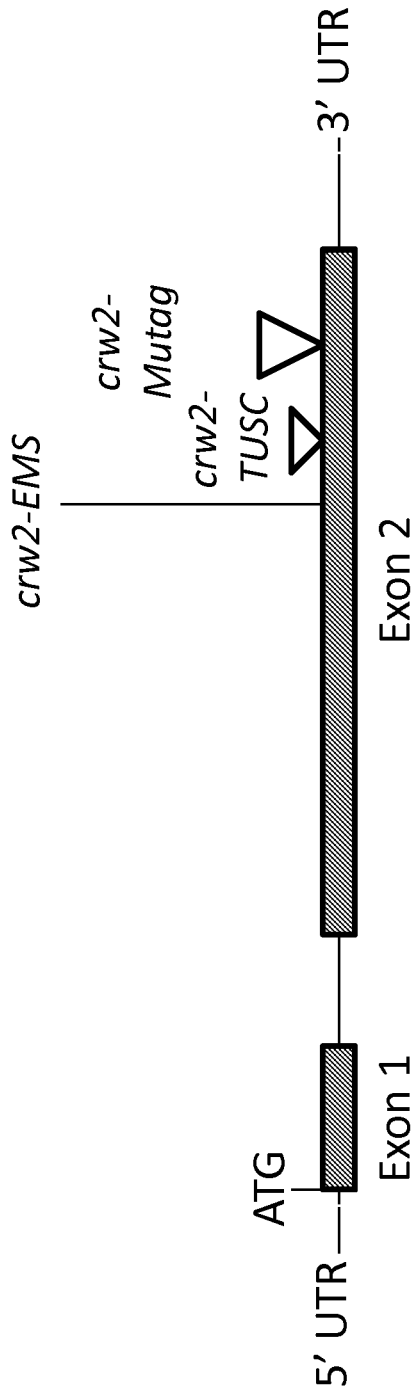
FIG. 3 shows the structure of the maize Homogalacturonan1 (HGA1) gene (also referred to as glycosyltransferase AER61 or ZmCrw2). The positions of the two Mutator insertions and the EMS allele are shown.
Figure 4A:
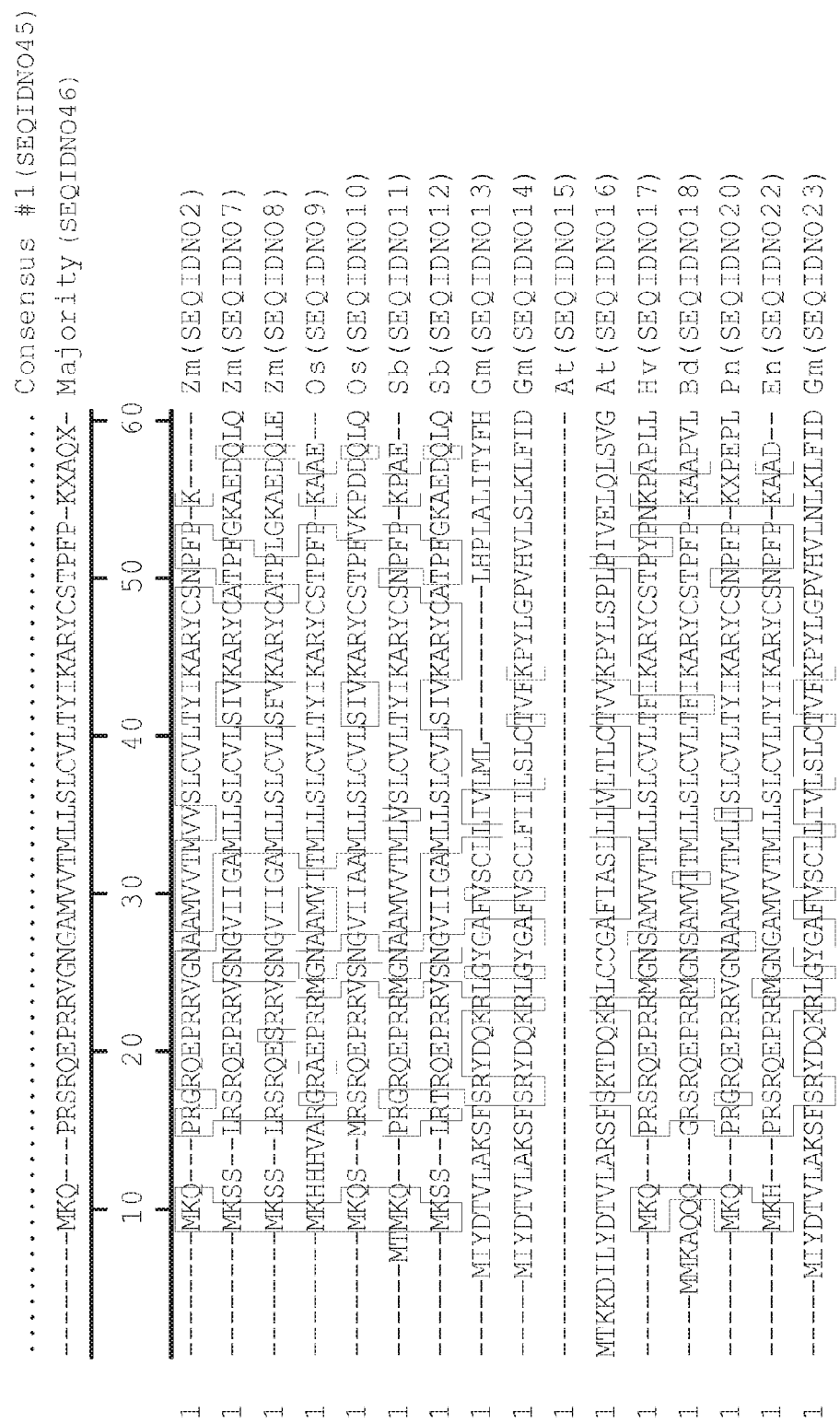
Figure 4B:
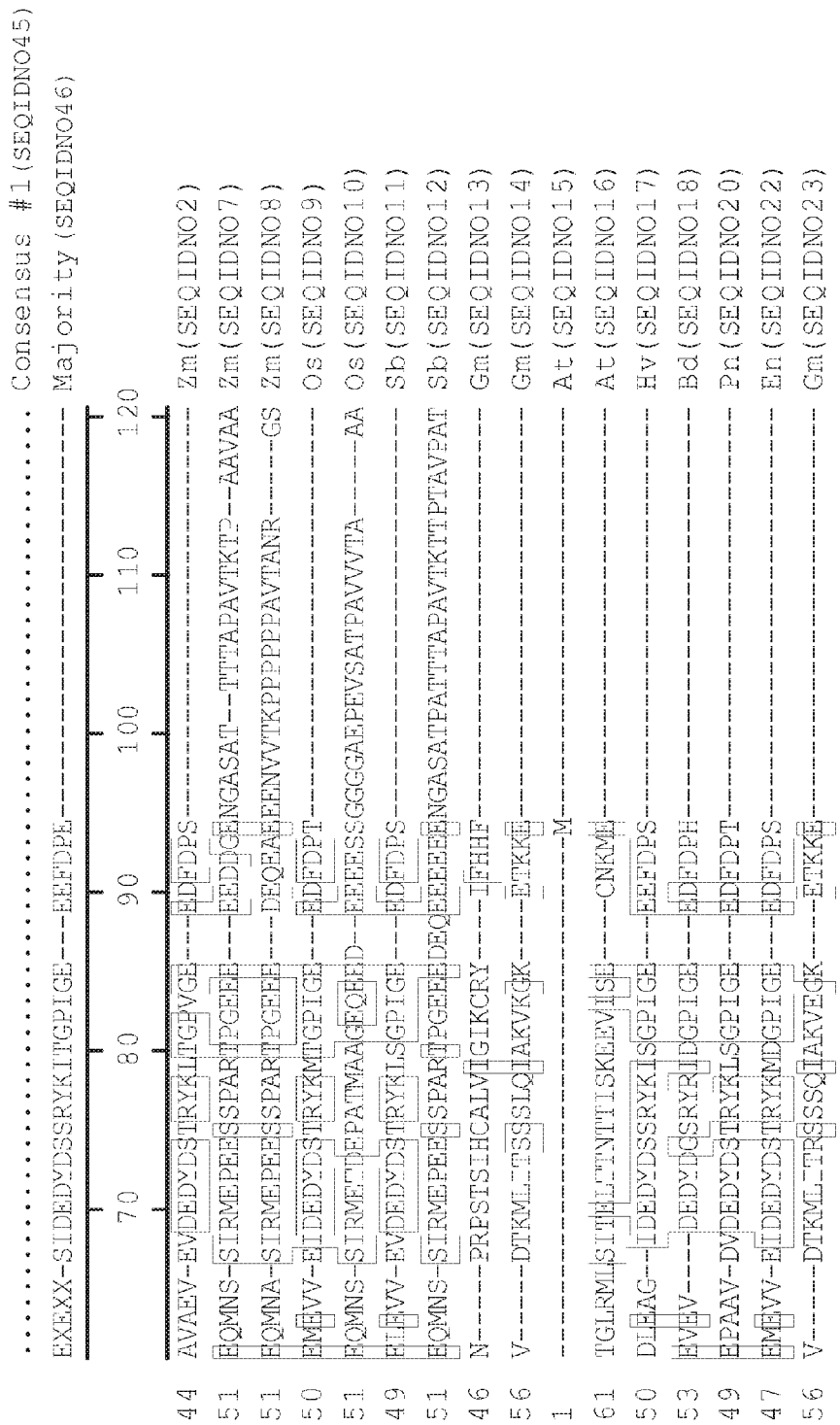
Figure 4C:
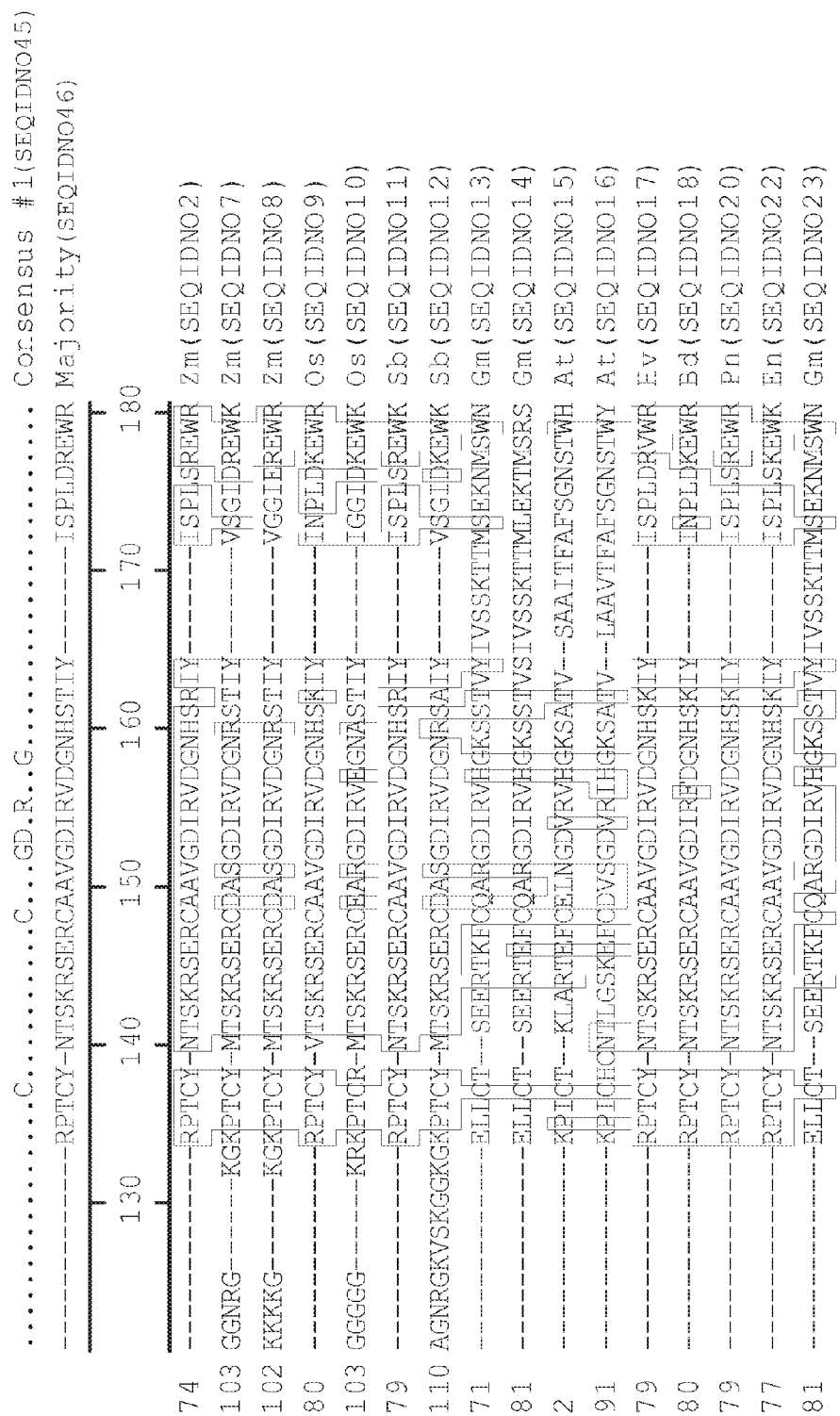
Figure 4E:
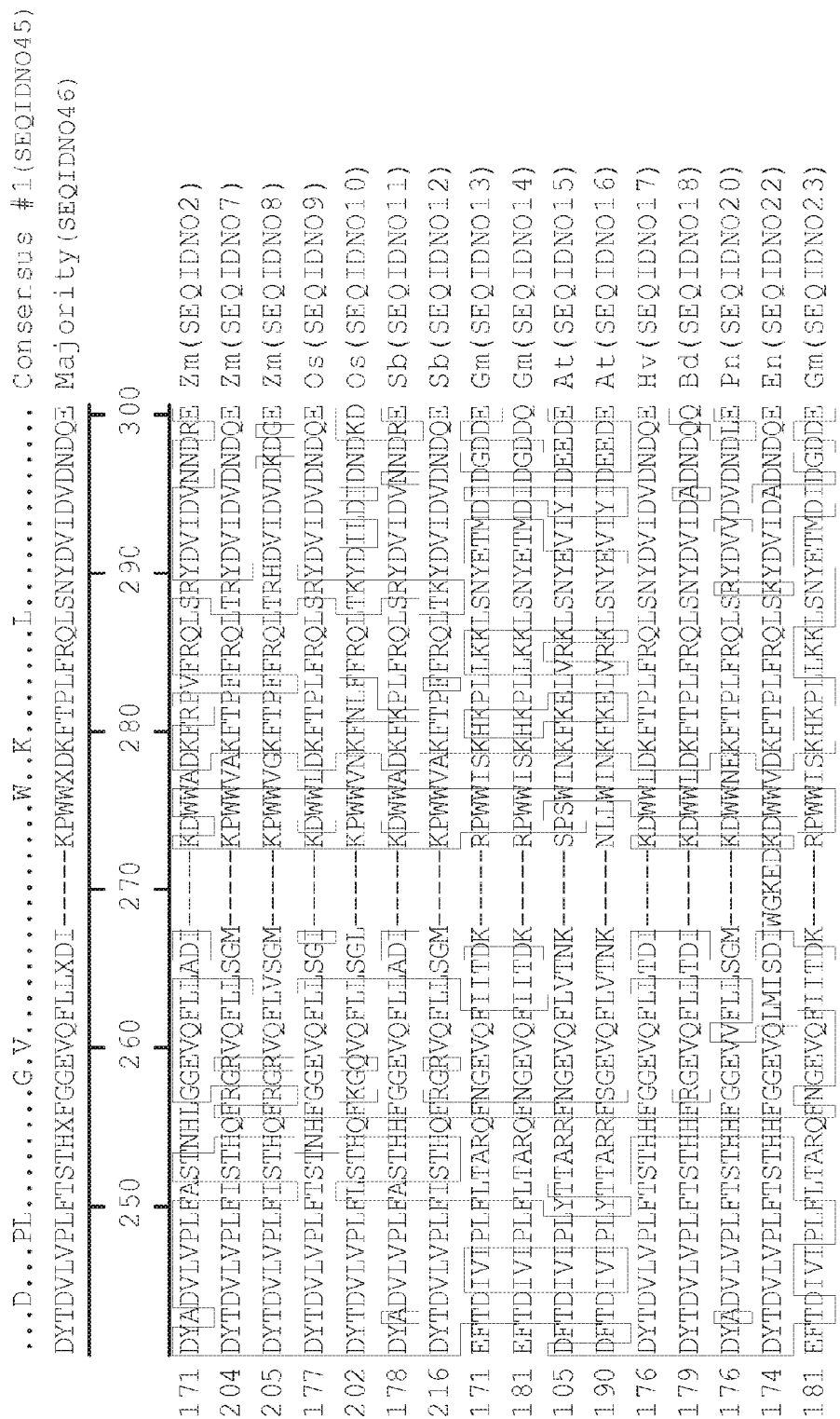
Figure 4G:
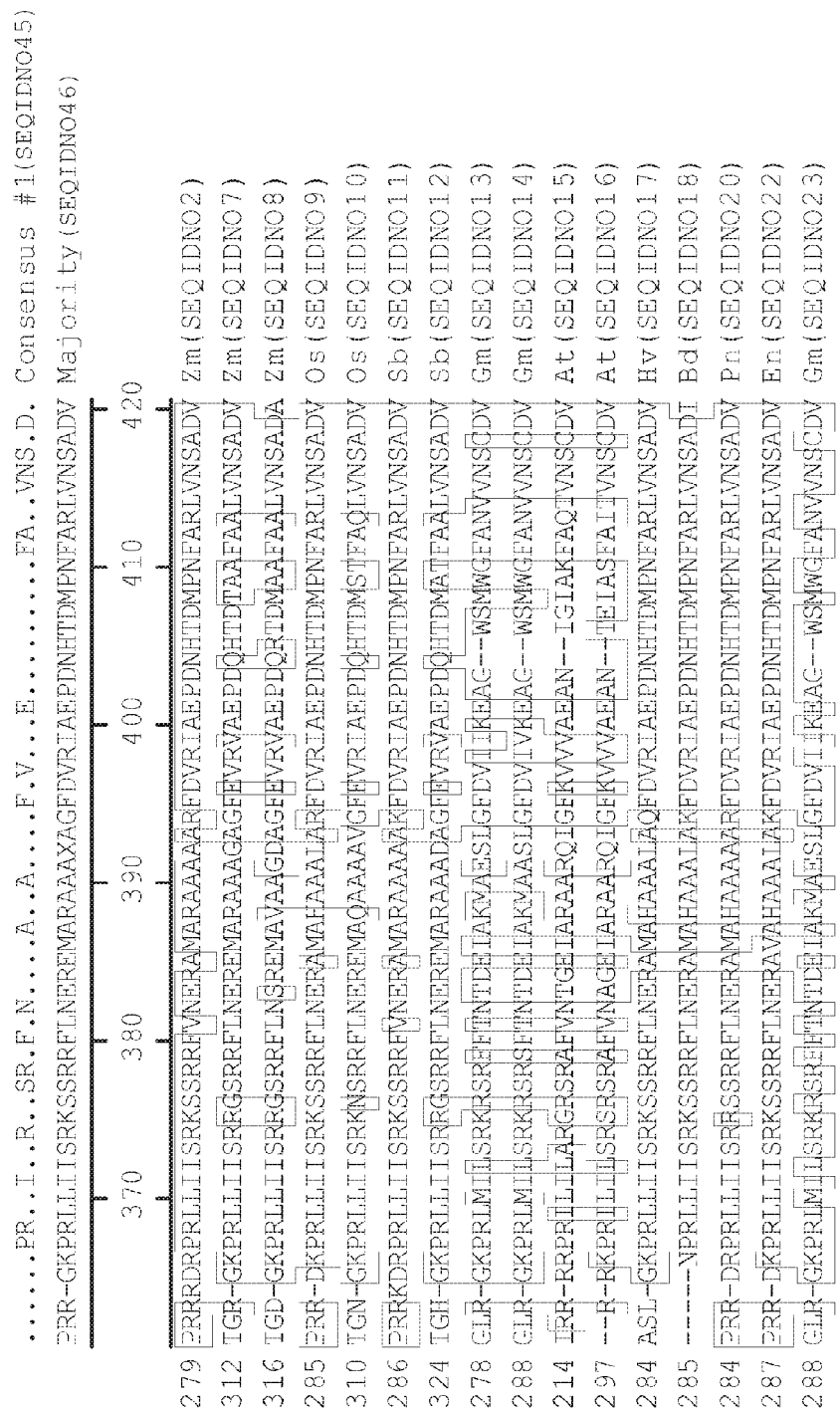
Figure 4I:
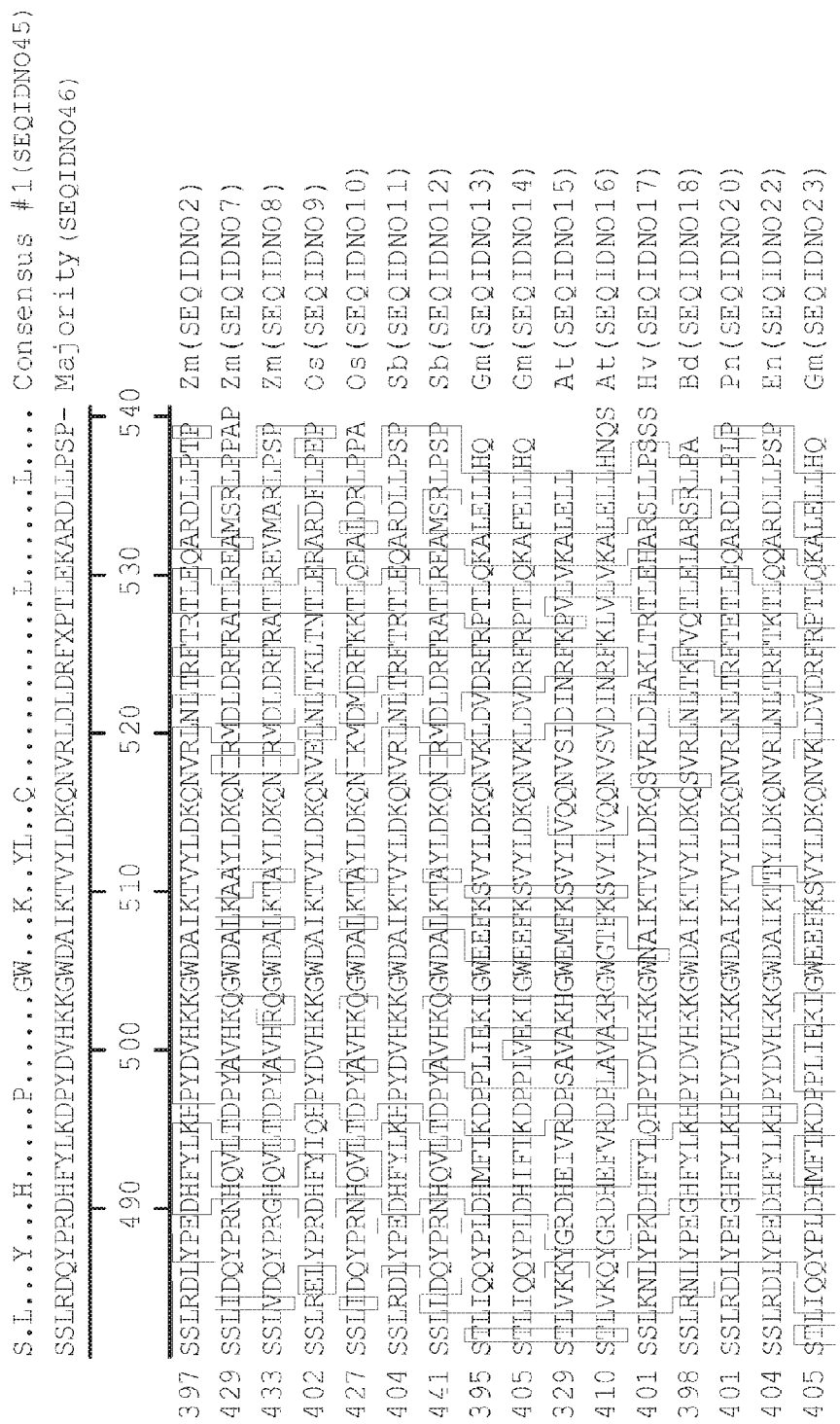

To validate the candidate gene, a set of nested primers was used to amplify the full length gene from the crw2-EMS mutant allele (SEQ ID NO:5 is the nucleotide sequence of the cDNA and SEQ ID NO:6 is the amino acid sequence of the encoded polypeptide) and its progenitor MO20W, a public maize inbred line. A single amino acid change R292C was detected in the crw2-EMS allele as compared to the MO20W HGA1 gene (FIGS. 2A-2F). This amino acid change is in the conserved region of HGA1 and is likely the causative allele of the crw2-EMS mutation. An independent TUSC allele with a Mutator insertion located between the positions of the EMS allele and the Mu-tag allele was isolated and subjected to phenotypic and molecular analyses. The TUSC allele was found to be allelic to crw2-Mutag allele and showed similar enhanced susceptibility to WCR adults and to Japanese beetles. FIG. 3 shows a diagram of the maize Crw2 gene structure and the positions of each of the Crw2 mutations. Additional validation for the function of this gene was identified in a doubled haploid line that is highly susceptible to WCR beetle. The expression of ZmCrw1 and ZmCrw2 was examined in the doubled haploid line using RT-PCR. Results show that ZmCrw1 is expressed in the doubled haploid line while ZmCrw2 is not (FIG. 9).

Example 3

Identification of Homologs of the Maize CRW2 Polypeptide

The maize CRW2 polypeptide can be analyzed for similarity to all publicly available amino acid sequences contained in the "nr" database using the BLASTP algorithm provided by the National Center for Biotechnology Information (NCBI) as well as to the DUPONT™ proprietary internal databases.

A BLAST search using the sequence of the maize CRW2 (SEQ ID NO:2) polypeptide revealed similarity of the maize CRW2 polypeptide to homogalacturonans from various organisms. Shown in Table 1 (non-patent literature are the BLASTP results for the amino acid sequence of the maize CRW2. Also shown in Table 1 are the percent sequence identity values for each pair of amino acid sequences using the Clustal W method of alignment with default parameters:

TABLE 1

| BLASTP Results for Maize CRW2 Polypeptide (Non-patent) | |
|---|---|
| UniProt Identifier | % Seq Identity |
| C0PDR7 (SEQ ID NO: 7) | 64.5 |
| C4J6G0 (SEQ ID NO: 8) | 60.7 |
| Q5Z8T7 (SEQ ID NO: 9) | 86.3 |
| Q6Z0Z4 (SEQ ID NO: 10) | 63.5 |
| C5Z9B2 (SEQ ID NO: 11) | 93.8 |
| C5XTX5 (SEQ ID NO: 12) | 64.7 |
| I1K5F9 (SEQ ID NO: 13) | 40.5 |
| I1KQG2 (SEQ ID NO: 14) | 38.6 |
| Q9LV23 (SEQ ID NO: 15) | 41.9 |
| Q9LV22 (SEQ ID NO: 16) | 36.7 |
| F2DBB4 (SEQ ID NO: 17) | 83.0 |

TABLE 1-continued

| BLASTP Results for Maize CRW2 Polypeptide (Non-patent) | |
|---|---|
| UniProt Identifier | % Seq Identity |
| I1GWV1 (SEQ ID NO: 18) | 82.4 |
| PnCRW2* (SEQ ID NO: 20) | 89.4 |
| EnCRW2* (SEQ ID NO: 22) | 86.8 |
| NCBI GI No. 356511269 (SEQ ID NO: 23) | 40.0 |

*indicates that the sequence was discovered in an internal proprietary database

Figure 5:
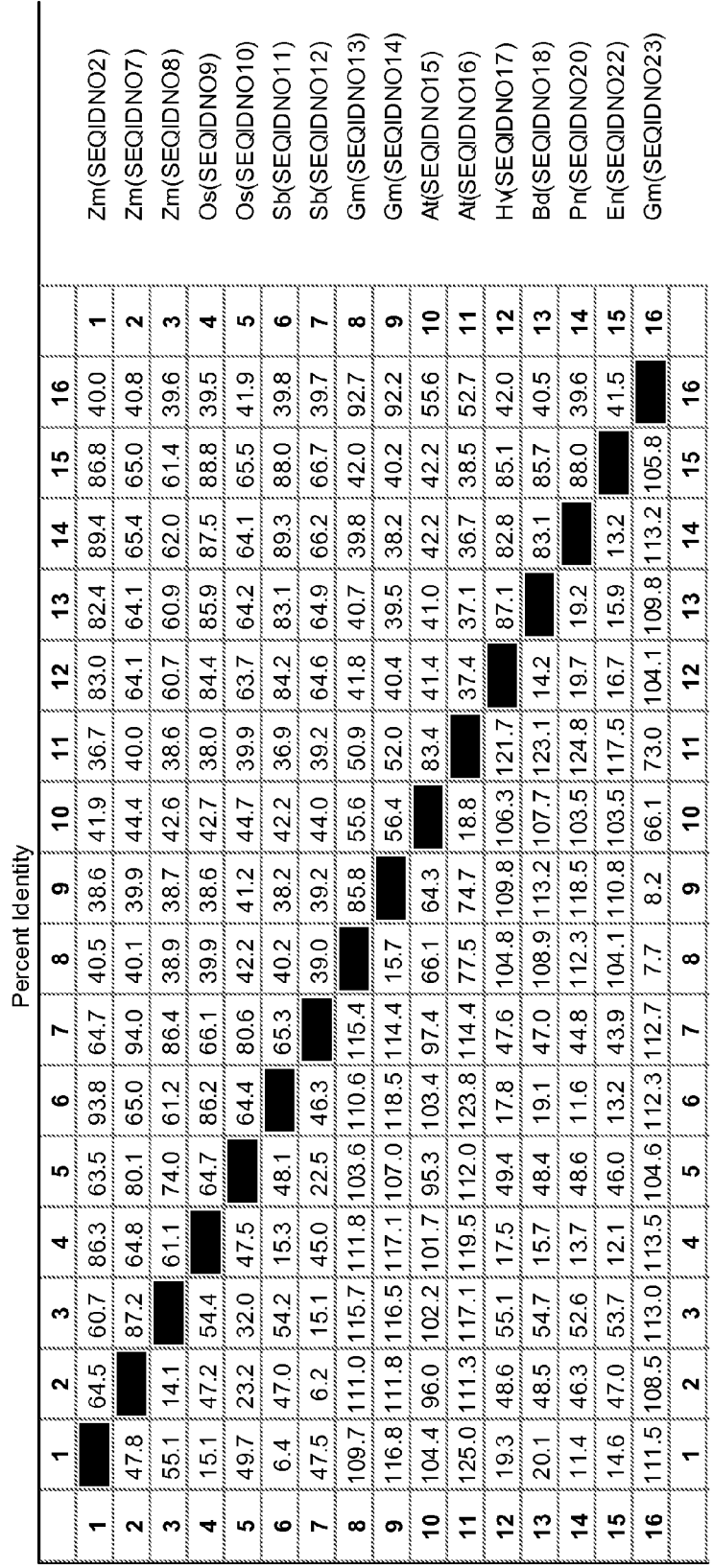
FIG. 5 shows the percent sequence identity and the divergence values for each pair of amino acids sequences of the polypeptides displayed in FIGS. 4A-4J.

FIGS. 4A-4J present an alignment of the amino acid sequences of the polypeptides set forth in SEQ ID NOs:2, 7, 8, 9, 10, 11, 12, 13, 14, 15, 16, 17, 18, 20, 22, and 23. FIG. 5 presents the percent sequence identities and divergence values for each sequence pair presented in FIGS. 4A-4J.

Sequence alignments and percent identity calculations were performed using the Megalign® program of the LASERGENE® bioinformatics computing suite (DNASTAR® Inc., Madison, Wis.). Multiple alignment of the sequences was performed using the Clustal W method of alignment (Thompson et al. (1994) *Nucleic Acids Research.* 22:4673-80) with the default parameters (GAP PENALTY=10, GAP LENGTH PENALTY=0.20). Default parameters for pairwise alignments using the Clustal method were GAP PENALTY=10.00 and GAP LENGTH=0.10. The Protein Weight Matrix used was the Gonnet series.

Example 4

RT-PCR Analysis of the ZmCrw2 Gene in Mutants and Wild-Type Sibs

Total RNA samples were collected from leaf, stalk, and root tissue of 10-day-old seedlings of crw2-Mutag mutants and their WT siblings, and RT-PCR analysis was completed using gene specific primers (SEQ ID NO:24 and SEQ ID NO:25; FIG. 6A). The crw2-Mutag mutant showed differential expression in three tissues (more in stalk as compared to leaf and root samples) and has a transcript that is 145 bp longer than in WT-sibs. Cloning and sequencing of the crw2-Mutag transcript revealed that the Mu-element interferes with intron-splicing. The Mu-element added 141 bp of the MuTIR (Terminal Inverted Repeat) end and 4 bp from a 9 bp direct duplication, resulting in a frame shift (changing the last 73 amino acids as compared to the WT). RT-PCR of the crw2-TUSC mutant showed complete absence of Crw2 transcript in leaves as compared to its WT-sibs (FIG. 6B).

Example 5

Expression of ZmCrw2 Gene in Different Tissues Using Lynx Database

The Lynx database shows that the expression of ZmCrw2 is relatively low in different tissues such as elongating internodes (370 PPM), roots (367 PPM), inner husks at silking stage (324 PPM), tassel (310 PPM), and vascular bundles (220 PPM) (FIG. 7). The expression of the ZmCrw2 gene in leaf tissue is highest in V5 leaves (300 PPM); however, expression in V5 leaf tissue goes down significantly in response to European Corn Borer (ECB) infection. When V5 leaf whorls were infested with ECB larvae, the expression of ZmCrw2 was 300, 200, 150, and 137 RPMs at 0 h, 3 h, 6 h, and 24 h, respectively, after infestation.

Example 6

Crw1 and Crw2 Pathway Analysis

TBO staining of crw2-EMS resulted in a pattern that was identical to that of crw1-Ac, suggesting that both of these mutants have defects in a single genetic pathway or network.

To investigate this link further, differences in the Crw2 transcript levels at various time points post—insect feeding were compared between the Crw1 mutant and WT plants. Seven week old plants of crw1-Ac mutants and their WT-sibs were enclosed in a tent in the field and then infested with adult beetles that had been fasting for 16 hours. RNA was collected at 0 min, 45 min, 1 hr, 6 hr, 12 hr, 24 hr, 36 hr, and 48 hr after infestation. RNA samples were then pooled from different time points for the mutants (pool 1) and WT-sibs (pool 2). Crw2 transcript levels were evaluated in each of the two pools at the various time points. A significant upregulation in Crw2 transcript levels was observed immediately (45 min) in the wild-type sibs ("WT-sibs") as compared to crw1-Ac mutant plants (FIG. 8). These results were also confirmed in RNA Seq experiments where the Crw2 transcript was 2.8 times higher (at log 2 scale) in Crw2 WT-sibs. These results indicated that Crw2 is insect-inducible and that responsiveness to insect feeding is dependent on having a functional Crw1 product.

These results also suggested that Crw1 and Crw2 belong to the same genetic or biochemical network and Crw2 may be acting downstream of the Crw1.

Example 7

Overexpressing Crw2 in Plants

The maize Crw2 gene or any of its homologs can be inserted into a vector, which can further be transformed into plants (including but not limited to maize) using methods known to one of ordinary skill in the art. Phenotypic analysis can then be performed similarly to that in previously described Examples or using any known method of assessment to determine the plant's resistance to an insect pest such as but not limited to the Western corn rootworm, the Japanese beetle, and the European Corn Borer.

Maize transformation vectors were built by constructing Gateway-competent entry vectors in which a fragment of DNA containing ZM-CRW2 was ligated into a vector containing the maize ubiquitin promoter, thereby resulting in a cassette in which expression of ZM-Crw2 was driven by the maize ubiquitin promoter. The resulting entry vector was combined with another vector via an LR reaction (methods were followed according to Invitrogen for Gateway LR reactions) to produce a construct appropriate for *Agrobacterium*-mediated transformation of maize.

A second vector was built in a similar manner using a vector with a backbone having the SB-RCC3 promoter as the recipient entry vector, thereby resulting in a cassette in which expression of ZM-Crw2 was driven by the SB-RCC3 promoter, a root-specific promoter from sorghum (US20120210463). The resulting entry vector was combined with another vector via an LR reaction to produce a construct appropriate for *Agrobacterium*-mediated transformation.

T0 maize plants were produced, and the plants were placed in the greenhouse for phenotypic analysis.

Example 8

Overexpressing Crw1 and Crw2 in Plants

Both Crw1 and Crw2 can be overexpressed in a plant using methods known to one of ordinary skill in the art. The Crw1 gene can be from maize (such as SEQ ID NO:26) or can be a homolog of the ZmCrw1 gene (SEQ ID NOs:27-44). Similarly, the Crw2 gene can be from maize (SEQ ID NO:1) or can be a homolog of the ZmCrw2 gene. Phenotypic analysis can then be performed as described in previous Examples or using any method known in the art to determine the plant's resistance to an insect pest such as but not limited to the Western corn rootworm, the Japanese beetle, and the European Corn Borer.

Example 9

Further Assessment of Crw2 Mutant Phenotype

Crw2 mutants and corresponding wild-type (WT) siblings were planted in the field at bi-weekly intervals from the beginning of May to the end of June during the summers of 2012 and 2013. Plants were assessed for insect damage by the Western corn rootworm (WCR) beetle in the middle of July when the WCR pressure is at its maximum. Irrespective of the availability of young mutant seedlings, the foliar susceptibility phenotype was not observed until the Crw2 mutant plants reached the age of 5 weeks or more. Thereafter, the foliar damage continued to occur steadily and resulted in complete defoliation of the mutant plant under heavy WCR infestation. In addition, Crw2 mutants fell prey to diverse insect herbivores that included Japanese beetles, European corn borer, fall webworm, and cattail caterpillar.

Example 10

Biochemical Characteristics of the Maize Crw2 Gene

Staining of Crw2 mutant leaves with toluidine blue O (TBO), which reacts with free hydroxyl groups in the cell wall, shows reduced staining in intercostal cells, presumably resulting in compromised tensile strength. To test if this was due to reduction in the levels of cell wall bound p-coumaric acid (pCA) and ferulic acid (FA), quantification of these hydroxycinnamates was performed with the juvenile (V3 stage) and adult (V8 stage) epidermal cell walls of both Crw2 and wild-type leaves. A significant reduction in pCA and FA levels was observed in Crw2 mutants as compared to WT siblings, but only in the adult leaves (FIG. 10A).

To address if the reduced levels of hydroxycinnamates also resulted in reduced lignin levels, lignin was extracted from isolated cell walls of adult (V8 stage) Crw2 mutant and WT-sib leaves as acetyl bromide soluble (ABS) fraction and analyzed by UV spectroscopy. Sure enough the levels of ABS lignin are significantly lower ($p<0.05$; unpaired t test) in the adult leaves of Crw2 in comparison to wild-type leaves (FIG. 10B).

SEQUENCE LISTING

<160> NUMBER OF SEQ ID NOS: 46

<210> SEQ ID NO 1
<211> LENGTH: 1725
<212> TYPE: DNA
<213> ORGANISM: Zea mays

<400> SEQUENCE: 1

| | | | | | |
|---|---|---|---|---|---|
| atgaagcagc | cgaggggccg | gcaggagccg | cgccgggtgg | gcaacgccgc | catggtcgtc | 60 |
| accatggtcg | tctccctctg | cgtcctcacg | tacatcaagg | cgcgatactg | ctccaaccct | 120 |
| ttccccaagg | cggtggcgga | ggtggaggtg | gacgaggact | acgacagcac | gcggtacaag | 180 |
| ctgacgggcc | ccgtgggcga | ggaggacttc | gacccgtccc | gccccacctg | ctacaacacc | 240 |
| agcaagcggt | cggagcggtg | cgccgccgtg | gcgacatcc | gcgtggacgg | caaccactcg | 300 |
| cggatctaca | tcagcccgct | gtcccgcgag | tggcggacca | agccgtacgc | gcggcggcac | 360 |
| gacgccgtgg | ccatggacga | cgtgcgcgag | ttcacgctgg | tccccttcgg | cggccccaac | 420 |
| gacacggccg | tgccgccgct | ctgcacgcgc | acccactccg | tcccgggctt | cctcttctcc | 480 |
| agcggcgggt | tcgcgggcaa | cctgtaccac | gactacgccg | acgtgctggt | gccgctcttc | 540 |
| gccagcacca | accacctggg | cggggaggtc | cagttcctgc | tggccgacat | caaggactgg | 600 |
| tgggccgaca | agttccgccc | gctcttccgc | cagctctccc | gctacgacgt | catcgacgtg | 660 |
| aacaacgacc | gcgaggtgca | ctgcttcccg | cggatcatca | tcggctccac | cttccaccgc | 720 |
| gccatgggca | tcgaccccctc | gcgctcgccc | ggcggcgtca | cggtggccga | cttcaagcgc | 780 |
| ctgctccgcc | gcgcgttccg | gctggagcgc | gccgtcgcgt | cgcggtcggg | ggcgccccgg | 840 |
| cgccgggacc | ggccccgcct | cctcatcatc | tcgcgcaaga | gctcgcgccg | cttcgtcaac | 900 |
| gagcgcgcca | tggcgcgcgc | cgcggcggcc | gcccggttcg | acgtgcggat | cgccgagccc | 960 |
| gacaaccaca | cggacatgcc | caacttcgcg | aggctggtga | actcggcgga | cgtgatgatg | 1020 |
| ggcgtgcacg | gcgccgggct | caccaacatg | gtgttcctgc | ccagccgcgc | cgtgctggtg | 1080 |
| caggtggtgc | cgttcggcgg | gctggagtgg | ctcacccgcg | tcaccttcaa | ggaccccgca | 1140 |
| agggacatgg | acgtcacgta | catggagtac | aacgtgtcgc | tggaggagag | ctcgctcagg | 1200 |
| gacctctacc | cggaggacca | cttctacctg | aagcacccct | acgacgtgca | caagaagggg | 1260 |
| tgggacgcca | tcaagacggt | gtacctggac | aagcagaacg | tcaggctcaa | cctcaccagg | 1320 |
| ttcaccagga | cgctggagca | ggcgcgagat | ctcttgccga | cgccatgact | gatgatgacc | 1380 |
| tcccctctt | tcctctgctc | tgctgcaggt | ttcattcact | tcagatcagc | tgctcacctc | 1440 |
| acttcacgcc | gtgtctctct | ctcttttttt | tttctgttgt | tgttctatac | atatacttgt | 1500 |
| ttcctcttct | cctttcccct | ctctctctag | tctctcccctc | tccactcttg | tggtggcaag | 1560 |
| attcatttct | ttcattgttt | tgttttttgt | tgttgttgtt | gaggaaggat | aggaacaaaa | 1620 |
| acaaggtatt | gtcgtgtcca | aggttaatct | acacaaacac | acactgtaaa | tgattgattg | 1680 |
| attgctgtca | gtagaggcga | acacaaggaa | taggtaaaaa | aaaaa | | 1725 |

<210> SEQ ID NO 2
<211> LENGTH: 455
<212> TYPE: PRT
<213> ORGANISM: Zea mays

```
<400> SEQUENCE: 2

Met Lys Gln Pro Arg Gly Arg Gln Glu Pro Arg Arg Val Gly Asn Ala
1               5                   10                  15

Ala Met Val Val Thr Met Val Val Ser Leu Cys Val Leu Thr Tyr Ile
            20                  25                  30

Lys Ala Arg Tyr Cys Ser Asn Pro Phe Pro Lys Ala Val Ala Glu Val
        35                  40                  45

Glu Val Asp Glu Asp Tyr Asp Ser Thr Arg Tyr Lys Leu Thr Gly Pro
    50                  55                  60

Val Gly Glu Glu Asp Phe Asp Pro Ser Arg Pro Thr Cys Tyr Asn Thr
65                  70                  75                  80

Ser Lys Arg Ser Glu Arg Cys Ala Ala Val Gly Asp Ile Arg Val Asp
                85                  90                  95

Gly Asn His Ser Arg Ile Tyr Ile Ser Pro Leu Ser Arg Glu Trp Arg
            100                 105                 110

Thr Lys Pro Tyr Ala Arg Arg His Asp Ala Val Ala Met Asp Asp Val
        115                 120                 125

Arg Glu Phe Thr Leu Val Pro Phe Gly Gly Pro Asn Asp Thr Ala Val
    130                 135                 140

Pro Pro Leu Cys Thr Arg Thr His Ser Val Pro Gly Phe Leu Phe Ser
145                 150                 155                 160

Ser Gly Gly Phe Ala Gly Asn Leu Tyr His Asp Tyr Ala Asp Val Leu
                165                 170                 175

Val Pro Leu Phe Ala Ser Thr Asn His Leu Gly Gly Glu Val Gln Phe
            180                 185                 190

Leu Leu Ala Asp Ile Lys Asp Trp Trp Ala Asp Lys Phe Arg Pro Val
        195                 200                 205

Phe Arg Gln Leu Ser Arg Tyr Asp Val Ile Asp Val Asn Asn Asp Arg
    210                 215                 220

Glu Val His Cys Phe Pro Arg Thr Ile Ile Gly Ser Thr Phe His Arg
225                 230                 235                 240

Ala Met Gly Ile Asp Pro Ser Arg Ser Pro Gly Gly Val Thr Val Ala
                245                 250                 255

Asp Phe Lys Arg Leu Leu Arg Arg Ala Phe Arg Leu Glu Arg Ala Val
            260                 265                 270

Ala Ser Arg Ser Gly Ala Pro Arg Arg Asp Arg Pro Arg Leu Leu
        275                 280                 285

Ile Ile Ser Arg Lys Ser Ser Arg Arg Phe Val Asn Glu Arg Ala Met
    290                 295                 300

Ala Arg Ala Ala Ala Ala Arg Phe Asp Val Arg Ile Ala Glu Pro
305                 310                 315                 320

Asp Asn His Thr Asp Met Pro Asn Phe Ala Arg Leu Val Asn Ser Ala
                325                 330                 335

Asp Val Met Met Gly Val His Gly Ala Gly Leu Thr Asn Met Val Phe
            340                 345                 350

Leu Pro Ser Arg Ala Val Leu Val Gln Val Val Pro Phe Gly Gly Leu
        355                 360                 365

Glu Trp Leu Thr Arg Val Thr Phe Lys Asp Pro Ala Arg Asp Met Asp
    370                 375                 380

Val Thr Tyr Met Glu Tyr Asn Val Ser Leu Glu Glu Ser Ser Leu Arg
385                 390                 395                 400

Asp Leu Tyr Pro Glu Asp His Phe Tyr Leu Lys His Pro Tyr Asp Val
                405                 410                 415
```

```
His Lys Lys Gly Trp Asp Ala Ile Lys Thr Val Tyr Leu Asp Lys Gln
            420                 425                 430

Asn Val Arg Leu Asn Leu Thr Arg Phe Thr Arg Thr Leu Glu Gln Ala
            435                 440                 445

Arg Asp Leu Leu Pro Thr Pro
            450             455

<210> SEQ ID NO 3
<211> LENGTH: 1870
<212> TYPE: DNA
<213> ORGANISM: Zea mays

<400> SEQUENCE: 3
atgaagcagc cgaggggccg gcaggagccg cgccgggtgg gcaacgccgc catggtcgtc      60
accatggtcg tctccctctg cgtcctcacg tacatcaagg cgcgatactg ctccaaccct    120
ttccccaagg cggtggcgga ggtggaggtg acgaggact acgacagcac gcggtacaag     180
ctgacgggcc ccgtgggcga ggaggacttc gacccgtccc gccccacctg ctacaacacc    240
agcaagcggt cggagcggtg cgccgccgtg ggcgacatcc gcgtggacgg caaccactcg    300
cggatctaca tcagcccgct gtcccgcgag tggcggacca gccgtacgc gcggcggcac     360
gacgccgtgg ccatggacga cgtgcgcgag ttcacgctgg tccccttcgg cggccccaac    420
gacacggccg tgccgccgct ctgcacgcgc acccactccg tcccgggctt cctcttctcc    480
agcggcgggt cgcgggcaa cctgtaccac gactacgccg acgtgctggt ccgctcttc     540
gccagcacca accactgggg cggggaggtc cagttcctgc tggccgacat caaggactgg    600
tgggccgaca gttccgccc gctcttccgc cagctctccc gctacgacgt catcgacgtg    660
aacaacgacc gcgaggtgca ctgcttcccg cggatcatca tcggctccac cttccaccgc    720
gccatgggca tcgacccctc gcgctcgccc ggcggcgtca cggtggccga cttcaagcgc    780
ctgctccgcc gcgcgttccg gctggagcgc gccgtcgcgt cgcggtcggg ggcgccccgg    840
cgccgggacc ggccccgcct cctcatcatc tcgcgcaaga gctcgcgccg cttcgtcaac    900
gagcgcgcca tggcgcgcgc gcggcgcgcc gcccggttcg acgtgcggat cgccgagccc    960
gacaaccaca cggacatgcc caacttcgcg aggctggtga actcggcgga cgtgatgatg   1020
ggcgtgcacg cgccgggct caccaacatg gtgttcctgc ccagccgcgc cgtgctggtg    1080
caggtggtgc cgttcggcgg gctggagtgg ctcacccgcg tcaccttcaa ggaccccgca   1140
agggacgaga taattgccat tatggacgaa gagggaaggg gattcgacga aatgaaggcg   1200
ttggcgttgg cttctctgtt ttggagacgc acgcgacagc caaactccaa aacggatacg   1260
agacagctct tggggctgcg taaacaggga catggacgtc acgtacatgg agtacaacgt   1320
gtcgctggag gagagctcgc tcagggacct ctacccggag gaccacttct acctgaagca   1380
cccctacgac gtgcacaaga aggggtggga cgccatcaag acggtgtacc tggacaagca   1440
gaacgtcagg ctcaacctca ccaggttcac caggacgctg gagcaggcgc gagatctctt   1500
gccgacgcca tgactgatga tgacctcccc ctctttcctc tgctctgctg caggtttcat   1560
tcacttcaga tcagctgctc acctcacttc acgccgtgtc tctctctctt tttttttct    1620
gttgttgttc tatacatata cttgtttcct cttctccttt cccctctctc tctagtctct   1680
ccctctccac tcttgtggtg gcaagattca tttcttcat tgtttttgttt tttgttgttg   1740
ttgttgagga aggataggaa caaaaacaag gtattgtcgt gtccaaggtt aatctacaca   1800
aacacacact gtaaatgatt gattgattgc tgtcagtaga ggcgaacaca aggaataggt   1860
```
aaaaaaaaaa                                                              1870

<210> SEQ ID NO 4
<211> LENGTH: 605
<212> TYPE: PRT
<213> ORGANISM: Zea mays

<400> SEQUENCE: 4

Met Lys Gln Pro Arg Gly Arg Gln Glu Pro Arg Arg Val Gly Asn Ala
1               5                   10                  15

Ala Met Val Val Thr Met Val Val Ser Leu Cys Val Leu Thr Tyr Ile
            20                  25                  30

Lys Ala Arg Tyr Cys Ser Asn Pro Phe Pro Lys Ala Val Ala Glu Val
        35                  40                  45

Glu Val Asp Glu Asp Tyr Asp Ser Thr Arg Tyr Lys Leu Thr Gly Pro
    50                  55                  60

Val Gly Glu Glu Asp Phe Asp Pro Ser Arg Pro Thr Cys Tyr Asn Thr
65                  70                  75                  80

Ser Lys Arg Ser Glu Arg Cys Ala Ala Val Gly Asp Ile Arg Val Asp
                85                  90                  95

Gly Asn His Ser Arg Ile Tyr Ile Ser Pro Leu Ser Arg Glu Trp Arg
            100                 105                 110

Thr Lys Pro Tyr Ala Arg Arg His Asp Ala Val Ala Met Asp Asp Val
        115                 120                 125

Arg Glu Phe Thr Leu Val Pro Phe Gly Gly Pro Asn Asp Thr Ala Val
    130                 135                 140

Pro Pro Leu Cys Thr Arg Thr His Ser Val Pro Gly Phe Leu Phe Ser
145                 150                 155                 160

Ser Gly Gly Phe Ala Gly Asn Leu Tyr His Asp Tyr Ala Asp Val Leu
                165                 170                 175

Val Pro Leu Phe Ala Ser Thr Asn His Leu Gly Gly Glu Val Gln Phe
            180                 185                 190

Leu Leu Ala Asp Ile Lys Asp Trp Trp Ala Asp Lys Phe Arg Pro Leu
        195                 200                 205

Phe Arg Gln Leu Ser Arg Tyr Asp Val Ile Asp Val Asn Asn Asp Arg
    210                 215                 220

Glu Val His Cys Phe Pro Arg Ile Ile Ile Gly Ser Thr Phe His Arg
225                 230                 235                 240

Ala Met Gly Ile Asp Pro Ser Arg Ser Pro Gly Gly Val Thr Val Ala
                245                 250                 255

Asp Phe Lys Arg Leu Leu Arg Arg Ala Phe Arg Leu Glu Arg Ala Val
            260                 265                 270

Ala Ser Arg Ser Gly Ala Pro Arg Arg Asp Arg Pro Arg Leu Leu
        275                 280                 285

Ile Ile Ser Arg Lys Ser Ser Arg Arg Phe Val Asn Glu Arg Ala Met
    290                 295                 300

Ala Arg Ala Ala Ala Ala Arg Phe Asp Val Arg Ile Ala Glu Pro
305                 310                 315                 320

Asp Asn His Thr Asp Met Pro Asn Phe Ala Arg Leu Val Asn Ser Ala
                325                 330                 335

Asp Val Met Met Gly Val His Gly Ala Gly Leu Thr Asn Met Val Phe
            340                 345                 350

Leu Pro Ser Arg Ala Val Leu Val Gln Val Val Pro Phe Gly Gly Leu
        355                 360                 365

```
Glu Trp Leu Thr Arg Val Thr Phe Lys Asp Pro Ala Arg Asp Glu Ile
        370                 375                 380

Ile Ala Ile Met Asp Glu Gly Arg Gly Phe Asp Glu Met Glu Ala
385                 390                 395                 400

Leu Ala Leu Ala Ser Leu Phe Trp Arg Thr Arg Gln Pro Asn Ser
                405                 410                 415

Lys Thr Asp Thr Arg Gln Leu Leu Gly Leu Arg Lys Gln Gly His Gly
                420                 425                 430

Arg His Val His Gly Val Gln Arg Val Ala Gly Gly Glu Leu Ala Gln
            435                 440                 445

Gly Pro Leu Pro Gly Gly Pro Leu Leu Pro Glu Ala Pro Leu Arg Arg
    450                 455                 460

Ala Gln Glu Gly Val Gly Arg His Gln Asp Gly Val Pro Gly Gln Ala
465                 470                 475                 480

Glu Arg Gln Ala Gln Pro His Gln Val His Gln Asp Ala Gly Ala Gly
                485                 490                 495

Ala Arg Ser Leu Ala Asp Ala Met Thr Asp Asp Leu Pro Leu Phe
                500                 505                 510

Pro Leu Leu Cys Cys Arg Phe His Ser Leu Gln Ile Ser Cys Ser Pro
        515                 520                 525

His Phe Thr Pro Cys Leu Ser Leu Phe Phe Phe Ser Val Val Leu
    530                 535                 540

Tyr Ile Tyr Leu Phe Pro Leu Leu Leu Ser Pro Leu Ser Leu Val Ser
545                 550                 555                 560

Pro Ser Pro Leu Leu Trp Trp Gln Asp Ser Phe Leu Ser Leu Phe Cys
                565                 570                 575

Phe Leu Leu Leu Leu Leu Arg Lys Asp Arg Asn Lys Asn Lys Val Leu
                580                 585                 590

Ser Cys Pro Arg Leu Ile Tyr Thr Asn Thr His Cys Lys
        595                 600                 605

<210> SEQ ID NO 5
<211> LENGTH: 1725
<212> TYPE: DNA
<213> ORGANISM: Zea mays

<400> SEQUENCE: 5
atgaagcagc cgaggggccg gcaggagccg cgccgggtgg gcaacgccgc catggtcgtc      60
accatggtcg tctccctctg cgtcctcacg tacatcaagg cgcgatactg ctccaaccct    120
ttccccaagg cggtggcgga ggtggaggtg gacgaggact acgacagcac gcggtacaag    180
ctgacgggcc ccgtgggcga ggaggacttc gacccgtccc gccccacctg ctacaacacc    240
agcaagcggt cggagcggtg cgccgccgtg ggcgacatcc gcgtggacgg caaccactcg    300
cggatctaca tcagcccgct gtcccgcgag tggcggacca gccgtacgc gcggcggcac    360 gacgccgtgg ccatgacga cgtgcgcgag ttcacgctgg tccccttcgg cggccccaac    420
gacacggccg tgccgccgct ctgcacgcgc acccactccg tcccgggctt cctcttctcc    480
agcggcgggt cgcgggcaa cctgtaccac gactacgccg acgtgctggt gccgctcttc    540
gccagcacca accacctggg cggggaggtc cagttcctgc tggccgacat caaggactgg    600
tgggccgaca gttccgcccc gctcttccgc cagctctccc gctacgacgt catcgacgtg    660
aacaacgacc gcgaggtgca ctgcttcccg cggatcatca tcggctccac cttccaccgc    720
gccatgggca tcgacccctc gcgctcgccc ggcggcgtca cggtggccga cttcaagcgc    780
```

```
ctgctccgcc gcgcgttccg gctggagcgc gccgtcgcgt cgcggtcggg ggcgccccgg      840
cgccgggacc ggccccgcct cctcatcatc tcgtgcaaga gctcgcgccg cttcgtcaac      900
gagcgcgcca tggcgcgcgc cgcggcggcc gcccggttcg acgtgcggat cgccgagccc      960
gacaaccaca cggacatgcc caacttcgcg aggctggtga actcggcgga cgtgatgatg     1020
ggcgtgcacg gcgccgggct caccaacatg gtgttcctgc ccagccgcgc cgtgctggtg     1080
caggtggtgc cgttcggcgg gctggagtgg ctcacccgcg tcaccttcaa ggaccccgca     1140
agggacatgg acgtcacgta catggagtac aacgtgtcgc tggaggagag ctcgctcagg     1200
gacctctacc cggaggacca cttctacctg aagcacccct acgacgtgca caagaagggg     1260
tgggacgcca tcaagacggt gtacctggac aagcagaacg tcaggctcaa cctcaccagg     1320
ttcaccagga cgctggagca ggcgcgagat ctcttgccga cgccatgact gatgatgacc     1380
tcccctctt tcctctgctc tgctgcaggt tcattcact tcagatcagc tgctcacctc       1440
acttcacgcc gtgtctctct ctcttttttt tttctgttgt tgttctatac atatacttgt     1500
ttcctcttct cctttcccct ctctctctag tctctccctc tccactcttg tggtggcaag     1560
attcatttct ttcattgttt tgttttttgt tgttgttgtt gaggaaggat aggaacaaaa     1620
acaaggtatt gtcgtgtcca aggttaatct acacaaacac acactgtaaa tgattgattg     1680
attgctgtca gtagaggcga acacaaggaa taggtaaaaa aaaaa                     1725

<210> SEQ ID NO 6
<211> LENGTH: 455
<212> TYPE: PRT
<213> ORGANISM: Zea mays

<400> SEQUENCE: 6

Met Lys Gln Pro Arg Gly Arg Gln Glu Pro Arg Val Gly Asn Ala
1               5                   10                  15

Ala Met Val Val Thr Met Val Val Ser Leu Cys Val Leu Thr Tyr Ile
            20                  25                  30

Lys Ala Arg Tyr Cys Ser Asn Pro Phe Pro Lys Ala Val Ala Glu Val
        35                  40                  45

Glu Val Asp Glu Asp Tyr Asp Ser Thr Arg Tyr Lys Leu Thr Gly Pro
    50                  55                  60

Val Gly Glu Glu Asp Phe Asp Pro Ser Arg Pro Thr Cys Tyr Asn Thr
65                  70                  75                  80

Ser Lys Arg Ser Glu Arg Cys Ala Ala Val Gly Asp Ile Arg Val Asp
                85                  90                  95

Gly Asn His Ser Arg Ile Tyr Ile Ser Pro Leu Ser Arg Glu Trp Arg
            100                 105                 110

Thr Lys Pro Tyr Ala Arg Arg His Asp Ala Val Ala Met Asp Asp Val
        115                 120                 125

Arg Glu Phe Thr Leu Val Pro Phe Gly Gly Pro Asn Asp Thr Ala Val
    130                 135                 140

Pro Pro Leu Cys Thr Arg Thr His Ser Val Pro Gly Phe Leu Phe Ser
145                 150                 155                 160

Ser Gly Gly Phe Ala Gly Asn Leu Tyr His Asp Tyr Ala Asp Val Leu
                165                 170                 175

Val Pro Leu Phe Ala Ser Thr Asn His Leu Gly Gly Glu Val Gln Phe
            180                 185                 190

Leu Leu Ala Asp Ile Lys Asp Trp Trp Ala Asp Lys Phe Arg Pro Val
        195                 200                 205
```

```
Phe Arg Gln Leu Ser Arg Tyr Asp Val Ile Asp Val Asn Asn Asp Arg
            210                 215                 220

Glu Val His Cys Phe Pro Arg Thr Ile Ile Gly Ser Thr Phe His Arg
225                 230                 235                 240

Ala Met Gly Ile Asp Pro Ser Arg Ser Pro Gly Gly Val Thr Val Ala
                245                 250                 255

Asp Phe Lys Arg Leu Leu Arg Arg Ala Phe Arg Leu Glu Arg Ala Val
                260                 265                 270

Ala Ser Arg Ser Gly Ala Pro Arg Arg Asp Arg Pro Arg Leu Leu
            275                 280                 285

Ile Ile Ser Cys Lys Ser Ser Arg Arg Phe Val Asn Glu Arg Ala Met
            290                 295                 300

Ala Arg Ala Ala Ala Ala Arg Phe Asp Val Arg Ile Ala Glu Pro
305                 310                 315                 320

Asp Asn His Thr Asp Met Pro Asn Phe Ala Arg Leu Val Asn Ser Ala
                325                 330                 335

Asp Val Met Met Gly Val His Gly Ala Gly Leu Thr Asn Met Val Phe
                340                 345                 350

Leu Pro Ser Arg Ala Val Leu Val Gln Val Val Pro Phe Gly Gly Leu
            355                 360                 365

Glu Trp Leu Thr Arg Val Thr Phe Lys Asp Pro Ala Arg Asp Met Asp
370                 375                 380

Val Thr Tyr Met Glu Tyr Asn Val Ser Leu Glu Glu Ser Ser Leu Arg
385                 390                 395                 400

Asp Leu Tyr Pro Glu Asp His Phe Tyr Leu Lys His Pro Tyr Asp Val
                405                 410                 415

His Lys Lys Gly Trp Asp Ala Ile Lys Thr Val Tyr Leu Asp Lys Gln
            420                 425                 430

Asn Val Arg Leu Asn Leu Thr Arg Phe Thr Arg Thr Leu Glu Gln Ala
            435                 440                 445

Arg Asp Leu Leu Pro Thr Pro
        450                 455

<210> SEQ ID NO 7
<211> LENGTH: 488
<212> TYPE: PRT
<213> ORGANISM: Zea mays

<400> SEQUENCE: 7

Met Lys Ser Ser Leu Arg Ser Arg Gln Glu Pro Arg Arg Val Ser Asn
1               5                   10                  15

Gly Val Ile Ile Gly Ala Met Leu Leu Ser Leu Cys Val Leu Ser Ile
                20                  25                  30

Val Lys Ala Arg Tyr Cys Ala Thr Pro Phe Gly Lys Ala Glu Asp Gln
            35                  40                  45

Leu Gln Glu Gln Met Asn Ser Ser Ile Arg Met Glu Pro Glu Glu Ser
        50                  55                  60

Ser Pro Ala Arg Thr Pro Gly Glu Glu Glu Glu Asp Asp Gly Glu
65                  70                  75                  80

Asn Gly Ala Ser Ala Thr Thr Thr Thr Ala Pro Ala Val Thr Lys Thr
                85                  90                  95

Pro Ala Ala Val Ala Ala Gly Gly Asn Arg Gly Lys Gly Lys Pro Thr
            100                 105                 110

Cys Tyr Met Thr Ser Lys Arg Ser Glu Arg Cys Asp Ala Ser Gly Asp
```

```
                115                 120                 125
Ile Arg Val Asp Gly Asn Arg Ser Thr Ile Tyr Val Ser Gly Ile Asp
130                 135                 140

Arg Glu Trp Lys Thr Lys Pro Tyr Ala Arg Tyr His Asp Pro Val Ala
145                 150                 155                 160

Met Ala His Val Arg Glu Tyr Thr Leu Lys Pro Leu Pro Glu Ala Ala
                165                 170                 175

Pro Ala Pro Ala Cys Thr Arg Asn His Ser Val Pro Gly Phe Leu Phe
            180                 185                 190

Ser Asn Gly Gly Phe Ser Gly Asn Leu Tyr His Asp Tyr Thr Asp Val
        195                 200                 205

Leu Val Pro Leu Phe Ile Ser Thr His Gln Phe Arg Gly Arg Val Gln
    210                 215                 220

Phe Leu Leu Ser Gly Met Lys Pro Trp Trp Val Ala Lys Phe Thr Pro
225                 230                 235                 240

Phe Phe Arg Gln Leu Thr Arg Tyr Asp Val Ile Asp Val Asp Asn Asp
                245                 250                 255

Gln Glu Val His Cys Phe Pro Arg Ile Val Gly Ala Thr Phe His
            260                 265                 270

Lys Asp Met Gly Val Asp Pro Arg Arg Ser Pro Gly His Val Ser Val
        275                 280                 285

Val Asp Phe Lys Arg Ala Leu Arg Arg Ala Phe Gly Leu Pro Arg Glu
    290                 295                 300

Ala Ala Ser Arg Gly Gly Ala Thr Gly Arg Gly Lys Pro Arg Leu Leu
305                 310                 315                 320

Ile Ile Ser Arg Arg Gly Ser Arg Arg Phe Leu Asn Glu Arg Glu Met
                325                 330                 335

Ala Arg Ala Ala Ala Gly Ala Gly Phe Glu Val Arg Val Ala Glu Pro
            340                 345                 350

Asp Gln His Thr Asp Thr Ala Ala Phe Ala Ala Leu Val Asn Ser Ala
        355                 360                 365

Asp Val Met Val Gly Val His Gly Ala Gly Leu Thr Asn Met Val Phe
    370                 375                 380

Leu Pro Arg Gly Ala Val Leu Val Gln Val Val Pro Phe Gly Gly Leu
385                 390                 395                 400

Glu Trp Leu Thr Gly Val Thr Phe Lys Asp Pro Ala Ala Asp Met Glu
                405                 410                 415

Val Ser Tyr Met Gly Tyr Asp Val Thr Leu Glu Glu Ser Ser Leu Ile
            420                 425                 430

Asp Gln Tyr Pro Arg Asn His Gln Val Leu Thr Asp Pro Tyr Ala Val
        435                 440                 445

His Lys Gln Gly Trp Asp Ala Leu Lys Ala Ala Tyr Leu Asp Lys Gln
    450                 455                 460

Asn Ile Arg Met Asp Leu Asp Arg Phe Arg Ala Thr Leu Arg Glu Ala
465                 470                 475                 480

Met Ser Arg Leu Pro Pro Ala Pro
                485

<210> SEQ ID NO 8
<211> LENGTH: 491
<212> TYPE: PRT
<213> ORGANISM: Zea mays

<400> SEQUENCE: 8
```

-continued

```
Met Lys Ser Ser Leu Arg Ser Arg Gln Glu Ser Arg Arg Val Ser Asn
  1               5                  10                  15

Gly Val Ile Ile Gly Ala Met Leu Leu Ser Leu Cys Val Leu Ser Phe
             20                  25                  30

Val Lys Ala Arg Tyr Cys Ala Thr Pro Leu Gly Lys Ala Glu Asp Gln
         35                  40                  45

Leu Glu Glu Gln Met Asn Ala Ser Ile Arg Met Glu Pro Glu Glu Ser
     50                  55                  60

Ser Pro Ala Arg Thr Pro Gly Glu Glu Asp Glu Gln Glu Ala Glu
 65                  70                  75                  80

Glu Glu Asn Val Val Thr Lys Pro Pro Pro Pro Ala Val Thr
                 85                  90                  95

Ala Asn Arg Gly Ser Lys Lys Lys Gly Lys Gly Lys Pro Thr Cys
                100                 105                 110

Tyr Met Thr Ser Lys Arg Ser Glu Arg Cys Asp Ala Ser Gly Asp Ile
            115                 120                 125

Arg Val Asp Gly Asn Arg Ser Thr Ile Tyr Val Gly Gly Ile Glu Arg
        130                 135                 140

Glu Trp Arg Thr Lys Pro Tyr Ala Arg Tyr His Asp Pro Val Ala Met
145                 150                 155                 160

Ala His Val Arg Glu Tyr Thr Leu Lys Ala Leu Pro Glu Pro Gly Ala
                165                 170                 175

Ala Ala Ala Pro Ala Cys Thr Arg Asn His Ser Val Pro Gly Phe Leu
            180                 185                 190

Phe Ser Asn Gly Gly Phe Ser Gly Asn Leu Tyr His Asp Tyr Thr Asp
        195                 200                 205

Val Leu Val Pro Leu Phe Ile Ser Thr His Gln Phe Arg Gly Arg Val
    210                 215                 220

Gln Phe Leu Val Ser Gly Met Lys Pro Trp Trp Val Gly Lys Phe Thr
225                 230                 235                 240

Pro Phe Phe Arg Gln Leu Thr Arg His Asp Val Ile Asp Val Asp Lys
                245                 250                 255

Asp Gly Glu Val His Cys Phe Pro Arg Ile Val Val Gly Ala Thr Phe
            260                 265                 270

His Arg Asp Met Gly Val Asp Pro Arg Ala Pro Gly His Val Ser
        275                 280                 285

Ala Val Asp Phe Lys Arg Ala Leu Arg Ala Ala Phe Gly Leu Lys Arg
    290                 295                 300

Glu Ala Ala Ser Arg Gly Gly Gly Gly Ala Thr Gly Asp Gly Lys
305                 310                 315                 320

Pro Arg Leu Leu Ile Ile Ser Arg Arg Gly Ser Arg Arg Phe Leu Asn
                325                 330                 335

Ser Arg Glu Met Ala Val Ala Ala Gly Asp Ala Gly Phe Glu Val Arg
            340                 345                 350

Val Ala Glu Pro Asp Gln Arg Thr Asp Met Ala Ala Phe Ala Ala Leu
        355                 360                 365

Val Asn Ser Ala Asp Ala Met Val Gly Val His Gly Ala Gly Leu Thr
    370                 375                 380

Asn Met Val Phe Leu Pro Arg Gly Ala Val Leu Val Gln Val Val Pro
385                 390                 395                 400

Phe Gly Gly Leu Glu Trp Leu Thr Gly Val Thr Phe Lys Glu Pro Ala
                405                 410                 415

Ala Asp Met Glu Val Ser Tyr Met Asp Tyr His Val Arg Leu Glu Glu
```

```
              420             425             430
Ser Ser Leu Val Asp Gln Tyr Pro Arg Gly His Gln Val Leu Thr Asp
        435                 440                 445

Pro Tyr Ala Val His Arg Gln Gly Trp Asp Ala Leu Lys Thr Ala Tyr
    450                 455                 460

Leu Asp Lys Gln Asn Ile Arg Met Asp Leu Asp Arg Phe Arg Ala Thr
465                 470                 475                 480

Leu Arg Glu Val Met Ala Arg Leu Pro Ser Pro
                485                 490

<210> SEQ ID NO 9
<211> LENGTH: 460
<212> TYPE: PRT
<213> ORGANISM: Oryza sativa

<400> SEQUENCE: 9

Met Lys His His His Val Ala Arg Gly Arg Ala Glu Pro Arg Arg Met
1               5                   10                  15

Gly Asn Ala Ala Met Val Ile Thr Met Leu Leu Ser Leu Cys Val Leu
                20                  25                  30

Thr Tyr Ile Lys Ala Arg Tyr Cys Ser Thr Pro Phe Pro Lys Ala Ala
            35                  40                  45

Glu Glu Met Glu Val Val Glu Ile Asp Glu Asp Tyr Asp Ser Thr Arg
        50                  55                  60

Tyr Lys Met Thr Gly Pro Ile Gly Glu Glu Asp Phe Asp Pro Thr Arg
65                  70                  75                  80

Pro Thr Cys Tyr Val Thr Ser Lys Arg Ser Glu Arg Cys Ala Ala Val
                85                  90                  95

Gly Asp Ile Arg Val Asp Gly Asn His Ser Lys Ile Tyr Ile Asn Pro
            100                 105                 110

Leu Asp Lys Glu Trp Arg Thr Lys Pro Tyr Ala Arg Leu His Asp Ala
        115                 120                 125

Val Ala Met Asp Asp Val Arg Glu Phe Thr Leu Val Pro Phe Gly Gly
130                 135                 140

Ala Asn His Thr Ala Val Pro Pro Leu Cys Thr Arg Asn His Ser Val
145                 150                 155                 160

Pro Ala Phe Leu Phe Ser Ser Gly Gly Phe Ala Gly Asn Leu Tyr His
                165                 170                 175

Asp Tyr Thr Asp Val Leu Val Pro Leu Phe Thr Ser Thr Asn His Phe
            180                 185                 190

Gly Gly Glu Val Gln Phe Leu Leu Ser Gly Ile Lys Asp Trp Trp Leu
        195                 200                 205

Asp Lys Phe Thr Pro Leu Phe Arg Gln Leu Ser Arg Tyr Asp Val Ile
210                 215                 220

Asp Val Asp Asn Asp Gln Glu Val His Cys Phe Pro Arg Ile Phe Ile
225                 230                 235                 240

Gly Ala Thr Phe His Arg Ala Met Gly Ile Asp Pro Ala Arg Ser Pro
                245                 250                 255

Gly Gly Val Thr Val Ala Asp Phe Lys Arg Leu Leu Arg Arg Thr Phe
            260                 265                 270

Arg Leu Glu Arg Ala Val Ala Ser Arg Thr Gly Ala Pro Arg Arg Asp
        275                 280                 285

Lys Pro Arg Leu Leu Ile Ile Ser Arg Lys Ser Ser Arg Arg Phe Leu
        290                 295                 300
```

```
Asn Glu Arg Ala Met Ala His Ala Ala Leu Ala Arg Phe Asp Val
305                 310                 315                 320

Arg Ile Ala Glu Pro Asp Asn His Thr Asp Met Pro Asn Phe Ala Arg
            325                 330                 335

Leu Val Asn Ser Ala Asp Val Met Met Gly Val His Gly Ala Gly Leu
        340                 345                 350

Thr Asn Met Val Phe Leu Pro Ser Arg Ala Val Leu Ile Gln Val Val
    355                 360                 365

Pro Phe Gly Gly Leu Glu Trp Leu Thr Arg Val Thr Phe Lys Asp Pro
370                 375                 380

Ala Lys Asp Met Asp Val Asn Tyr Met Glu Tyr Asn Val Ser Phe Asp
385                 390                 395                 400

Glu Ser Ser Leu Arg Glu Leu Tyr Pro Arg Asp His Phe Tyr Ile Gln
            405                 410                 415

His Pro Tyr Asp Val His Lys Lys Gly Trp Asp Ala Ile Lys Thr Val
        420                 425                 430

Tyr Leu Asp Lys Gln Asn Val Glu Leu Asn Leu Thr Lys Leu Thr Asn
    435                 440                 445

Thr Leu Glu Arg Ala Arg Asp Phe Leu Pro Glu Pro
450                 455                 460

<210> SEQ ID NO 10
<211> LENGTH: 485
<212> TYPE: PRT
<213> ORGANISM: Oryza sativa

<400> SEQUENCE: 10

Met Lys Gln Ser Met Arg Ser Arg Gln Glu Pro Arg Arg Val Ser Asn
1               5                   10                  15

Gly Val Ile Ile Ala Ala Met Leu Leu Ser Leu Cys Val Leu Ser Ile
            20                  25                  30

Val Lys Ala Arg Tyr Cys Ser Thr Pro Phe Val Lys Pro Asp Asp Gln
        35                  40                  45

Leu Gln Glu Gln Met Asn Ser Ser Ile Arg Met Glu Thr Asp Glu Pro
    50                  55                  60

Ala Thr Met Ala Ala Gly Glu Gln Glu Asp Glu Glu Glu Glu Glu Ser
65                  70                  75                  80

Ser Gly Gly Gly Ala Glu Pro Glu Val Ser Ala Thr Pro Ala Val
            85                  90                  95

Val Val Thr Ala Ala Ala Gly Gly Gly Gly Lys Arg Lys Pro Thr
        100                 105                 110

Cys Arg Met Thr Ser Lys Arg Ser Glu Arg Cys Glu Ala Arg Gly Asp
    115                 120                 125

Ile Arg Val Glu Gly Asn Ala Ser Thr Ile Tyr Ile Gly Gly Ile Asp
130                 135                 140

Lys Glu Trp Lys Thr Lys Pro Tyr Ala Arg Tyr His Asp Pro Val Ala
145                 150                 155                 160

Met Ala Val Val Arg Glu Phe Thr Leu Lys Pro Val Thr Glu Ser Ser
            165                 170                 175

Pro Ala Cys Thr Arg Asn His Ser Val Pro Ala Phe Val Phe Ser Asn
        180                 185                 190

Gly Gly Phe Ser Gly Asn Leu Tyr His Asp Tyr Thr Asp Val Leu Val
    195                 200                 205

Pro Leu Phe Leu Ser Thr His Gln Phe Lys Gly Gln Val Gln Phe Leu
210                 215                 220
```

-continued

```
Leu Ser Gly Leu Lys Pro Trp Trp Val Asn Lys Phe Asn Leu Phe
225                 230                 235                 240

Arg Gln Leu Thr Lys Tyr Asp Ile Leu Asp Ile Asp Asn Asp Lys Asp
            245                 250                 255

Val His Cys Phe Pro Arg Ile Val Val Gly Ala Thr Phe His Lys Asp
        260                 265                 270

Met Gly Val Asp Pro Lys Arg Ser Pro Gly His Val Ser Val Val Asp
    275                 280                 285

Phe Lys Arg Ala Leu Arg Arg Ala Phe Gly Leu Glu Arg Val Ala Ala
290                 295                 300

Ser Arg Gly Gly Ala Thr Gly Asn Gly Lys Pro Arg Leu Leu Ile Ile
305                 310                 315                 320

Ser Arg Lys Asn Ser Arg Arg Phe Leu Asn Glu Arg Glu Met Ala Gln
            325                 330                 335

Ala Ala Ala Ala Val Gly Phe Glu Val Arg Ile Ala Glu Pro Asp Gln
        340                 345                 350

His Thr Asp Met Ser Thr Phe Ala Gln Leu Val Asn Ser Ala Asp Val
    355                 360                 365

Met Ile Gly Val His Gly Ala Gly Leu Thr Asn Met Val Phe Leu Pro
370                 375                 380

Arg Gly Ala Val Leu Ile Gln Val Val Pro Phe Gly Gly Leu Glu Trp
385                 390                 395                 400

Leu Thr Thr Val Thr Phe Lys Asn Pro Ala Lys Asp Met Glu Val Thr
            405                 410                 415

Tyr Met Asp Tyr Asn Val Gln Leu Glu Ser Ser Leu Ile Asp Gln
        420                 425                 430

Tyr Pro Arg Asn His Gln Val Leu Thr Asp Pro Tyr Ala Val His Lys
    435                 440                 445

Gln Gly Trp Asp Ala Leu Lys Thr Ala Tyr Leu Asp Lys Gln Asn Ile
450                 455                 460

Lys Met Asp Met Asp Arg Phe Lys Lys Thr Leu Gln Glu Ala Leu Asp
465                 470                 475                 480

Arg Leu Pro Pro Ala
            485

<210> SEQ ID NO 11
<211> LENGTH: 462
<212> TYPE: PRT
<213> ORGANISM: Sorghum bicolor

<400> SEQUENCE: 11

Met Thr Met Lys Gln Pro Arg Gly Arg Gln Glu Pro Arg Arg Met Gly
1               5                   10                  15

Asn Ala Ala Met Val Val Thr Met Leu Val Ser Leu Cys Val Leu Thr
            20                  25                  30

Tyr Ile Lys Ala Arg Tyr Cys Ser Asn Pro Phe Pro Lys Pro Ala Glu
        35                  40                  45

Glu Leu Glu Val Val Glu Val Asp Glu Asp Tyr Asp Ser Thr Arg Tyr
    50                  55                  60

Lys Leu Ser Gly Pro Ile Gly Glu Glu Asp Phe Asp Pro Ser Arg Pro
65                  70                  75                  80

Thr Cys Tyr Asn Thr Ser Lys Arg Ser Glu Arg Cys Ala Ala Val Gly
            85                  90                  95

Asp Ile Arg Val Asp Gly Asn His Ser Arg Ile Tyr Ile Ser Pro Leu
```

```
            100                 105                 110
Ser Arg Glu Trp Lys Thr Lys Pro Tyr Ala Arg Leu His Asp Pro Val
            115                 120                 125

Ala Met Asp Asp Val Arg Glu Phe Thr Leu Val Pro Phe Gly Pro Gly
            130                 135                 140

Ser Pro Asn Gly Thr Val Val Pro Pro Leu Cys Thr Arg Asn His Ser
145                 150                 155                 160

Val Pro Gly Phe Leu Phe Ser Ser Gly Gly Phe Ala Gly Asn Leu Tyr
                165                 170                 175

His Asp Tyr Ala Asp Val Leu Val Pro Leu Phe Ala Ser Thr His His
            180                 185                 190

Phe Gly Gly Glu Val Gln Phe Leu Leu Ala Asp Ile Lys Asp Trp Trp
            195                 200                 205

Ala Asp Lys Phe Lys Pro Leu Phe Arg Gln Leu Ser Arg Tyr Asp Val
            210                 215                 220

Ile Asp Val Asn Asn Asp Arg Glu Val His Cys Phe Pro Arg Ile Val
225                 230                 235                 240

Ile Gly Ser Thr Phe His Arg Ala Met Gly Ile Asp Ala Ser Arg Ser
                245                 250                 255

Pro Gly Gly Glu Thr Val Ala Asp Phe Lys Arg Val Leu Arg Arg Ala
                260                 265                 270

Phe Lys Leu Glu Arg Ala Val Ala Ser Arg Ser Gly Ala Pro Arg Arg
            275                 280                 285

Lys Asp Arg Pro Arg Leu Leu Ile Ile Ser Lys Ser Ser Arg Arg
            290                 295                 300

Phe Val Asn Glu Arg Ala Met Ala Arg Ala Ala Ala Ala Lys Phe
305                 310                 315                 320

Asp Val Arg Ile Ala Glu Pro Asp Asn His Thr Asp Met Pro Asn Phe
                325                 330                 335

Ala Arg Leu Val Asn Ser Ala Asp Val Met Met Gly Val His Gly Ala
            340                 345                 350

Gly Leu Thr Asn Met Val Phe Leu Pro Ser Arg Ala Val Leu Val Gln
            355                 360                 365

Val Val Pro Phe Gly Gly Leu Glu Trp Leu Thr Arg Val Thr Phe Lys
            370                 375                 380

Asp Pro Ala Arg Asp Met Asp Val Thr Tyr Met Glu Tyr Asn Val Ser
385                 390                 395                 400

Leu Glu Glu Ser Ser Leu Arg Asp Leu Tyr Pro Glu Asp His Phe Tyr
                405                 410                 415

Leu Lys His Pro Tyr Asp Val His Lys Lys Gly Trp Asp Ala Ile Lys
            420                 425                 430

Thr Val Tyr Leu Asp Lys Gln Asn Val Arg Leu Asn Leu Thr Arg Phe
            435                 440                 445

Thr Arg Thr Leu Glu Gln Ala Arg Asp Leu Leu Pro Ser Pro
450                 455                 460

<210> SEQ ID NO 12
<211> LENGTH: 499
<212> TYPE: PRT
<213> ORGANISM: Sorghum bicolor

<400> SEQUENCE: 12

Met Lys Ser Ser Leu Arg Thr Arg Gln Glu Pro Arg Arg Val Ser Asn
1               5                   10                  15
```

-continued

Gly Val Ile Ile Gly Ala Met Leu Leu Ser Leu Cys Val Leu Ser Ile
              20                  25                  30

Val Lys Ala Arg Tyr Cys Ala Thr Pro Phe Gly Lys Ala Glu Asp Gln
          35                  40                  45

Leu Gln Glu Gln Met Asn Ser Ser Ile Arg Met Glu Pro Glu Glu Ser
     50                   55                  60

Ser Pro Ala Arg Thr Pro Gly Glu Glu Asp Glu Gln Glu Glu Glu
65                   70                  75                  80

Glu Glu Glu Asn Gly Ala Ser Ala Thr Pro Ala Thr Thr Ala Pro
                  85                  90                  95

Ala Val Thr Lys Thr Thr Pro Thr Ala Val Pro Ala Thr Ala Gly Asn
              100                 105                 110

Arg Gly Lys Val Ser Lys Gly Gly Lys Gly Lys Pro Thr Cys Tyr Met
          115                 120                 125

Thr Ser Lys Arg Ser Glu Arg Cys Asp Ala Ser Gly Asp Ile Arg Val
     130                 135                 140

Asp Gly Asn Arg Ser Ala Ile Tyr Val Ser Gly Ile Asp Lys Glu Trp
145                 150                 155                 160

Lys Thr Lys Pro Tyr Ala Arg Tyr His Asp Pro Val Ala Met Ala His
                  165                 170                 175

Val Arg Glu Tyr Thr Leu Lys Pro Leu Pro Ala Ala Glu Ala Pro Ala
              180                 185                 190

Cys Thr Arg Asn His Ser Val Pro Gly Phe Leu Phe Ser Asn Gly Gly
          195                 200                 205

Phe Ser Gly Asn Leu Tyr His Asp Tyr Thr Asp Val Leu Val Pro Leu
210                 215                 220

Phe Ile Ser Thr His Gln Phe Arg Gly Arg Val Gln Phe Leu Leu Ser
225                 230                 235                 240

Gly Met Lys Pro Trp Trp Val Ala Lys Phe Thr Pro Phe Phe Arg Gln
                  245                 250                 255

Leu Thr Lys Tyr Asp Val Ile Asp Val Asp Asn Asp Gln Glu Val His
              260                 265                 270

Cys Phe Pro Arg Ile Val Ala Gly Ala Thr Phe His Lys Asp Met Gly
          275                 280                 285

Val Asp Pro Arg Arg Ser Pro Gly His Val Ser Val Asp Phe Lys
     290                 295                 300

Arg Ala Leu Arg Arg Ala Phe Gly Leu Glu Arg Glu Ala Ala Ser Arg
305                 310                 315                 320

Gly Gly Ala Thr Gly His Gly Lys Pro Arg Leu Leu Ile Ile Ser Arg
                  325                 330                 335

Arg Gly Ser Arg Arg Phe Leu Asn Glu Arg Glu Met Ala Arg Ala Ala
              340                 345                 350

Ala Asp Ala Gly Phe Glu Val Arg Val Ala Glu Pro Asp Gln His Thr
          355                 360                 365

Asp Met Ala Thr Phe Ala Ala Leu Val Asn Ser Ala Asp Val Met Val
370                 375                 380

Gly Val His Gly Ala Gly Leu Thr Asn Met Val Phe Leu Pro Arg Gly
385                 390                 395                 400

Ala Val Leu Ile Gln Val Pro Phe Gly Gly Leu Glu Trp Leu Thr
                  405                 410                 415

Ser Val Thr Phe Lys Asp Pro Ala Ala Asp Met Glu Val Asn Tyr Met
              420                 425                 430

Asp Tyr Asn Val Lys Leu Glu Glu Ser Ser Leu Leu Asp Gln Tyr Pro

```
                    435                 440                 445
Arg Asn His Gln Val Leu Thr Asp Pro Tyr Ala Val His Lys Gln Gly
    450                 455                 460

Trp Asp Ala Leu Lys Thr Ala Tyr Leu Asp Lys Gln Asn Ile Arg Met
465                 470                 475                 480

Asp Leu Asp Arg Phe Arg Ala Thr Leu Arg Glu Ala Met Ser Arg Leu
                485                 490                 495

Pro Ser Pro

<210> SEQ ID NO 13
<211> LENGTH: 452
<212> TYPE: PRT
<213> ORGANISM: Glycine max

<400> SEQUENCE: 13

Met Ile Tyr Asp Thr Val Leu Ala Lys Ser Phe Ser Arg Tyr Asp Gln
1               5                   10                  15

Lys Arg Leu Gly Tyr Gly Ala Phe Val Ser Cys Leu Leu Ile Val Leu
                20                  25                  30

Met Leu Leu His Pro Leu Ala Leu Ile Thr Tyr Phe His Asn Pro Arg
            35                  40                  45

Pro Ser Thr Ser Ile His Cys Ala Leu Val Ile Gly Ile Lys Cys Arg
        50                  55                  60

Tyr Ile Phe His His Phe Glu Leu Leu Cys Thr Ser Glu Glu Arg Thr
65                  70                  75                  80

Lys Phe Cys Gln Ala Arg Gly Asp Ile Arg Val His Gly Lys Ser Ser
                85                  90                  95

Thr Val Tyr Ile Val Ser Ser Lys Thr Thr Met Ser Glu Lys Asn Met
            100                 105                 110

Ser Trp Asn Leu Lys Pro Tyr Ala Arg Arg Asp Asp Val Asp Ala Met
        115                 120                 125

Ile Arg Val Arg Glu Trp Ser Val Lys Ala Val Asn Val Ser Gln Lys
    130                 135                 140

Ala Pro Gln Cys Thr Gln Tyr His Asn Ile Pro Ala Val Leu Phe Ser
145                 150                 155                 160

Thr Gly Gly Tyr Ala Gly Asn His Phe His Glu Phe Thr Asp Ile Val
                165                 170                 175

Ile Pro Leu Phe Leu Thr Ala Arg Gln Phe Asn Gly Glu Val Gln Phe
            180                 185                 190

Ile Ile Thr Asp Lys Arg Pro Trp Trp Ile Ser Lys His Lys Pro Leu
        195                 200                 205

Leu Lys Lys Leu Ser Asn Tyr Glu Thr Met Asp Ile Asp Gly Asp Asp
    210                 215                 220

Glu Val His Cys Phe Pro Arg Val Thr Val Gly Leu Lys Arg Tyr Gln
225                 230                 235                 240

Lys Glu Leu Ser Ile Glu Pro Gln Lys Tyr Ser Tyr Ser Met Lys Asp
                245                 250                 255

Phe Arg Asp Leu Leu Arg Ser Ser Tyr Ala Leu Lys Arg Val Glu Ala
            260                 265                 270

Ile Lys Thr Arg Asp Gly Leu Arg Gly Lys Pro Arg Leu Met Ile Leu
        275                 280                 285

Ser Arg Lys Arg Ser Arg Phe Phe Thr Asn Thr Asp Glu Ile Ala Lys
    290                 295                 300

Met Ala Glu Ser Leu Gly Phe Asp Val Ile Ile Lys Glu Ala Gly Trp
```

```
305                 310                 315                 320
Ser Met Trp Gly Phe Ala Asn Val Val Asn Ser Cys Asp Val Leu Leu
                325                 330                 335

Gly Val His Gly Ala Gly Leu Thr Asn Ile Leu Phe Leu Pro Glu Asn
                340                 345                 350

Ala Val Phe Val Gln Val Val Pro Tyr Gly Gly Val Thr Leu Asp Trp
                355                 360                 365

Leu Ala Thr Asn Asp Phe Gly Asn Pro Ser Lys Asp Met Asn Ile Lys
                370                 375                 380

Tyr Leu Glu Tyr Lys Ile Ser Leu Glu Glu Ser Thr Leu Ile Gln Gln
385                 390                 395                 400

Tyr Pro Leu Asp His Met Phe Ile Lys Asp Pro Leu Ile Glu Lys
                405                 410                 415

Ile Gly Trp Glu Glu Phe Lys Ser Val Tyr Leu Asp Lys Gln Asn Val
                420                 425                 430

Lys Leu Asp Val Asp Arg Phe Arg Pro Thr Leu Gln Lys Ala Leu Glu
                435                 440                 445

Leu Leu His Gln
                450

<210> SEQ ID NO 14
<211> LENGTH: 462
<212> TYPE: PRT
<213> ORGANISM: Glycine max

<400> SEQUENCE: 14

Met Ile Tyr Asp Thr Val Leu Ala Lys Ser Phe Ser Arg Tyr Asp Gln
1               5                   10                  15

Lys Arg Leu Gly Tyr Gly Ala Phe Val Ser Cys Leu Phe Ile Ile Leu
                20                  25                  30

Ser Leu Cys Thr Val Phe Lys Pro Tyr Leu Gly Pro Val His Val Leu
                35                  40                  45

Ser Leu Lys Leu Phe Ile Asp Val Asp Thr Lys Met Leu Ile Thr Ser
                50                  55                  60

Ser Ser Leu Gln Ile Ala Lys Val Lys Gly Lys Glu Thr Lys Lys Glu
65                  70                  75                  80

Glu Leu Leu Cys Thr Ser Glu Glu Arg Thr Glu Phe Cys Gln Ala Arg
                85                  90                  95

Gly Asp Ile Arg Val His Gly Lys Ser Ser Thr Val Ser Ile Val Ser
                100                 105                 110

Ser Lys Thr Thr Met Leu Glu Lys Thr Met Ser Arg Ser Leu Lys Pro
                115                 120                 125

Tyr Ala Arg Arg Gly Asp Ile Asp Ala Met Asn Arg Val Arg Glu Trp
                130                 135                 140

Ser Val Lys Ala Val Asn Ala Ser Gln Lys Ala Pro Gln Cys Thr Gln
145                 150                 155                 160

Ser His Asn Ile Thr Ala Val Leu Phe Ser Thr Gly Gly Tyr Ser Gly
                165                 170                 175

Asn His Phe His Glu Phe Thr Asp Ile Val Ile Pro Leu Phe Leu Thr
                180                 185                 190

Ala Arg Gln Phe Asn Gly Glu Val Gln Phe Ile Ile Thr Asp Lys Arg
                195                 200                 205

Pro Trp Trp Ile Ser Lys His Lys Pro Leu Leu Lys Lys Leu Ser Asn
                210                 215                 220
```

Tyr Glu Thr Met Asp Ile Asp Gly Asp Asp Gln Val His Cys Phe Pro
225                 230                 235                 240

Ser Val Thr Val Gly Leu Lys Arg Tyr Gln Lys Glu Leu Ser Ile Asp
            245                 250                 255

Pro Gln Lys Tyr Ser Tyr Ser Met Lys Asp Phe Arg Asp Leu Leu Arg
        260                 265                 270

Ser Ser Tyr Ala Leu Lys Arg Val Glu Ala Met Lys Ile Arg Asp Gly
    275                 280                 285

Leu Arg Gly Lys Pro Arg Leu Met Ile Leu Ser Arg Lys Arg Ser Arg
290                 295                 300

Ser Phe Thr Asn Thr Asp Glu Ile Ala Lys Met Ala Ala Ser Leu Gly
305                 310                 315                 320

Phe Asp Val Ile Val Lys Glu Ala Gly Trp Ser Met Trp Gly Phe Ala
            325                 330                 335

Asn Val Val Asn Ser Cys Asp Val Leu Leu Gly Val His Gly Ala Gly
            340                 345                 350

Leu Thr Asn Ile Leu Phe Leu Pro Glu Asn Ala Val Phe Ile Gln Val
        355                 360                 365

Val Pro Tyr Gly Gly Phe Thr Leu Asp Trp Leu Ala Thr Asn Asp Phe
370                 375                 380

Gly Lys Pro Ser Lys Asp Met Asn Leu Lys Tyr Leu Glu Tyr Lys Ile
385                 390                 395                 400

Gly Leu Lys Glu Ser Thr Leu Ile Gln Gln Tyr Pro Leu Asp His Ile
                405                 410                 415

Phe Ile Lys Asp Pro Pro Leu Val Glu Lys Ile Gly Trp Glu Glu Phe
            420                 425                 430

Lys Ser Val Tyr Leu Asp Lys Gln Asn Val Lys Leu Asp Val Asp Arg
            435                 440                 445

Phe Arg Pro Thr Leu Gln Lys Ala Phe Glu Leu Leu His Gln
        450                 455                 460

<210> SEQ ID NO 15
<211> LENGTH: 384
<212> TYPE: PRT
<213> ORGANISM: Arabidopsis thaliana

<400> SEQUENCE: 15

Met Lys Pro Ile Cys Thr Lys Leu Ala Arg Thr Glu Phe Cys Glu Leu
1               5                   10                  15

Asn Gly Asp Val Arg Val His Gly Lys Ser Ala Thr Val Ser Ala Ala
            20                  25                  30

Ile Thr Phe Ala Phe Ser Gly Asn Ser Thr Trp His Ile Arg Pro Tyr
        35                  40                  45

Ala Arg Lys Gly Asp Thr Val Ala Met Lys Arg Val Arg Glu Trp Thr
    50                  55                  60

Val Lys Leu Glu Gln Asn Ala Asp Gln Leu Glu Asn Ala Asn Phe Ser
65                  70                  75                  80

Arg Cys Val Arg Asn His Ser Val Pro Ala Met Ile Phe Ser Leu Gly
                85                  90                  95

Gly Tyr Ser Met Asn Asn Phe His Asp Phe Thr Asp Ile Val Ile Pro
            100                 105                 110

Leu Tyr Thr Thr Ala Arg Arg Phe Asn Gly Glu Val Gln Phe Leu Val
        115                 120                 125

Thr Asn Lys Ser Pro Ser Trp Ile Asn Lys Phe Lys Glu Leu Val Arg
130                 135                 140

Lys Leu Ser Asn Tyr Glu Val Ile Tyr Ile Asp Glu Glu Asp Glu Thr
145                 150                 155                 160

His Cys Phe Ser Ser Val Thr Val Gly Leu Thr Arg His Arg Glu Tyr
            165                 170                 175

Phe Lys Glu Leu Thr Ile Asp Pro Ser Asn Ser Glu Tyr Ser Met Ser
        180                 185                 190

Asp Phe Arg Ser Phe Leu Arg Asp Thr Tyr Ser Leu Arg Asn Asp Ala
    195                 200                 205

Val Ala Thr Arg Gln Ile Arg Arg Arg Pro Arg Ile Leu Ile Leu
210                 215                 220

Ala Arg Gly Arg Ser Arg Ala Phe Val Asn Thr Gly Glu Ile Ala Arg
225                 230                 235                 240

Ala Ala Arg Gln Ile Gly Phe Lys Val Val Ala Glu Ala Asn Ile
                245                 250                 255

Gly Ile Ala Lys Phe Ala Gln Thr Val Asn Ser Cys Asp Val Met Leu
            260                 265                 270

Gly Val His Gly Ala Gly Leu Thr Asn Met Val Phe Leu Pro Glu Asn
        275                 280                 285

Ala Val Val Ile Gln Val Leu Pro Ile Gly Gly Phe Glu Trp Leu Ala
290                 295                 300

Lys Thr Asp Phe Glu Lys Pro Ser Glu Gly Met Asn Leu Arg Tyr Leu
305                 310                 315                 320

Glu Tyr Lys Ile Ala Val Glu Glu Ser Thr Leu Val Lys Lys Tyr Gly
                325                 330                 335

Arg Asp His Glu Ile Val Arg Asp Pro Ser Ala Val Ala Lys His Gly
            340                 345                 350

Trp Glu Met Phe Lys Ser Val Tyr Leu Val Gln Gln Asn Val Ser Ile
        355                 360                 365

Asp Ile Asn Arg Phe Lys Pro Val Leu Val Lys Ala Leu Glu Leu Leu
    370                 375                 380

<210> SEQ ID NO 16
<211> LENGTH: 470
<212> TYPE: PRT
<213> ORGANISM: Arabidopsis thaliana

<400> SEQUENCE: 16

Met Thr Lys Lys Asp Ile Leu Tyr Asp Thr Val Leu Ala Arg Ser Phe
1               5                   10                  15

Ser Lys Thr Asp Gln Lys Arg Leu Cys Cys Gly Ala Phe Ile Ala Ser
            20                  25                  30

Leu Leu Leu Val Leu Thr Leu Cys Thr Val Val Lys Pro Tyr Leu Ser
        35                  40                  45

Pro Leu Pro Ile Val Glu Leu Gln Leu Ser Val Gly Thr Gly Leu Arg
    50                  55                  60

Met Leu Ser Ile Thr Glu Leu Thr Thr Asn Thr Thr Ile Ser Lys Glu
65                  70                  75                  80

Glu Val Ile Ser Glu Cys Asn Lys Met Glu Lys Pro Ile Cys His Cys
                85                  90                  95

Asn Thr Leu Gly Ser Lys Glu Phe Cys Asp Val Ser Gly Asp Val Arg
            100                 105                 110

Ile His Gly Lys Ser Ala Thr Val Leu Ala Ala Val Thr Phe Ala Phe
        115                 120                 125

Ser Gly Asn Ser Thr Trp Tyr Met Arg Pro Tyr Ala Arg Lys Asp Gln 130                 135                 140
Val Pro Ala Met Lys Arg Val Arg Glu Trp Thr Val Lys Leu Val Gln
145                 150                 155                 160

Asn Ala Ser Leu Ser Arg Cys Val Arg Asn His Ser Val Pro Ala Ile
                165                 170                 175

Leu Phe Ser Leu Gly Gly Phe Ser Leu Asn Asn Phe His Asp Phe Thr
            180                 185                 190

Asp Ile Val Ile Pro Leu Tyr Thr Thr Ala Arg Arg Phe Ser Gly Glu
        195                 200                 205

Val Gln Phe Leu Val Thr Asn Lys Asn Leu Leu Trp Ile Asn Lys Phe
    210                 215                 220

Lys Glu Leu Val Arg Lys Leu Ser Asn Tyr Glu Val Ile Tyr Ile Asp
225                 230                 235                 240

Glu Glu Asp Glu Thr His Cys Phe Ser Ser Val Ile Val Gly Leu Asn
                245                 250                 255

Arg His Arg Asp Tyr Asp Lys Glu Leu Thr Thr Asp Pro Ser Asn Ser
            260                 265                 270

Glu Tyr Ser Met Ser Asp Phe Arg Lys Phe Leu Arg Asp Thr Tyr Ser
        275                 280                 285

Leu Arg Asn Ser Ala Val Thr Thr Arg Arg Lys Pro Arg Ile Leu Ile
    290                 295                 300

Leu Ser Arg Ser Arg Ser Arg Ala Phe Val Asn Ala Gly Glu Ile Ala
305                 310                 315                 320

Arg Ala Ala Arg Gln Ile Gly Phe Lys Val Val Ala Glu Ala Asn
                325                 330                 335

Thr Glu Ile Ala Ser Phe Ala Ile Thr Val Asn Ser Cys Asp Val Met
            340                 345                 350

Leu Gly Val His Gly Ala Gly Met Thr Asn Met Val Phe Leu Pro Asp
        355                 360                 365

Asn Ala Ile Val Ile Gln Ile Leu Pro Ile Gly Gly Phe Glu Trp Leu
    370                 375                 380

Ala Lys Met Asp Phe Glu Tyr Pro Ser Lys Gly Met Asn Leu Arg Tyr
385                 390                 395                 400

Leu Glu Tyr Lys Ile Thr Ala Glu Glu Ser Thr Leu Val Lys Gln Tyr
                405                 410                 415

Gly Arg Asp His Glu Phe Val Arg Asp Pro Leu Ala Val Ala Lys Arg
            420                 425                 430

Gly Trp Gly Thr Phe Lys Ser Val Tyr Leu Val Gln Gln Asn Val Ser
        435                 440                 445

Val Asp Ile Asn Arg Phe Lys Leu Val Leu Val Lys Ala Leu Glu Leu
    450                 455                 460

Leu His Asn Gln Ser Val
465                 470

<210> SEQ ID NO 17
<211> LENGTH: 462
<212> TYPE: PRT
<213> ORGANISM: Hordeum vulgare

<400> SEQUENCE: 17

Met Lys Gln Pro Arg Ser Arg Gln Glu Pro Arg Arg Met Gly Asn Ser
1               5                   10                  15

Ala Met Val Val Thr Met Leu Leu Ser Leu Cys Val Leu Thr Phe Ile
            20                  25                  30

```
Lys Ala Arg Tyr Cys Ser Thr Pro Tyr Pro Asn Lys Pro Ala Pro Leu
             35                  40                  45

Leu Asp Leu Glu Ala Gly Ile Asp Glu Asp Tyr Asp Ser Ser Arg Tyr
 50                  55                  60

Lys Ile Ser Gly Pro Ile Gly Glu Glu Phe Asp Pro Ser Arg Pro
 65                  70                  75                  80

Thr Cys Tyr Asn Thr Ser Lys Arg Ser Glu Arg Cys Ala Ala Val Gly
                 85                  90                  95

Asp Ile Arg Val Asp Gly Asn His Ser Lys Ile Tyr Ile Ser Pro Leu
                100                 105                 110

Asp Arg Val Trp Arg Thr Lys Pro Tyr Ala Arg Arg His Asp Ala Val
            115                 120                 125

Ala Met Asp Asp Val Arg Glu Phe Ala Leu Leu Pro Phe Gly Gly Gly
    130                 135                 140

Asn Asp Ser Ala Val Pro Pro Leu Cys Thr Arg Asn His Ser Val Pro
145                 150                 155                 160

Ala Phe Leu Phe Ser Ser Gly Gly Phe Ala Gly Asn Leu Tyr His Asp
                165                 170                 175

Tyr Thr Asp Val Leu Val Pro Leu Phe Thr Ser Thr His His Phe Gly
            180                 185                 190

Gly Glu Val Gln Phe Leu Leu Thr Asp Ile Lys Asp Trp Trp Leu Asp
            195                 200                 205

Lys Phe Thr Pro Leu Phe Arg Gln Leu Ser Asn Tyr Asp Val Ile Asp
    210                 215                 220

Val Asp Asn Asp Gln Glu Val His Cys Phe Pro Arg Ile Val Ile Gly
225                 230                 235                 240

Ser Thr Phe His Arg Pro Met Gly Ile Asp Gly Thr Arg Ser Pro Gly
                245                 250                 255

Gly Glu Thr Val Ala Asp Phe Lys Arg Leu Leu Arg Arg Ala Phe Arg
            260                 265                 270

Leu Asp Arg Val Val Ala Ser His Asp Gly Ser Ala Ser Leu Gly Lys
            275                 280                 285

Pro Arg Leu Leu Ile Ile Ser Arg Lys Ser Ser Arg Arg Phe Leu Asn
    290                 295                 300

Glu Arg Ala Met Ala His Ala Ala Ala Leu Ala Gln Phe Asp Val Arg
305                 310                 315                 320

Ile Ala Glu Pro Asp Asn His Thr Asp Met Pro Asn Phe Ala Arg Leu
                325                 330                 335

Val Asn Ser Ala Asp Val Met Met Gly Val His Gly Ala Gly Leu Thr
            340                 345                 350

Asn Met Val Phe Leu Pro Ser Arg Ala Val Leu Gln Val Val Pro
            355                 360                 365

Phe Gly Gly Leu Glu Trp Leu Ser Arg Val Thr Phe Lys Asp Pro Ala
    370                 375                 380

Lys Asp Phe Asp Val Thr Tyr Met Glu Tyr Asn Val Ser Leu Glu Glu
385                 390                 395                 400

Ser Ser Leu Lys Asn Leu Tyr Pro Lys Asp His Phe Tyr Leu Gln His
                405                 410                 415

Pro Tyr Asp Val His Lys Lys Gly Trp Asn Ala Ile Lys Thr Val Tyr
            420                 425                 430

Leu Asp Lys Gln Ser Val Arg Leu Asp Leu Ala Lys Leu Thr Arg Thr
            435                 440                 445

Leu Glu His Ala Arg Ser Leu Leu Pro Ser Ser Ser Ser His
```

<210> SEQ ID NO 18
<211> LENGTH: 455
<212> TYPE: PRT
<213> ORGANISM: Brachypodium distachyon

<400> SEQUENCE: 18

```
Met Met Lys Ala Gln Gln Gly Arg Ser Arg Gln Glu Pro Arg Arg
1               5                   10                  15

Met Gly Asn Ser Ala Met Val Ile Thr Met Leu Leu Ser Leu Cys Val
            20                  25                  30

Leu Thr Phe Ile Lys Ala Arg Tyr Cys Ser Thr Pro Phe Pro Lys Ala
        35                  40                  45

Ala Pro Val Leu Glu Val Glu Val Asp Glu Asp Tyr Asp Gly Ser Arg
    50                  55                  60

Tyr Arg Ile Asp Gly Pro Ile Gly Glu Glu Asp Phe Asp Pro His Arg
65                  70                  75                  80

Pro Thr Cys Tyr Asn Thr Ser Lys Arg Ser Glu Arg Cys Ala Ala Val
                85                  90                  95

Gly Asp Ile Arg Phe Asp Gly Asn His Ser Lys Ile Tyr Ile Asn Pro
            100                 105                 110

Leu Asp Lys Glu Trp Arg Thr Lys Pro Tyr Ala Arg Arg His Asp Ala
        115                 120                 125

Val Ala Met Asp Asp Val Arg Glu Phe Thr Leu Leu Pro Phe Asp Thr
    130                 135                 140

Glu Ser Ser Asn Thr Thr Val Val Pro Pro Leu Cys Thr Arg Asn His
145                 150                 155                 160

Ser Val Pro Ala Phe Leu Phe Ser Ser Gly Gly Phe Ala Gly Asn Leu
                165                 170                 175

Tyr His Asp Tyr Thr Asp Val Leu Val Pro Leu Phe Thr Ser Thr His
            180                 185                 190

His Phe Arg Gly Glu Val Gln Phe Leu Leu Thr Asp Ile Lys Asp Trp
        195                 200                 205

Trp Leu Asp Lys Phe Thr Pro Leu Phe Arg Gln Leu Ser Asn Tyr Asp
    210                 215                 220

Val Ile Asp Ala Asp Asn Asp Gln Gln Val His Cys Phe Arg Arg Ile
225                 230                 235                 240

Ile Ile Gly Ala Thr Phe His Arg Ala Met Gly Ile Asp Pro Lys Arg
                245                 250                 255

Ser Pro Gly Gly Glu Thr Val Ala Asp Phe Lys Arg Leu Leu Arg His
            260                 265                 270

Ala Phe His Leu Thr Arg Pro Val Ala Ser Arg Asp Asn Pro Arg Leu
        275                 280                 285

Leu Ile Ile Ser Arg Lys Ser Ser Arg Arg Phe Leu Asn Glu Arg Ala
    290                 295                 300

Met Ala His Ala Ala Ala Leu Ala Lys Phe Asp Val Arg Ile Ala Glu
305                 310                 315                 320

Pro Asp Asn His Thr Asp Met Pro Asn Phe Ala Arg Leu Val Asn Ser
                325                 330                 335

Ala Asp Ile Met Met Gly Val His Gly Ala Gly Leu Thr Asn Met Val
            340                 345                 350

Phe Leu Pro Ser Arg Ala Val Leu Leu Gln Val Val Pro Phe Gly Gly
        355                 360                 365
```

Leu Glu Trp Leu Ser Arg Val Thr Phe Lys Asp Pro Ala Lys Asp Met
    370                 375                 380

Asp Val Asn Tyr Met Glu Tyr Asn Val Ser Leu Glu Glu Ser Ser Leu
385                 390                 395                 400

Arg Asn Leu Tyr Pro Glu Gly His Phe Tyr Leu Lys His Pro Tyr Asp
                405                 410                 415

Val His Lys Lys Gly Trp Asp Ala Ile Lys Thr Val Tyr Leu Asp Lys
                420                 425                 430

Gln Ser Val Arg Leu Asn Leu Thr Lys Phe Val Gln Thr Leu Glu Leu
            435                 440                 445

Ala Arg Ser Arg Leu Pro Ala
    450                 455

<210> SEQ ID NO 19
<211> LENGTH: 1536
<212> TYPE: DNA
<213> ORGANISM: Paspalum notatum

<400> SEQUENCE: 19
gccatccagc gctccaacca gctccagcaa gctccagatc cagcggaaac cgaccggcga      60
tgaagcagcc taggggggcgg caggagccgc ggcgggtggg caacgccgcc atggtcgtca     120
ccatgctcat ctccctctgc gtcctcacct acatcaaggc gcgatactgc tccaaccect     180
tccccaagkc gccggagccg ctggagccag cggcggtgga tgtggacgag gactacgaca     240
gcacgcggta caagctctcg ggccccatcg gcgaggaaga cttcgacccg acgcgcccca     300
cgtgctacaa cacgagcaag cgctccgagc ggtgcgcggc ggtgggcgac atccgcgtcg     360
acggcaacca ctccaagatc tacatcagcc cactctcccg cgagtggcgc accaaaccct     420
acgcgcgcct gcacgacgcc gtggccatgg acgacgtgcg cgagtacacg ctcgtcccct     480
tcggcggcgc caacgacacc gccgtgccgc cgctctgcac gcgcaaccac tccgccccgg     540
ccttcctctt ctccaacggc ggcttcgcgg caacctcta ccacgactac gccgacgtcc     600
tcgtgccgct cttcaccagc acgcaccatt tcggtgggga ggtggtgttc ctgctcagcg     660
ggatgaagga ctggtggaac gagaagttca cgccgctgtt ccgccagctc tcgcgctacg     720
acgtcgtcga cgtcgacaac gacctcgagg tgcactgctt ccatcggatc gtcatcgggg     780
ccaccttcca ccgcgccatg ggcatcgacc cacgcggtc gccgggcggg atcacggtgg     840
ccgacttcaa gcggacgctg cgscgcgcgt tcaggctgga gcgcgccgtc gcgtcgcgga     900
cgggggcgcc gaggagggac cgcccgcggc tactcatcat ctcgcgcagg agctcgcgcc     960
ggttcctcaa cgagcgcgcc atggcgcacg ccgccgcggc ggccaggttc gacgtgcgca    1020
tcgccgagcc cgacaaccac acggacatgc ccaacttcgc gcggctcgtc aactcggcgg    1080
acgtgatgat gggcgtgcac ggcgccgggc tcaccaacat ggtgttcctg cccagccgcg    1140
ccgtgctcat ccaggtggtg cccttcgggg gkctcgagtg gctctcgcgc gtcaccttca    1200
aggaccccgc cagggacatg gacgtcaact acatggagta caacgtgtcg ctggaggaga    1260
gctcgctcag ggacctctac ccggaggggc atttctacct caagcaccca tacgacgtgc    1320
acaagaaggg atgggacgcc atcaagaccg tctacctcga caagcagaac gtcaggctca    1380
acctcaccag gttcactgag acgctggagc aggcaaggga cctcttgcca ctgccctgac    1440
gtccattgca tgctctcagg atggatttgc gcgccttaat tggtagctag gcaggcagtg    1500
aagcagatgc aggcaggctc atcaccatga ccatgc                              1536

```
<210> SEQ ID NO 20
<211> LENGTH: 459
<212> TYPE: PRT
<213> ORGANISM: Paspalum notatum
<220> FEATURE:
<221> NAME/KEY: misc_feature
<222> LOCATION: (44)..(44)
<223> OTHER INFORMATION: Xaa can be any naturally occurring amino acid

<400> SEQUENCE: 20

Met Lys Gln Pro Arg Gly Arg Gln Glu Pro Arg Arg Val Gly Asn Ala
1               5                   10                  15

Ala Met Val Val Thr Met Leu Ile Ser Leu Cys Val Leu Thr Tyr Ile
            20                  25                  30

Lys Ala Arg Tyr Cys Ser Asn Pro Phe Pro Lys Xaa Pro Glu Pro Leu
        35                  40                  45

Glu Pro Ala Ala Val Asp Val Asp Glu Asp Tyr Asp Ser Thr Arg Tyr
    50                  55                  60

Lys Leu Ser Gly Pro Ile Gly Glu Glu Asp Phe Asp Pro Thr Arg Pro
65                  70                  75                  80

Thr Cys Tyr Asn Thr Ser Lys Arg Ser Glu Arg Cys Ala Ala Val Gly
                85                  90                  95

Asp Ile Arg Val Asp Gly Asn His Ser Lys Ile Tyr Ile Ser Pro Leu
            100                 105                 110

Ser Arg Glu Trp Arg Thr Lys Pro Tyr Ala Arg Leu His Asp Ala Val
        115                 120                 125

Ala Met Asp Asp Val Arg Glu Tyr Thr Leu Val Pro Phe Gly Gly Ala
    130                 135                 140

Asn Asp Thr Ala Val Pro Pro Leu Cys Thr Arg Asn His Ser Ala Pro
145                 150                 155                 160

Ala Phe Leu Phe Ser Asn Gly Gly Phe Ala Gly Asn Leu Tyr His Asp
                165                 170                 175

Tyr Ala Asp Val Leu Val Pro Leu Phe Thr Ser Thr His His Phe Gly
            180                 185                 190

Gly Glu Val Val Phe Leu Leu Ser Gly Met Lys Asp Trp Trp Asn Glu
        195                 200                 205

Lys Phe Thr Pro Leu Phe Arg Gln Leu Ser Arg Tyr Asp Val Val Asp
    210                 215                 220

Val Asp Asn Asp Leu Glu Val His Cys Phe His Arg Ile Val Ile Gly
225                 230                 235                 240

Ala Thr Phe His Arg Ala Met Gly Ile Asp Pro Thr Arg Ser Pro Gly
                245                 250                 255

Gly Ile Thr Val Ala Asp Phe Lys Arg Thr Leu Arg Arg Ala Phe Arg
            260                 265                 270

Leu Glu Arg Ala Val Ala Ser Arg Thr Gly Ala Pro Arg Arg Asp Arg
        275                 280                 285

Pro Arg Leu Leu Ile Ile Ser Arg Arg Ser Ser Arg Phe Leu Asn
    290                 295                 300

Glu Arg Ala Met Ala His Ala Ala Ala Ala Arg Phe Asp Val Arg
305                 310                 315                 320

Ile Ala Glu Pro Asp Asn His Thr Asp Met Pro Asn Phe Ala Arg Leu
                325                 330                 335

Val Asn Ser Ala Asp Val Met Met Gly Val His Gly Ala Gly Leu Thr
            340                 345                 350

Asn Met Val Phe Leu Pro Ser Arg Ala Val Leu Ile Gln Val Val Pro
        355                 360                 365
```

```
Phe Gly Gly Leu Glu Trp Leu Ser Arg Val Thr Phe Lys Asp Pro Ala
    370                 375                 380
Arg Asp Met Asp Val Asn Tyr Met Glu Tyr Asn Val Ser Leu Glu Glu
385                 390                 395                 400
Ser Ser Leu Arg Asp Leu Tyr Pro Glu Gly His Phe Tyr Leu Lys His
            405                 410                 415
Pro Tyr Asp Val His Lys Lys Gly Trp Asp Ala Ile Lys Thr Val Tyr
            420                 425                 430
Leu Asp Lys Gln Asn Val Arg Leu Asn Leu Thr Arg Phe Thr Glu Thr
            435                 440                 445
Leu Glu Gln Ala Arg Asp Leu Leu Pro Leu Pro
    450                 455

<210> SEQ ID NO 21
<211> LENGTH: 1498
<212> TYPE: DNA
<213> ORGANISM: Eragrostis nindensis

<400> SEQUENCE: 21
gcttgctctg cagtctcggg cggtggggga tccagccaga cccggagcga tgaagcatcc      60
gaggagccgg caggagccgc ggcggatggg caacggcgcc atggtcgtca ccatgctgct     120
ctcgctctgc gtcctcacct acatcaaggc gcgatactgc tccaacccat tcccaaggc     180
ggcggatgag atggaggtgg tggagatcga cgaggactac gacagcacgc ggtacaagat     240
ggacggcccg atcggggagg aggacttcga cccttcccgg ccgacttgct acaacaccag     300
caagcgctcg gagcggtgcg cggccgtggg cgacatccgc gtcgacggca accactccaa     360
aatctacatc agcccgctga gcaaggagtg gaagacgaag ccgtacgcgc ggcggcacga     420
cgccgtggcc atggacgacg tgcgggagtt cacgctcctc cccttcggcg ggccaacga     480
cacggccgtg ccgccgctct gcacccggaa ccactccgtc ccgggcttcc tcttctccat     540
cggcgggttc gccggcaacc tgtaccacga ctacaccgac gtgctggtgc cgctcttcac     600
cagcacccac cacttcggcg gggaggtgca gttgatgatc agcgacatat ggggcaagga     660
ggacaaggac tggtgggtcg acaagttcac gccgctgttc cgccagctct ccaagtacga     720
cgtcatcgac gccgacaacg accaggaggt gcactgcttc ccgcgcatcg tcatcggccc     780
caccttccac cgcgccatgg catcgaccc acgcgctcg ccgggggca tcaacatcgc     840
cgacttcaag cgcctcctcc gccgcacctt ccgcctcgag gcgccgtcg cgtcgcgcac     900
gggggcgccg cgacgcgaca agccgcgcct gctcatcatc tcccgcaaga gctcccggcg    960
attcctcaac gagcgcgccg tggcgcacgc cgccgcgctg ccaagttcg acgtgcgcat    1020
cgccgagccg gacaaccaca cggacatgcc caacttcgcg cggctcgtca actcagcgga    1080
cgtgatgatg ggcgtgcacg gcgccgggct caccaacatg gtgttcctcc cgagccgcgc    1140
cgtgctcatc caggtggtgc ccttcggcg actcgagtgg ctcagccgcg tcaccttcaa    1200
ggacccggcc aaggactacg acgtcaacta catggagtac aacgtgtcgc tggaggagag    1260
ctcgctcagg gacctctacc cggaggacca tttctacctc aagcatccct acgacgtgca    1320
caagaaggga tgggacgcca tcaagaccac ctatctcgac aagcagaacg tcaggctcaa    1380
cctcaccagg ttcaccaaaa cgctgcaaca ggcgcgggac ctgttgcctt caccctgaca    1440
tcatcactgg gaggagctgc gacggtcaag ggatagatag gttcatcatg tgaagctt     1498

<210> SEQ ID NO 22
```

<211> LENGTH: 462
<212> TYPE: PRT
<213> ORGANISM: Eragrostis nindensis

<400> SEQUENCE: 22

```
Met Lys His Pro Arg Ser Arg Gln Glu Pro Arg Arg Met Gly Asn Gly
1               5                   10                  15

Ala Met Val Val Thr Met Leu Leu Ser Leu Cys Val Leu Thr Tyr Ile
            20                  25                  30

Lys Ala Arg Tyr Cys Ser Asn Pro Phe Pro Lys Ala Ala Asp Glu Met
        35                  40                  45

Glu Val Val Glu Ile Asp Glu Asp Tyr Asp Ser Thr Arg Tyr Lys Met
    50                  55                  60

Asp Gly Pro Ile Gly Glu Glu Asp Phe Asp Pro Ser Arg Pro Thr Cys
65                  70                  75                  80

Tyr Asn Thr Ser Lys Arg Ser Glu Arg Cys Ala Ala Val Gly Asp Ile
                85                  90                  95

Arg Val Asp Gly Asn His Ser Lys Ile Tyr Ile Ser Pro Leu Ser Lys
            100                 105                 110

Glu Trp Lys Thr Lys Pro Tyr Ala Arg Arg His Asp Ala Val Ala Met
        115                 120                 125

Asp Asp Val Arg Glu Phe Thr Leu Leu Pro Phe Gly Ala Asn Asp
    130                 135                 140

Thr Ala Val Pro Pro Leu Cys Thr Arg Asn His Ser Val Pro Gly Phe
145                 150                 155                 160

Leu Phe Ser Ile Gly Gly Phe Ala Gly Asn Leu Tyr His Asp Tyr Thr
                165                 170                 175

Asp Val Leu Val Pro Leu Phe Thr Ser Thr His His Phe Gly Gly Glu
            180                 185                 190

Val Gln Leu Met Ile Ser Asp Ile Trp Gly Lys Glu Asp Lys Asp Trp
        195                 200                 205

Trp Val Asp Lys Phe Thr Pro Leu Phe Arg Gln Leu Ser Lys Tyr Asp
    210                 215                 220

Val Ile Asp Ala Asp Asn Asp Gln Glu Val His Cys Phe Pro Arg Ile
225                 230                 235                 240

Val Ile Gly Pro Thr Phe His Arg Ala Met Gly Ile Asp Pro Thr Arg
                245                 250                 255

Ser Pro Gly Gly Ile Asn Ile Ala Asp Phe Lys Arg Leu Leu Arg Arg
            260                 265                 270

Thr Phe Arg Leu Glu Arg Ala Val Ala Ser Arg Thr Gly Ala Pro Arg
        275                 280                 285

Arg Asp Lys Pro Arg Leu Leu Ile Ile Ser Arg Lys Ser Ser Arg Arg
    290                 295                 300

Phe Leu Asn Glu Arg Ala Val Ala His Ala Ala Leu Ala Lys Phe
305                 310                 315                 320

Asp Val Arg Ile Ala Glu Pro Asp Asn His Thr Asp Met Pro Asn Phe
                325                 330                 335

Ala Arg Leu Val Asn Ser Ala Asp Val Met Met Gly Val His Gly Ala
            340                 345                 350

Gly Leu Thr Asn Met Val Phe Leu Pro Ser Arg Ala Val Leu Ile Gln
        355                 360                 365

Val Val Pro Phe Gly Gly Leu Glu Trp Leu Ser Arg Val Thr Phe Lys
    370                 375                 380

Asp Pro Ala Lys Asp Tyr Asp Val Asn Tyr Met Glu Tyr Asn Val Ser
```

```
                385                 390                 395                 400
Leu Glu Glu Ser Ser Leu Arg Asp Leu Tyr Pro Glu Asp His Phe Tyr
                    405                 410                 415

Leu Lys His Pro Tyr Asp Val His Lys Lys Gly Trp Asp Ala Ile Lys
                420                 425                 430

Thr Thr Tyr Leu Asp Lys Gln Asn Val Arg Leu Asn Leu Thr Arg Phe
            435                 440                 445

Thr Lys Thr Leu Gln Gln Ala Arg Asp Leu Leu Pro Ser Pro
        450                 455                 460

<210> SEQ ID NO 23
<211> LENGTH: 462
<212> TYPE: PRT
<213> ORGANISM: Glycine max

<400> SEQUENCE: 23

Met Ile Tyr Asp Thr Val Leu Ala Lys Ser Phe Ser Arg Tyr Asp Gln
1               5                   10                  15

Lys Arg Leu Gly Tyr Gly Ala Phe Val Ser Cys Leu Leu Ile Val Leu
                20                  25                  30

Ser Leu Cys Thr Val Phe Lys Pro Tyr Leu Gly Pro Val His Val Leu
            35                  40                  45

Asn Leu Lys Leu Phe Ile Asp Val Asp Thr Lys Met Leu Ile Thr Arg
        50                  55                  60

Ser Ser Ser Gln Ile Ala Lys Val Glu Gly Lys Glu Thr Lys Lys Glu
65                  70                  75                  80

Glu Leu Leu Cys Thr Ser Glu Glu Arg Thr Lys Phe Cys Gln Ala Arg
                85                  90                  95

Gly Asp Ile Arg Val His Gly Lys Ser Ser Thr Val Tyr Ile Val Ser
                100                 105                 110

Ser Lys Thr Thr Met Ser Glu Lys Asn Met Ser Trp Asn Leu Lys Pro
            115                 120                 125

Tyr Ala Arg Arg Asp Asp Val Asp Ala Met Ile Arg Val Arg Glu Trp
        130                 135                 140

Ser Val Lys Ala Val Asn Val Ser Gln Lys Ala Pro Gln Cys Thr Gln
145                 150                 155                 160

Tyr His Asn Ile Pro Ala Val Leu Phe Ser Thr Gly Gly Tyr Ala Gly
                165                 170                 175

Asn His Phe His Glu Phe Thr Asp Ile Val Ile Pro Leu Phe Leu Thr
                180                 185                 190

Ala Arg Gln Phe Asn Gly Glu Val Gln Phe Ile Ile Thr Asp Lys Arg
            195                 200                 205

Pro Trp Trp Ile Ser Lys His Lys Pro Leu Leu Lys Lys Leu Ser Asn
        210                 215                 220

Tyr Glu Thr Met Asp Ile Asp Gly Asp Asp Glu Val His Cys Phe Pro
225                 230                 235                 240

Arg Val Thr Val Gly Leu Lys Arg Tyr Gln Lys Glu Leu Ser Ile Glu
                245                 250                 255

Pro Gln Lys Tyr Ser Tyr Ser Met Lys Asp Phe Arg Asp Leu Leu Arg
                260                 265                 270

Ser Ser Tyr Ala Leu Lys Arg Val Glu Ala Ile Lys Thr Arg Asp Gly
            275                 280                 285

Leu Arg Gly Lys Pro Arg Leu Met Ile Leu Ser Arg Lys Arg Ser Arg
        290                 295                 300
```

```
Phe Phe Thr Asn Thr Asp Glu Ile Ala Lys Met Ala Glu Ser Leu Gly
305                 310                 315                 320

Phe Asp Val Ile Ile Lys Glu Ala Gly Trp Ser Met Trp Gly Phe Ala
                325                 330                 335

Asn Val Val Asn Ser Cys Asp Val Leu Leu Gly Val His Gly Ala Gly
            340                 345                 350

Leu Thr Asn Ile Leu Phe Leu Pro Glu Asn Ala Val Phe Val Gln Val
        355                 360                 365

Val Pro Tyr Gly Gly Val Thr Leu Asp Trp Leu Ala Thr Asn Asp Phe
370                 375                 380

Gly Asn Pro Ser Lys Asp Met Asn Ile Lys Tyr Leu Glu Tyr Lys Ile
385                 390                 395                 400

Ser Leu Glu Glu Ser Thr Leu Ile Gln Gln Tyr Pro Leu Asp His Met
                405                 410                 415

Phe Ile Lys Asp Pro Pro Leu Ile Glu Lys Ile Gly Trp Glu Glu Phe
            420                 425                 430

Lys Ser Val Tyr Leu Asp Lys Gln Asn Val Lys Leu Asp Val Asp Arg
        435                 440                 445

Phe Arg Pro Thr Leu Gln Lys Ala Leu Glu Leu Leu His Gln
450                 455                 460

<210> SEQ ID NO 24
<211> LENGTH: 22
<212> TYPE: DNA
<213> ORGANISM: Artificial
<220> FEATURE:
<223> OTHER INFORMATION: PHN151293 forward GSP

<400> SEQUENCE: 24
cgtcacggtg gccgacttca ag                                           22

<210> SEQ ID NO 25
<211> LENGTH: 27
<212> TYPE: DNA
<213> ORGANISM: Artificial
<220> FEATURE:
<223> OTHER INFORMATION: PHN151298 Reverse GSP

<400> SEQUENCE: 25
gttctgcttg tccaggtaca ccgtctt                                      27

<210> SEQ ID NO 26
<211> LENGTH: 418
<212> TYPE: PRT
<213> ORGANISM: Zea mays

<400> SEQUENCE: 26

Met Ser Ile Ser Val Asn Gly Gln Ser Cys Val Pro Pro Gly Phe Arg
1               5                   10                  15

Phe His Pro Thr Glu Glu Glu Leu Leu Asn Tyr Tyr Leu Arg Lys Lys
            20                  25                  30

Val Ala Ser Gln Glu Ile Asp Leu Asp Val Ile Arg Asp Val Asp Leu
        35                  40                  45

Asn Lys Leu Glu Pro Trp Asp Ile Gln Glu Lys Cys Lys Ile Gly Ser
    50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95
```

Ala Thr Gly Arg Asp Lys Ala Ile Tyr Asn Ala Val Lys Arg Ile Gly
            100                 105                 110

Met Arg Lys Thr Leu Val Phe Tyr Lys Gly Arg Ala Pro His Gly Gln
        115                 120                 125

Lys Ser Asp Trp Ile Met His Glu Tyr Arg Leu Asp Pro Ala Ala
    130                 135                 140

Ala Ala Ala Ala Gly Ser Gly Asp Ala Val Ala Asn Asp Ala Ala
145                 150                 155                 160

Ala Thr Ala Ala Ala Ala Ala Ala Ser Ser Asp Gly Gly Gln Glu
                165                 170                 175

Asp Gly Trp Val Val Cys Arg Val Phe Lys Lys His His Lys
        180                 185                 190

Glu Ser Gly Gly Gly Gly Asn Lys His Gly Ser Ser Asn Ser Glu
        195                 200                 205

His Gly His Gly Gly Ala Gly Lys Ala Ser Ala Ala Ala Ala Ala
        210                 215                 220

Ala His Gln His Gln His His Gly Gly Leu Gln Tyr Ser Ser Ser Asp
225                 230                 235                 240

Glu Ala Leu Asp Gln Ile Leu Gln Tyr Met Gly Arg Ser Cys Lys Gln
                245                 250                 255

Glu His Glu Leu Val Ser Pro Ala Pro Ala Pro Pro Gly Arg Ala Ala
        260                 265                 270

Ala Ser Arg Tyr Leu Arg Pro Ile Glu Thr Val Leu Gly Gly His Ala
        275                 280                 285

Phe Met Lys Leu Pro Ala Leu Glu Ser Pro Ser Ala Ala Ser Ala
        290                 295                 300

Ser Leu Thr Gln Pro Ala Gln His Asp Glu Leu Tyr Arg Ala Ala Gly
305                 310                 315                 320

Asn Gly Ile Thr Asp Trp Ala Met Met Asp Arg Leu Val Ala Ser His
                325                 330                 335

Leu Asn Gly Gln Gln Ala Pro Ala Ala Ala Asp Gln Leu Gly Gly Gly
        340                 345                 350

Cys Gly Phe Asp Ala Asp Ala Gly Ala Glu Asp Ala Asp Ala Gly Leu
        355                 360                 365

Ala Phe Tyr Ser Ala Ala Ala Ser Arg Leu Leu Gly Ser Gly Gly Gly
        370                 375                 380

Ala Gly Ser Asp Asp Asp Leu Trp Ser Phe Thr Arg Ser Ser Val Ser
385                 390                 395                 400

Ser Thr Ala Ala Ala Ala Thr Ser Thr Glu Arg Leu Ser His Val
                405                 410                 415

Ser Leu

<210> SEQ ID NO 27
<211> LENGTH: 400
<212> TYPE: PRT
<213> ORGANISM: Oryza sativa

<400> SEQUENCE: 27

Met Ser Ile Ser Val Asn Gly Gln Ser Cys Val Pro Pro Gly Phe Arg
1               5                   10                  15

Phe His Pro Thr Glu Glu Glu Leu Leu Asn Tyr Tyr Leu Arg Lys Lys
            20                  25                  30

Val Ala Ser Glu Gln Ile Asp Leu Asp Val Ile Arg Asp Val Asp Leu
        35                  40                  45

```
Asn Lys Leu Glu Pro Trp Asp Ile Gln Glu Arg Cys Lys Ile Gly Ser
 50                  55                  60

Gly Pro Gln Asn Asp Trp Tyr Phe Phe Ser His Lys Asp Lys Lys Tyr
 65                  70                  75                  80

Pro Thr Gly Thr Arg Thr Asn Arg Ala Thr Ala Ala Gly Phe Trp Lys
                 85                  90                  95

Ala Thr Gly Arg Asp Lys Ala Ile Tyr Asn Ala Val His Arg Ile Gly
                100                 105                 110

Met Arg Lys Thr Leu Val Phe Tyr Lys Gly Arg Ala Pro His Gly Gln
            115                 120                 125

Lys Ser Asp Trp Ile Met His Glu Tyr Arg Leu Asp Asp Pro Ala Thr
130                 135                 140

Asp Thr Ala Ala Thr Pro Thr Val Thr Ser Ala Ala Ala Ala Ala Ala
145                 150                 155                 160

Ala Ala Met Ala Ala Ala Asp Gly Gly Gln Glu Asp Gly Trp Val
                165                 170                 175

Val Cys Arg Val Phe Lys Lys Lys His His Lys Glu Ala Gly Gly
                180                 185                 190

Gly Gly Gly Lys His Gly Gly Asp Gly Ser Ala Gly Ala Lys Ala Ala
                195                 200                 205

His Ala Tyr Ser Ser Ser Asp Asp Ala Leu Asp Gln Ile Leu Gln Tyr
            210                 215                 220

Met Gly Arg Ser Cys Lys Gln Glu His Glu Leu Pro Ser Pro Gln Ala
225                 230                 235                 240

Ser Gly Gly Gly Gly Ala Gly Ala Gly Ser Arg Pro Ala Ser Arg Tyr
                245                 250                 255

Leu Arg Pro Ile Asp Thr Val Leu Gly Gly His Gly Phe Met Lys Leu
                260                 265                 270

Pro Pro Leu Glu Ser Pro Ser Ala Ala Thr Ala Leu Ser Ser Thr Pro
            275                 280                 285

Ser Thr Gly Gly Asp Ala Ala Ser Ser Ala Ala Ala Ala Ala Ala Asp
            290                 295                 300

His Leu Leu Leu His His His His Arg Thr Asp Trp Ala Met Met Asp
305                 310                 315                 320

Arg Leu Val Ala Ser His Leu Asn Gly Ala Asn Ser Asp Ala Pro Asp
                325                 330                 335

Asp Gln Leu Cys Phe Asp Ala Ala Asp Asp Asp Gly Leu Ala Tyr Tyr
            340                 345                 350

Ser Ala Ala Ala Thr Arg Leu Leu Gly Gly Ala Asn Ala Gly Thr Asp
            355                 360                 365

Asp Asp Leu Trp Ser Phe Ala Arg Ser Ala Ala Pro Pro Pro Pro Pro
370                 375                 380

Pro Pro Pro Ser Ser Ala Thr Pro Glu Arg Leu Ser His Val Ala Leu
385                 390                 395                 400

<210> SEQ ID NO 28
<211> LENGTH: 395
<212> TYPE: PRT
<213> ORGANISM: Oryza sativa

<400> SEQUENCE: 28

Met Ser Ile Ser Val Asn Gly Gln Ser Val Pro Pro Gly Phe Arg
 1               5                  10                  15

Phe His Pro Thr Glu Glu Glu Leu Leu Thr Tyr Tyr Leu Lys Lys Lys
```

```
            20                  25                  30
Val Ala Ser Glu Arg Ile Asp Leu Asp Val Ile Arg Asp Val Asp Leu
         35                  40                  45

Asn Lys Leu Glu Pro Trp Asp Ile Gln Glu Arg Cys Arg Ile Gly Ser
 50                  55                  60

Gly Pro Gln Asn Asp Trp Tyr Phe Phe Ser His Lys Asp Lys Lys Tyr
 65                  70                  75                  80

Pro Thr Gly Thr Arg Thr Asn Arg Ala Thr Ala Ala Gly Phe Trp Lys
             85                  90                  95

Ala Thr Gly Arg Asp Lys Ala Ile Tyr Ser Ser Ser Asn Arg Ile Gly
            100                 105                 110

Met Arg Lys Thr Leu Val Phe Tyr Lys Gly Arg Ala Pro His Gly Gln
        115                 120                 125

Lys Ser Asp Trp Ile Met His Glu Tyr Arg Leu Asp Asp Pro Ser Ser
        130                 135                 140

Ala Ser Ala Ser Val Ser Val Asn Leu Pro Ser Tyr Tyr Ser Ser Ser
145                 150                 155                 160

Ser Ser Ser Ser Pro Met His Gly Val Ala Gly Asp Gln Gly Ala
                165                 170                 175

Gln Glu Glu Gly Trp Val Ile Cys Arg Val Phe Lys Lys Lys Asn Leu
                180                 185                 190

Val His His Gly Gly Gly Ala Ala Ala Ser His His Ala Ala Ala
            195                 200                 205

Lys Leu Ala Ala Ala Met Glu Gly Ser Pro Ser Asn Cys Ser Thr
    210                 215                 220

Val Thr Val Ser Asp His Val Lys Ala Gln Met Leu His Ser Ser Ala
225                 230                 235                 240

Ser Asp Asp Ala Leu Asp His Ile Leu Gln Tyr Met Gly Arg Ser Gly
                245                 250                 255

Cys Lys Gln Glu Thr Lys Pro Ala Ala Met Ser Ala Ser Ser Ala Ala
                260                 265                 270

Ala Ala Ala Ala Leu Glu Gln His Leu Ser Thr Pro Gln Tyr Gly Lys
            275                 280                 285

Phe Met Lys Leu Pro Pro Leu Glu His Val Ala Gly Gly Val Gly Leu
    290                 295                 300

Leu Ala Ala Ala Gly Gly Gly Glu Tyr Cys Ser Ala Ala Asp Ala
305                 310                 315                 320

Ser Gly Ile Ala Asp Trp Asp Thr Leu Asp Arg Leu Ala Ala Ser Tyr
                325                 330                 335

Glu Leu Asn Gly Ala Leu Ser Asp Val Ala Ser Gly Lys Asn Met Ala
            340                 345                 350

Gly Phe Phe Asp Val Val Asp Gln Pro Ala Gly Ala Ala Ala Phe Ser
            355                 360                 365

Ser Gly Asp Gly Asp Leu Trp Ser Leu Ala Arg Ser Val Ser Ser Ser
    370                 375                 380

Leu His Ala Asp Leu Thr Thr Met Asn Asn Val
385                 390                 395

<210> SEQ ID NO 29
<211> LENGTH: 419
<212> TYPE: PRT
<213> ORGANISM: Sorghum bicolor

<400> SEQUENCE: 29
```

```
Met Ser Ile Ser Val Asn Gly Gln Ser Cys Val Pro Gly Phe Arg
1               5                   10                  15

Phe His Pro Thr Glu Glu Leu Leu Asn Tyr Tyr Leu Arg Lys Lys
                20              25              30

Val Ala Ser Gln Glu Ile Asp Leu Asp Val Ile Arg Asp Val Asp Leu
            35              40              45

Asn Lys Leu Glu Pro Trp Asp Ile Gln Glu Lys Cys Lys Ile Gly Ser
50              55              60

Gly Pro Gln Asn Asp Trp Tyr Phe Phe Ser His Lys Asp Lys Lys Tyr
65              70              75              80

Pro Thr Gly Thr Arg Thr Asn Arg Ala Thr Ala Ala Gly Phe Trp Lys
                85              90              95

Ala Thr Gly Arg Asp Lys Ala Ile Tyr Asn Ala Val Lys Arg Ile Gly
            100             105             110

Met Arg Lys Thr Leu Val Phe Tyr Lys Gly Arg Ala Pro His Gly Gln
            115             120             125

Lys Ser Asp Trp Ile Met His Glu Tyr Arg Leu Asp Asp Pro Ala Ala
    130             135             140

Ser Gly Asp Ala Ala Ala Ala Thr Ala Ala Ala Ala Ala Thr Val
145             150             155             160

Ala Ala Ala Ala Ala Ser Ser Asp Gly Gly Gln Glu Asp Ala Trp Val
                165             170             175

Val Tyr Arg Val Phe Lys Lys Lys His His Lys Glu Ser Ser Gly
            180             185             190

Gly Gly Gly Gly Ser Lys His Gly Gly Ser Asn Asn Glu His Gly His
            195             200             205

Gly Gly Gly Lys Ala Ala Ala Ala Ala Ala Ala His Gln His
210             215             220

His Gly Gly Leu Gln Tyr Ser Ser Ser Asp Asp Ala Leu Asp Gln Ile
225             230             235             240

Leu Gln Tyr Met Gly Arg Ser Cys Lys Gln Glu His Glu Leu Leu Ser
                245             250             255

Pro Pro Pro Pro Gly Arg Ala Ala Ser Arg Tyr Leu Arg Pro Ile Glu
                260             265             270

Thr Val Leu Gly Gly His Gly Phe Met Lys Leu Pro Pro Leu Glu Ser
            275             280             285

Pro Ser Ala Ala Ala Ala Met Thr Pro Gln Ala Val Ser Gly Asp Ala
    290             295             300

Gly Val Val Asp Asp Leu Leu Gly Leu His Arg Gly Gly Ile Gly Asn
305             310             315             320

Gly Ile Thr Asp Trp Ala Met Met Asp Arg Leu Val Ala Ser His Leu
            325             330             335

Asn Gly Gln Glu Ala Pro Asp Val Ala Pro Ala Ala Asp Gln Leu Gly
            340             345             350

Ser Cys Phe Asp Asp Ala Thr Gly Ala Asp Ala Asp Ala Ala Gly
    355             360             365

Leu Ala Phe Tyr Ser Ala Ala Ala Asn Arg Leu Leu Val Gly Ser Ala
    370             375             380

Gly Ser Ser Gly Ala Gly Ser Asp Asp Asp Leu Trp Ser Phe Thr Arg
385             390             395             400

Ser Ser Ala Ala Ala Ala Ala Ala Thr Ser Thr Glu Arg Leu Ser His
            405             410             415

Val Ser Leu
```

```
<210> SEQ ID NO 30
<211> LENGTH: 428
<212> TYPE: PRT
<213> ORGANISM: Sorghum bicolor

<400> SEQUENCE: 30

Met Ser Ile Ser Val Asn Gly Gln Ser Val Pro Pro Gly Phe Arg
1               5                   10                  15

Phe His Pro Thr Glu Glu Leu Leu Thr Tyr Tyr Leu Lys Lys Lys
                20                  25                  30

Val Ala Ser Glu Arg Ile Asp Leu Asp Val Ile Arg Asp Val Asp Leu
            35                  40                  45

Asn Lys Leu Glu Pro Trp Asp Ile Gln Glu Lys Cys Arg Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Gly Phe Trp Lys
                85                  90                  95

Ala Thr Gly Arg Asp Lys Ala Ile Tyr Ala Ser Gly Ala Arg Arg Ile
                100                 105                 110

Gly Met Arg Lys Thr Leu Val Phe Tyr Lys Gly Arg Ala Pro His Gly
                115                 120                 125

Gln Lys Ser Asp Trp Ile Met His Glu Tyr Arg Leu Glu Pro Ala Leu
                130                 135                 140

Asp Val Asp Ala Ala Ala Gly Ser Ala Ser Ala His His Ala Ala Ala
145                 150                 155                 160

Gly Ala Ala Ala Asp His His Pro Tyr Tyr Thr Ser Ser Ser Pro Pro
                165                 170                 175

Ala Leu Pro Thr Ala Ile Arg Gly Ala Ala Gly Asp Gln Gln Ala Ala
                180                 185                 190

Gln Glu Gln Glu Gly Trp Val Ile Cys Arg Val Phe Lys Lys Lys Asn
                195                 200                 205

Leu Val His His Gly Gln Ser Ser Gly Gly Val Thr Ala Ala Gly
                210                 215                 220

Ser Lys Met Ala Ser Ala Ala Pro Met Glu Gly Ser Pro Ser His
225                 230                 235                 240

Cys Ser Ser Val Thr Val Ile Ser Asp His Thr Met Asn Lys His Gln
                245                 250                 255

Ala Gln Ala Met Leu Gln His Ser Ala Ser Asp Asp Asp Ala Leu Asp
                260                 265                 270

His Ile Leu Gln Tyr Met Gly Gly Gly Gly Lys Gln Pro Asp Thr
                275                 280                 285

Lys Pro Val Leu Leu Asp His His His His His Leu Ala Ala Ala
                290                 295                 300

Ala Thr Thr Thr Thr Thr Ala Cys Ser Ala Gly Gly Ala Gly Leu Tyr
305                 310                 315                 320

Gly Lys Phe Met Lys Leu Pro Pro Leu Glu His Ala Gly Gly Gly
                325                 330                 335

Gly Leu Leu Pro Ser Pro Ala Gly Ala Cys Asp Tyr Gly Ala Ala Asp
                340                 345                 350

Ala Ser Gly Ile Ala Asp Trp Asp Ala Leu Asp Arg Leu Ala Ala Tyr
                355                 360                 365

Glu Leu Asn Gly Leu Ser Asp Ala Ser Lys Asn Met Ser Ala Phe Phe
```

```
            370                 375                 380
Asp Glu Pro Ser Ala Thr Ala Ala Phe Ser Ser Ser Ser Ser Val
385                 390                 395                 400

His Ala Ala Val Asp Gly Asp Leu Trp Ser Leu Ala Arg Ser Val
                405                 410                 415

Ser Ala Leu His Ala Asp Leu Thr Met Asn Asn Val
                420                 425

<210> SEQ ID NO 31
<211> LENGTH: 388
<212> TYPE: PRT
<213> ORGANISM: Glycine max

<400> SEQUENCE: 31

Met Pro Glu Asn Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
                20                  25                  30

Leu Arg Lys Lys Val Ser Tyr Glu Lys Ile Asp Leu Asp Val Ile Arg
                35                  40                  45

Asp Val Asp Leu Asn Lys Leu Glu Pro Trp Asp Ile Gln Glu Lys Cys
50                  55                  60

Lys Ile Gly Thr Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Val Ile Tyr Ser Asn Gly
                100                 105                 110

Lys Arg Ile Gly Met Arg Lys Thr Leu Val Phe Tyr Lys Gly Arg Ala
                115                 120                 125

Pro His Gly Gln Lys Ser Asp Trp Ile Met His Glu Tyr Arg Leu Asp
130                 135                 140

Asp Asn Asn Thr Ser Asp Ile Asn Ile Val Ser Asn Val Met Gly Asp
145                 150                 155                 160

Ala Ala Gln Glu Glu Gly Trp Val Val Cys Arg Ile Phe Lys Lys Lys
                165                 170                 175

Asn His Leu Lys Thr Leu Asp Ser Pro Leu Ala Ser Gly Glu Gly Arg
                180                 185                 190

Arg Ser His Met Phe Asp Ser Cys Asp Glu Gly Ala Leu Glu Gln Ile
                195                 200                 205

Leu Gln Gln Met Gly Arg Gly Cys Lys Glu Glu Ser Ser Tyr Glu Gly
                210                 215                 220

Asn Tyr Asn Ser Tyr Gly Arg Phe Ala Met Gly Leu Asn Asn Gly Gly
225                 230                 235                 240

Gly Gly Gly Tyr Asn Asp Arg Phe Met Lys Leu Pro Ser Leu Glu Ser
                245                 250                 255

Pro Lys Ser Ala Ser Met Glu Asn His His Asn Thr Asn Asn Asn Cys
                260                 265                 270

Asn Asn Asn Met Lys Ser Gly Gly Leu Thr Asn Trp Ala Ala Leu
                275                 280                 285

Asp Arg Leu Val Ala Ser Gln Leu Asn Gly Gln Thr Asp Ala Ser Arg
                290                 295                 300

Gln Leu Gly Cys Ala Phe Asn Asp Pro Thr Met Tyr Cys Thr Ser Val
305                 310                 315                 320
```

-continued

Asp His His Asp Leu His His Gln Ile Pro Thr Leu Arg Ser Ser Ser
            325                 330                 335

Thr Ser Ala Asn Thr Arg Pro Ser Pro Ala Pro Ala Phe Ile Asn Pro
        340                 345                 350

Pro Thr Gln Asp Phe Thr Ser Glu Ile Asp Leu Trp Asn Phe Ser Arg
    355                 360                 365

Ser Thr Ser Ser Leu Leu Ala Ser Ser Glu Pro Leu Cys His Val Ser
370                 375                 380

Asn Thr Ser Val
385

<210> SEQ ID NO 32
<211> LENGTH: 419
<212> TYPE: PRT
<213> ORGANISM: Glycine max

<400> SEQUENCE: 32

Met Pro Glu Asn Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
            20                  25                  30

Leu Arg Lys Lys Val Ser Tyr Glu Lys Ile Asp Leu Asp Val Ile Arg
        35                  40                  45

Asp Val Asp Leu Asn Lys Leu Glu Pro Trp Asp Ile Gln Glu Lys Cys
    50                  55                  60

Lys Ile Gly Thr Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Val Ile Tyr Ser Asn Gly
            100                 105                 110

Lys Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Asp
    130                 135                 140

Asp Asn Asn Thr Ala Asp Thr Asn Ile Val Ser Asn Val Met Gly Asp
145                 150                 155                 160

Ala Ala Gln Glu Glu Gly Trp Val Val Cys Arg Ile Phe Lys Lys Lys
                165                 170                 175

Asn His Leu Lys Thr Leu Asp Ser Pro Leu Ala Ser Gly Glu Asp Arg
            180                 185                 190

Arg Ser His Leu Phe Asp Ser Cys Asp Glu Gly Ala Leu Glu Gln Ile
        195                 200                 205

Leu Glu Gln Met Gly Arg Ser Cys Lys Glu Glu Ser Ser Tyr Glu Gly
    210                 215                 220

Asn Tyr Arg Asn Tyr Gly Arg Phe Thr Arg Pro Tyr Glu Thr Thr Gly
225                 230                 235                 240

Leu Asn Asn Gly Gly Gly Tyr Asn Asp Arg Phe Met Lys Leu Pro Ser
                245                 250                 255

Leu Glu Ser Pro Lys Ser Ala Ser Met Glu Ser His Asn Thr Asn
            260                 265                 270

Asn Asn Asn Asn Met Asn Ser Asn Asn Asn Gly Asp Asn Asn
        275                 280                 285

Glu Asn Asn Asn Asn Gly Tyr His Pro Met Ile Pro Val Glu Met
    290                 295                 300

```
Gly Thr Asp Asn Glu Gly Ser Phe Thr Thr His Gln Val Ser Gly Gly
305                 310                 315                 320

Asp Pro Asn Asn Asn Asn Asn Met Val His Pro Leu Glu Val Gly
                325                 330                 335

Ser Gly Gly Gly Leu Thr Asn Trp Ala Ala Leu Asp Arg Leu Val
            340                 345                 350

Ala Ser Gln Leu Asn Gly Gln Thr Asp Ala Ser Arg Gln Leu Ala Cys
                355                 360                 365

Ala Phe Asn Asp Pro Thr Met Tyr Cys Thr Thr Phe Ile Asn Pro Thr
370                 375                 380

Thr Gln Asp Phe Thr Ser Glu Ile Asp Leu Trp Asn Phe Thr Arg Ser
385                 390                 395                 400

Thr Ser Ser Leu Leu Ala Ser Ser Glu Pro Leu Cys His Val Ser Asn
                405                 410                 415

Thr Ser Val

<210> SEQ ID NO 33
<211> LENGTH: 365
<212> TYPE: PRT
<213> ORGANISM: Arabidopsis thaliana

<400> SEQUENCE: 33

Met Met Ser Lys Ser Met Ser Ile Ser Val Asn Gly Gln Ser Gln Val
1               5                   10                  15

Pro Pro Gly Phe Arg Phe His Pro Thr Glu Glu Glu Leu Leu Gln Tyr
                20                  25                  30

Tyr Leu Arg Lys Lys Val Asn Ser Ile Glu Ile Asp Leu Asp Val Ile
            35                  40                  45

Arg Asp Val Asp Leu Asn Lys Leu Glu Pro Trp Asp Ile Gln Glu Met
50                  55                  60

Cys Lys Ile Gly Thr Thr Pro Gln Asn Asp Trp Tyr Phe Phe Ser His
65                  70                  75                  80

Lys Asp Lys Lys Tyr Pro Thr Gly Thr Arg Thr Asn Arg Ala Thr Ala
                85                  90                  95

Ala Gly Phe Trp Lys Ala Thr Gly Arg Asp Lys Ile Ile Tyr Ser Asn
            100                 105                 110

Gly Arg Arg Ile Gly Met Arg Lys Thr Leu Val Phe Tyr Lys Gly Arg
        115                 120                 125

Ala Pro His Gly Gln Lys Ser Asp Trp Ile Met His Glu Tyr Arg Leu
    130                 135                 140

Asp Asp Asn Ile Ile Ser Pro Glu Asp Val Thr Val His Glu Val Val
145                 150                 155                 160

Ser Ile Ile Gly Glu Ala Ser Gln Asp Glu Gly Trp Val Val Cys Arg
                165                 170                 175

Ile Phe Lys Lys Lys Asn Leu His Lys Thr Leu Asn Ser Pro Val Gly
            180                 185                 190

Gly Ala Ser Leu Ser Gly Gly Asp Thr Pro Lys Thr Thr Ser Ser
        195                 200                 205

Gln Ile Phe Asn Glu Asp Thr Leu Asp Gln Phe Leu Glu Leu Met Gly
    210                 215                 220

Arg Ser Cys Lys Glu Glu Leu Asn Leu Asp Pro Phe Met Lys Leu Pro
225                 230                 235                 240

Asn Leu Glu Ser Pro Asn Ser Gln Ala Ile Asn Asn Cys His Val Ser
                245                 250                 255
```

```
Ser Pro Asp Thr Asn His Asn Ile His Val Ser Asn Val Val Asp Thr
            260                 265                 270

Ser Phe Val Thr Ser Trp Ala Ala Leu Asp Arg Leu Val Ala Ser Gln
            275                 280                 285

Leu Asn Gly Pro Thr Ser Tyr Ser Ile Thr Ala Val Asn Glu Ser His
            290                 295                 300

Val Gly His Asp His Leu Ala Leu Pro Ser Val Arg Ser Pro Tyr Pro
305                 310                 315                 320

Ser Leu Asn Arg Ser Ala Ser Tyr His Ala Gly Leu Thr Gln Glu Tyr
            325                 330                 335

Thr Pro Glu Met Glu Leu Trp Asn Thr Thr Thr Ser Ser Leu Ser Ser
            340                 345                 350

Ser Pro Gly Pro Phe Cys His Val Ser Asn Gly Ser Gly
            355                 360                 365

<210> SEQ ID NO 34
<211> LENGTH: 358
<212> TYPE: PRT
<213> ORGANISM: Arabidopsis thaliana

<400> SEQUENCE: 34

Met Ala Asp Asn Lys Val Asn Leu Ser Ile Asn Gly Gln Ser Lys Val
1               5                   10                  15

Pro Pro Gly Phe Arg Phe His Pro Thr Glu Glu Glu Leu Leu His Tyr
            20                  25                  30

Tyr Leu Arg Lys Lys Val Asn Ser Gln Lys Ile Asp Leu Asp Val Ile
            35                  40                  45

Arg Glu Val Asp Leu Asn Lys Leu Glu Pro Trp Asp Ile Gln Glu Glu
        50                  55                  60

Cys Arg Ile Gly Ser Thr Pro Gln Asn Asp Trp Tyr Phe Phe Ser His
65                  70                  75                  80

Lys Asp Lys Lys Tyr Pro Thr Gly Thr Arg Thr Asn Arg Ala Thr Val
                85                  90                  95

Ala Gly Phe Trp Lys Ala Thr Gly Arg Asp Lys Ile Ile Cys Ser Cys
            100                 105                 110

Val Arg Arg Ile Gly Leu Arg Lys Thr Leu Val Phe Tyr Lys Gly Arg
            115                 120                 125

Ala Pro His Gly Gln Lys Ser Asp Trp Ile Met His Glu Tyr Arg Leu
            130                 135                 140

Asp Asp Thr Pro Met Ser Asn Gly Tyr Ala Asp Val Val Thr Glu Asp
145                 150                 155                 160

Pro Met Ser Tyr Asn Glu Glu Gly Trp Val Val Cys Arg Val Phe Arg
                165                 170                 175

Lys Lys Asn Tyr Gln Lys Ile Asp Asp Cys Pro Lys Ile Thr Leu Ser
            180                 185                 190

Ser Leu Pro Asp Asp Thr Glu Glu Lys Gly Pro Thr Phe His Asn
            195                 200                 205

Thr Gln Asn Val Thr Gly Leu Asp His Val Leu Leu Tyr Met Asp Arg
            210                 215                 220

Thr Gly Ser Asn Ile Cys Met Pro Glu Ser Gln Thr Thr Thr Gln His
225                 230                 235                 240

Gln Asp Asp Val Leu Phe Met Gln Leu Pro Ser Leu Glu Thr Pro Lys
                245                 250                 255

Ser Glu Ser Pro Val Asp Gln Ser Phe Leu Thr Pro Ser Lys Leu Asp
```

```
            260                 265                 270
Phe Ser Pro Val Gln Glu Lys Ile Thr Glu Arg Pro Val Cys Ser Asn
        275                 280                 285

Trp Ala Ser Leu Asp Arg Leu Val Ala Trp Gln Leu Asn Asn Gly His
    290                 295                 300

His Asn Pro Cys His Arg Lys Ser Phe Asp Glu Glu Glu Asn Gly
305                 310                 315                 320

Asp Thr Met Met Gln Arg Trp Asp Leu His Trp Asn Asn Asp Asp Asn
                325                 330                 335

Val Asp Leu Trp Ser Ser Phe Thr Glu Ser Ser Ser Leu Asp Pro
            340                 345                 350

Leu Leu His Leu Ser Val
        355

<210> SEQ ID NO 35
<211> LENGTH: 334
<212> TYPE: PRT
<213> ORGANISM: Arabidopsis thaliana

<400> SEQUENCE: 35

Met Asn Ile Ser Val Asn Gly Gln Ser Gln Val Pro Pro Gly Phe Arg
1               5                   10                  15

Phe His Pro Thr Glu Glu Leu Leu Lys Tyr Tyr Leu Arg Lys Lys
            20                  25                  30

Ile Ser Asn Ile Lys Ile Asp Leu Asp Val Ile Pro Asp Ile Asp Leu
        35                  40                  45

Asn Lys Leu Glu Pro Trp Asp Ile Gln Glu Met Cys Lys Ile Gly Thr
    50                  55                  60

Thr Pro Gln Asn Asp Trp Tyr Phe Tyr Ser His Lys Asp Lys Lys Tyr
65                  70                  75                  80

Pro Thr Gly Thr Arg Thr Asn Arg Ala Thr Thr Val Gly Phe Trp Lys
                85                  90                  95

Ala Thr Gly Arg Asp Lys Thr Ile Tyr Thr Asn Gly Asp Arg Ile Gly
            100                 105                 110

Met Arg Lys Thr Leu Val Phe Tyr Lys Gly Arg Ala Pro His Gly Gln
        115                 120                 125

Lys Ser Asp Trp Ile Met His Glu Tyr Arg Leu Asp Glu Ser Val Leu
    130                 135                 140

Ile Ser Ser Cys Gly Asp His Asp Val Asn Val Glu Thr Cys Asp Val
145                 150                 155                 160

Ile Gly Ser Asp Glu Gly Trp Val Val Cys Arg Val Phe Lys Lys Asn
                165                 170                 175

Asn Leu Cys Lys Asn Met Ile Ser Ser Pro Ala Ser Ser Val Lys
            180                 185                 190

Thr Pro Ser Phe Asn Glu Glu Thr Ile Glu Gln Leu Leu Glu Val Met
        195                 200                 205

Gly Gln Ser Cys Lys Gly Glu Ile Val Leu Asp Pro Phe Leu Lys Leu
    210                 215                 220

Pro Asn Leu Glu Cys His Asn Asn Thr Thr Ile Thr Ser Tyr Gln Trp
225                 230                 235                 240

Leu Ile Asp Asp Gln Val Asn Asn Cys His Val Ser Lys Val Met Asp
                245                 250                 255

Pro Ser Phe Ile Thr Ser Trp Ala Ala Leu Asp Arg Leu Val Ala Ser
            260                 265                 270
```

```
Gln Leu Asn Gly Pro Asn Ser Tyr Ser Ile Pro Ala Val Asn Glu Thr
        275                 280                 285

Ser Gln Ser Pro Tyr His Gly Leu Asn Arg Ser Gly Cys Asn Thr Gly
    290                 295                 300

Leu Thr Pro Asp Tyr Tyr Ile Pro Glu Ile Asp Leu Trp Asn Glu Ala
305                 310                 315                 320

Asp Phe Ala Arg Thr Thr Cys His Leu Leu Asn Gly Ser Gly
                325                 330

<210> SEQ ID NO 36
<211> LENGTH: 379
<212> TYPE: PRT
<213> ORGANISM: Zea mays

<400> SEQUENCE: 36

Met Ser Ile Ser Val Asn Gly Gln Ser Cys Val Pro Pro Gly Phe Arg
1               5                  10                  15

Phe His Pro Thr Glu Glu Leu Leu Asn Tyr Tyr Leu Arg Lys Lys
            20                  25                  30

Val Ala Ser Gln Gln Ile Asp Leu Asp Val Ile Arg Asp Val Asp Leu
        35                  40                  45

Asn Lys Leu Glu Pro Trp Asp Ile Gln Glu Arg Cys Lys Ile Gly Ser
    50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
                85                  90                  95

Ala Thr Gly Arg Asp Lys Ala Ile Tyr Ser Ala Val Arg Arg Met Gly
            100                 105                 110

Met Arg Lys Thr Leu Val Phe Tyr Arg Gly Arg Ala Pro His Gly His
        115                 120                 125

Lys Ser Asp Trp Ile Met His Glu Tyr Arg Leu Asp Asp Pro Asp Ala
    130                 135                 140

Ala Ala Val Ala Ala Thr Val Ala Ala Ala Ala Ser Ser Asp Gly
145                 150                 155                 160

Gly Gln Glu Asp Gly Trp Val Val Cys Arg Val Phe Gln Lys Lys His
                165                 170                 175

His His Lys Glu Ser Ser Gly Arg Cys Arg Ser Lys Arg Gly Ser Lys
            180                 185                 190

Thr Glu His Gly His Gly Glu Ala Lys Thr Ala Ala His Gln Arg His
        195                 200                 205

Gly Cys Gly Leu Gln Tyr Ser Ser Asn Asp Asp Thr Leu Asp His Met
    210                 215                 220

Leu Gly Arg Arg Ser Cys Lys Gln Glu His Leu Leu Pro Leu Pro
225                 230                 235                 240

Pro Pro Ala Ala Ala Arg Ala Ala Ser Arg Tyr Ile Arg Pro Ile Glu
                245                 250                 255

Thr Val Leu Gly Gly His Gly Phe Met Lys Leu Pro Pro Leu Glu Ser
            260                 265                 270

Pro Ala Ala Ala Glu Ala Leu Thr Thr Pro His Ala Val Ser Ala Gly
        275                 280                 285

Asp Ala Thr Ala Ala Gly Ala Leu Asp Gly Leu His Arg Ala Gly Asn
    290                 295                 300

Gly Ile Thr Asp Trp Val Met Met Asp Arg Met Val Ala Leu His Leu
305                 310                 315                 320
```

-continued

Asn Gly Gln Ala Pro Ala Ala Asp Gln Leu Gly Ser Cys Phe Asp Ala
            325                 330                 335

Ser Ala Asp Gly Gly Leu Ala Cys Phe Tyr Ser Ala Ala Ala Asn
            340                 345                 350

Arg Leu Leu Gly Gly Asp Asp Leu Trp Ser Phe Thr Arg Ser
            355                 360                 365

Ser Ser Thr Glu Arg Leu Gly His Val Ser Leu
    370                 375

<210> SEQ ID NO 37
<211> LENGTH: 435
<212> TYPE: PRT
<213> ORGANISM: Zea mays

<400> SEQUENCE: 37

Met Ser Ile Ser Val Asn Gly Gln Ser Val Pro Pro Gly Phe Arg
1               5                  10                  15

Phe His Pro Thr Glu Glu Leu Leu Thr Tyr Tyr Leu Lys Lys Lys
            20                  25                  30

Val Ala Ser Glu Arg Ile Asp Leu Asp Val Ile Arg Asp Val Asp Leu
            35                  40                  45

Asn Lys Leu Glu Pro Trp Asp Ile Gln Glu Lys Cys Arg Ile Gly Ser
50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Ala Gly Phe Trp Lys
            85                  90                  95

Ala Thr Gly Arg Asp Lys Ala Ile Tyr Ala Ser Pro Gly Ala Arg Arg
            100                 105                 110

Ile Gly Met Arg Lys Thr Leu Val Phe Tyr Lys Gly Arg Ala Pro His
            115                 120                 125

Gly Gln Lys Ser Asp Trp Ile Met His Glu Tyr Arg Leu Glu Ala Pro
            130                 135                 140

Val Asp Ala Gly Ala Gly Ala Ala His His Leu Leu Leu Pro Ala Ala
145                 150                 155                 160

Glu His Pro Pro Tyr Tyr Thr Ser Pro Pro Gln Ala Pro Ser Ser Thr
            165                 170                 175

Thr Thr Ala Thr Ile Arg Gly Ala Ala Gly Asp Gln Ala Ala Gln Glu
            180                 185                 190

Gln Glu Gly Trp Val Ile Cys Arg Val Phe Lys Lys Lys Asn Leu Val
            195                 200                 205

His His Gly Gln Ser Ser Gly Val Lys Gln Gln Ala Ala Gly Asp Asp
            210                 215                 220

His Ala Ala Ser His Thr Ala Ala Ala Ala His Met Asp Glu Ser
225                 230                 235                 240

Ser Pro Ser Gln Cys Ser Ser Val Thr Val Ile Ser Asp His Val His
            245                 250                 255

Ala Asn Val Asn Asp Lys Gln Gln Ala Gln Ala Ser Leu Leu Met
            260                 265                 270

Met His Thr His His Ser Ala Ser Ser Asp Asp Ala Leu Asp His
            275                 280                 285

Ile Leu Gln Gln Tyr Met Gly Gly Gly Arg Gln Ala Pro Ala Pro Asp
            290                 295                 300

Thr Lys Pro Ala Leu Leu Glu Gln Leu Asp His Leu His His His Leu

```
            305                 310                 315                 320
Ala Ala Ala Pro Thr Thr Arg Ala Ala Gly Phe Tyr Tyr Gly Lys
            325                 330                 335

Phe Met Lys Leu Pro Pro Leu Glu His Ala Gly Leu Pro Pro Ser Pro
            340                 345                 350

Pro Pro Pro Gly Ala Arg Glu Tyr Gly Ala Ala Ala Ala Gly Trp
            355                 360                 365

Asp Asp Asp Asp Asp Ala Leu Asp Arg Leu Ala Ala Tyr Asp His Leu
370                 375                 380

Asn Gly Leu Ser Asn Asp Ala Ser Lys Asn Met Ala Ala Phe Phe Asp
385                 390                 395                 400

Val Glu Pro Ser Ala Ala Ala Ala Ala Val Asp Gly Asp Leu Trp
            405                 410                 415

Ser Leu Ala Arg Ser Val Ser Ala Leu His Ala Asp Leu Thr Met Asn
            420                 425                 430

Asn Asn Val
        435

<210> SEQ ID NO 38
<211> LENGTH: 408
<212> TYPE: PRT
<213> ORGANISM: Brachypodium distachyon

<400> SEQUENCE: 38

Met Ser Ile Ser Val Asn Gly Gln Ser Cys Val Pro Pro Gly Phe Arg
1               5                   10                  15

Phe His Pro Thr Glu Glu Leu Leu Asn Tyr Tyr Leu Arg Lys Lys
            20                  25                  30

Val Ala Ser Gln Gln Ile Asp Leu Asp Val Ile Arg Asp Val Asp Leu
            35                  40                  45

Asn Lys Leu Glu Pro Trp Asp Ile Gln Glu Arg Cys Lys Ile Gly Ser
        50                  55                  60

Gly Pro Gln Asn Asp Trp Tyr Phe Phe Ser His Lys Asp Lys Lys Tyr
65                  70                  75                  80

Pro Thr Gly Thr Arg Thr Asn Arg Ala Thr Ala Gly Phe Trp Lys
            85                  90                  95

Ala Thr Gly Arg Asp Lys Ala Ile Tyr Asn Ala Val Ser Arg Ile Gly
            100                 105                 110

Met Arg Lys Thr Leu Val Phe Tyr Lys Gly Arg Ala Pro His Gly Leu
        115                 120                 125

Lys Ser Asp Trp Ile Met His Glu Tyr Arg Leu Leu Asp Ala Asp Asp
        130                 135                 140

Ser Ser Ser Ala Ala Thr Ala Met Val Arg Val Ser Val Thr Ala
145                 150                 155                 160

Ser Ser Val Ala Ala Ser Glu Ala Ala Gly Gln Gln Gly Pro Glu Asp
            165                 170                 175

Gly Trp Val Val Cys Arg Val Phe Lys Lys His His His Lys Asp
            180                 185                 190

Thr Asn Ser Gly Ser Gly Ser Gly Ser Gly Asn Lys Lys Ala Ala Ala
        195                 200                 205

Leu Arg Arg Ser Ser Ser Ser Pro Leu Tyr Ser Ser Gly Asp Asp Ala
        210                 215                 220

Ala Leu Asp Gln Ile Leu His Tyr Met Gly Arg Ser Ser Ala Ala Cys
225                 230                 235                 240
```

```
Lys Gln Glu His Asp Ser Pro Arg Pro Ala Pro Gln Thr Gln Ala
                245                 250                 255

Gln Ala Arg Pro Thr Ser Arg Tyr Leu Arg Pro Ile Glu Thr Ala Leu
            260                 265                 270

Ala Gly Gly His Gly Phe Met Lys Leu Pro Pro Leu Glu Ser Pro Ser
        275                 280                 285

Ser Ala Ala Ala Ala Pro Pro Asn Thr Thr Pro Val Pro Glu Thr
290                 295                 300

Thr Met Asp Trp Ala Met Met Asp Arg Leu Val Ala Ser His Leu Asn
305                 310                 315                 320

Gly Gln Leu His Asp Asp His Ala Ser Thr Ala Val Val Asp Asp
            325                 330                 335

His Arg Leu Cys Ser Ala Phe Asp Asp Gly Ala Gly Glu Asp Asn Asp
            340                 345                 350

Asp Gly Glu Met Ala Gly Pro Asp Val Glu Arg Pro Val Gly Glu Pro
        355                 360                 365

Ser Arg Gly Ser Ser Ala Ala Gln Leu Ala Val Asn Arg Pro Ser Trp
    370                 375                 380

Lys Lys Lys Val Ser Phe Arg Pro Arg Gly Gly Pro Pro Leu Val Pro
385                 390                 395                 400

Thr Val Pro Val Asp Gly Gly Gly
                405

<210> SEQ ID NO 39
<211> LENGTH: 405
<212> TYPE: PRT
<213> ORGANISM: Vitis vinifera

<400> SEQUENCE: 39

Met Ser Glu Asp Met Asn Leu Ser Val Asn Gly Gln Ser Gln Val Pro
1               5                   10                  15

Pro Gly Phe Arg Phe His Pro Thr Glu Glu Glu Leu Leu His Tyr Tyr
            20                  25                  30

Leu Arg Lys Lys Val Ala Tyr Glu Lys Ile Asp Leu Asp Val Ile Arg
        35                  40                  45

Asp Val Asp Leu Asn Lys Leu Glu Pro Trp Asp Ile Gln Glu Lys Cys
    50                  55                  60

Lys Ile Gly Ser Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Val Ile Tyr Ser Ser Phe
            100                 105                 110

Arg Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Glu
    130                 135                 140

Glu Asn Thr Pro Val His Asp Thr Met Ala Ser Asn Ser Leu Gly Glu
145                 150                 155                 160

Ser Met Pro Glu Asp Gly Trp Val Val Cys Arg Val Phe Arg Lys Lys
                165                 170                 175

Asn Tyr Gln Lys Thr Leu Glu Ser Pro Lys Ser Thr Ser Asn Ser Met
            180                 185                 190

Asp Ser Arg Thr Gln Met Leu Asn Ser Ser Asn Asp Gly Val Leu Asp
        195                 200                 205
```

```
Gln Ile Leu Ser Tyr Met Gly Arg Thr Cys Lys Gln Glu Asn Glu Ala
    210                 215                 220

Ile Ser Asn Val Asn Phe Ser Asp Ser Asn Asn Thr Met Arg Phe Leu
225                 230                 235                 240

Asn Gln Asn Asn Thr Gly Ile Ser Glu Gly Leu Gln Glu Arg Phe Met
                245                 250                 255

His Leu Pro Arg Leu Glu Ser Pro Thr Leu Pro Ser Leu Pro Asn Asn
            260                 265                 270

Ser Ser His Phe Asp Gln Glu Arg Cys Phe Asn Ile Ala Cys Leu Gln
        275                 280                 285

Ser Ile Asp Glu Met Leu Arg Gly Ser Glu Pro Ser Glu Asn Gln
        290                 295                 300

Gly Ser Gly Cys Asn Thr Thr Pro Val His Asp Pro Lys Ala Gly Leu
305                 310                 315                 320

Asn Asp Trp Val Ala Phe Asp Arg Leu Val Ala Ser Gln Leu Asn Gly
                325                 330                 335

Gln Val Asp Thr Lys Gln Leu Ser Cys Phe Ser Thr Asp Pro Asn Met
                340                 345                 350

Gly Phe Cys Leu Ser Pro Asp His Asp Val Glu Leu Ser His Leu Arg
            355                 360                 365

Ser Ser Arg Pro Asn Pro Asn Pro Gln Asn Tyr Asn Ser Glu Met Asp
370                 375                 380

Leu Trp Asn Phe Thr Arg Ser Ser Ser Ser Ser Ser Asp Pro Leu
385                 390                 395                 400

Gly His Leu Ser Val
                405

<210> SEQ ID NO 40
<211> LENGTH: 400
<212> TYPE: PRT
<213> ORGANISM: Glycine max

<400> SEQUENCE: 40

Met Pro Glu Asn Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
            20                  25                  30

Leu Arg Lys Lys Val Ser Tyr Glu Lys Ile Asp Leu Asp Val Ile Arg
        35                  40                  45

Asp Val Asp Leu Asn Lys Leu Glu Pro Trp Asp Ile Gln Glu Lys Cys
50                  55                  60

Lys Ile Gly Thr Thr Pro Gln Asn Asp Trp Tyr Phe Phe Ser His Lys
65                  70                  75                  80

Asp Lys Lys Tyr Pro Thr Gly Thr Arg Thr Asn Arg Ala Thr Ala Ala
                85                  90                  95

Gly Phe Trp Lys Ala Thr Gly Arg Asp Lys Val Ile Tyr Ser Asn Gly
            100                 105                 110

Lys Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Asp
    130                 135                 140

Asp Asn Asn Thr Ala Asp Thr Asn Ile Val Ser Asn Val Met Gly Asp
145                 150                 155                 160

Ala Ala Gln Glu Glu Gly Trp Val Val Cys Arg Ile Phe Lys Lys Lys
```

```
                    165                 170                 175
Asn His Leu Lys Thr Leu Asp Ser Pro Leu Ala Ser Gly Glu Asp Arg
            180                 185                 190

Arg Ser His Leu Phe Asp Ser Cys Asp Glu Gly Ala Leu Glu Gln Ile
        195                 200                 205

Leu Glu Gln Met Gly Arg Ser Cys Lys Glu Glu Ser Ser Tyr Glu Gly
    210                 215                 220

Asn Tyr Arg Asn Tyr Gly Arg Phe Thr Arg Pro Tyr Glu Thr Thr Gly
225                 230                 235                 240

Leu Asn Asn Gly Gly Gly Tyr Asn Asp Arg Phe Met Lys Leu Pro Ser
                245                 250                 255

Leu Glu Ser Pro Lys Ser Ala Ser Met Glu Ser His His Asn Thr Asn
            260                 265                 270

Asn Asn Asn Asn Met Asn Ser Asn Asn Asn Asn Gly Asp Asn Asn
        275                 280                 285

Glu Asn Asn Asn Asn Gly Tyr His Pro Met Ile Pro Val Glu Met
    290                 295                 300

Gly Thr Asp Asn Glu Gly Ser Phe Thr Thr His Gln Val Ser Gly Gly
305                 310                 315                 320

Asp Pro Asn Asn Asn Asn Asn Met Val His Pro Leu Glu Val Gly
                325                 330                 335

Ser Gly Gly Gly Leu Thr Asn Trp Ala Ala Leu Asp Arg Leu Val
            340                 345                 350

Ala Ser Gln Leu Asn Gly Gln Thr Asp Ala Ser Arg Gln Leu Ala Cys
        355                 360                 365

Ala Phe Asn Asp Pro Thr Met Tyr Cys Thr Ser Asp His His Asp Leu
    370                 375                 380

His Gln Ile Pro Thr Leu Arg Ser Ser Thr Ser Ala Ala His Thr
385                 390                 395                 400

<210> SEQ ID NO 41
<211> LENGTH: 389
<212> TYPE: PRT
<213> ORGANISM: Gossypium hirsutum

<400> SEQUENCE: 41

Met Asn Leu Ser Ile Asn Gly Gln Ser Gln Val Pro Pro Gly Phe Arg
1               5                   10                  15

Phe His Pro Thr Glu Glu Leu Leu His Tyr Tyr Leu Arg Lys Lys
            20                  25                  30

Val Ala Tyr Glu Lys Ile Asp Leu Asp Val Ile Gln Glu Val Asp Leu
        35                  40                  45

Asn Lys Leu Glu Pro Trp Asp Ile Gln Glu Lys Cys Arg Ile Gly Ser
    50                  55                  60

Thr Pro Gln Asn Glu Trp Tyr Phe Phe Ser His Lys Asp Lys Tyr
65                  70                  75                  80

Pro Thr Gly Thr Arg Thr Asn Arg Ala Thr Ala Gly Phe Trp Lys
                85                  90                  95

Ala Thr Gly Arg Asp Lys Ile Ile Tyr Ser Gly Phe Arg Ile Gly
            100                 105                 110

Leu Arg Lys Thr Leu Val Phe Tyr Lys Gly Arg Ala Pro His Gly Gln
        115                 120                 125

Lys Ser Asp Trp Ile Met His Glu Tyr Arg Leu Asp Asp Asn Thr Thr
    130                 135                 140
```

Thr His Asp Ser Asn Gly Ser Asn Pro Ile Gly Asp Ser Val Thr Glu
145                 150                 155                 160

Asp Gly Trp Val Val Cys Arg Val Phe Arg Lys Lys Asn Tyr Leu Lys
                165                 170                 175

Thr Leu Glu Ser Pro Lys Ser Asn Ser Ser Thr Gly His Asp Leu
        180                 185                 190

Lys Thr His Met Leu Ser Ser Gly Gly Asn Asp Gly Val Leu Asp Gln
        195                 200                 205

Ile Leu His Tyr Met Gly Arg Thr Cys Lys Met Glu Ser Asp Ser Leu
        210                 215                 220

Asn Asn Ile Asn Asn Ile Pro Ile Pro Asp Asn Asn Pro Arg Met Leu
225                 230                 235                 240

Val Gly Asn Asn Gly Gly Ile Asn Asp Gly Phe His Asp His Glu Arg
                245                 250                 255

Phe Met His Leu Pro Arg Leu Glu Ser Pro Thr Leu Pro Ser Leu Cys
            260                 265                 270

Tyr Gln Ser Ile Glu Asp Met Leu Thr Glu Thr Glu His Arg Gly Gly
        275                 280                 285

Cys Cys Gly Gly Gly Asn Asn Glu Thr Lys Asn Gly Val Asn Asp
290                 295                 300

Trp Val Thr Leu Asp Gln Leu Val Ala Ser Gln Leu Ser Gly Gln Val
305                 310                 315                 320

Glu Thr Ser Lys Gln Leu Ser Cys Phe Ser Asp Pro Asn Ala Val Phe
                325                 330                 335

Ser Leu Cys His Asp Asp Gly Ile Gln Leu Ser His Leu Asn Leu Gln
            340                 345                 350

Arg Ser Asn Gln Ser Ser Gln Val Tyr Ser Asn Asn Asp Asn Asp Leu
        355                 360                 365

Trp Ser Leu Thr Lys Ser Ser Phe Ser Pro Phe Ser Ser Asp Pro Leu
370                 375                 380

Cys His Leu Ser Val
385

<210> SEQ ID NO 42
<211> LENGTH: 401
<212> TYPE: PRT
<213> ORGANISM: Pyrus malus

<400> SEQUENCE: 42

Met Ser Asp Asp His Met Ser Leu Ser Ile Asn Gly Gln Ser Gln Val
1               5                   10                  15

Pro Pro Gly Phe Arg Phe His Pro Thr Glu Glu Leu Leu His Tyr
            20                  25                  30

Tyr Leu Arg Lys Lys Val Ala Phe Glu Arg Ile Asp Leu Asp Val Ile
        35                  40                  45

Arg Glu Val Asp Leu Asn Lys Leu Glu Pro Trp Asp Ile Gln Glu Lys
50                  55                  60

Cys Lys Ile Gly Ser Thr Pro Gln Asn Asp Trp Tyr Phe Phe Ser His
65                  70                  75                  80

Lys Asp Lys Lys Tyr Pro Thr Gly Thr Arg Thr Asn Arg Ala Thr Thr
                85                  90                  95

Ala Gly Phe Trp Lys Ala Thr Gly Arg Asp Lys Ile Ile Tyr Ser Gly
            100                 105                 110

Phe Lys Arg Ile Gly Leu Arg Lys Thr Leu Val Phe Tyr Lys Gly Arg
        115                 120                 125

Ala Pro His Gly Gln Lys Ser Asp Trp Ile Met His Glu Tyr Arg Leu
            130                 135                 140

Glu Glu Ser Asn Ser Thr His Asp Thr Thr Val Ser Ser Ser Met Gly
145                 150                 155                 160

Glu Ser Met Thr Glu Glu Gly Trp Val Val Cys Arg Val Phe Lys Lys
                165                 170                 175

Lys Asn Tyr Gln Lys Ala Leu Glu Ser Pro Lys Ala Ser Phe Ser Met
            180                 185                 190

Asp Ser Ser Asn Asn Gln Ile His Gly Ser Arg Asn Asp Gly Val Leu
        195                 200                 205

Asp Gln Ile Leu Met Tyr Met Gly Arg Thr Cys Lys Leu Glu Asn His
210                 215                 220

Asp Glu Pro Leu Thr Met Asn Asn Ile Ser Glu Arg Phe Met His Leu
225                 230                 235                 240

Pro Arg Leu Glu Ser Pro Thr Leu Pro Asn Leu Pro Ala Phe Asp Gln
                245                 250                 255

Asp Arg Ser Phe Lys Ala Cys Tyr Gln Ala Ile Asp Met Phe Ile
            260                 265                 270

Glu Thr Glu Pro Pro Ser Thr Asn Gln Gln Ser Asn Gly Cys Asp Asn
            275                 280                 285

Asn Glu Leu Val Asp Asp His Glu Asp Pro Lys Arg Arg Val Asn Asp
290                 295                 300

Trp Val Thr Leu Asp Arg Leu Val Ala Ser Gln Leu Gly Gln Leu Asn
305                 310                 315                 320

Gly Gln Asp Gln Val Thr Pro Lys His Leu Ser Cys Phe Gly Asp Pro
                325                 330                 335

Asn Met Ala Phe Cys Ser Ser Pro Pro Arg Asn Asp His Asp His
            340                 345                 350

Asp Val Gln Leu Ser Tyr Pro Tyr Leu Arg Thr Ser Ser Ser Ser His
            355                 360                 365

His Gln Ser Asp Val Tyr Asn Asn Glu Asn Asp Leu Trp Asn Phe Thr
        370                 375                 380

Lys Ser Ser Ser Ser Pro Ser Ser Thr Asp Pro Leu Cys His Leu Ser
385                 390                 395                 400

Val

<210> SEQ ID NO 43
<211> LENGTH: 411
<212> TYPE: PRT
<213> ORGANISM: Hordeum vulgare

<400> SEQUENCE: 43

Met Ser Ile Ser Val Asn Gly Gln Ser Val Val Pro Pro Gly Phe Arg
1               5                   10                  15

Phe His Pro Thr Glu Glu Glu Leu Leu Thr Tyr Tyr Leu Ala Lys Lys
                20                  25                  30

Val Ala Ser Gln Arg Ile Asp Leu Asp Val Ile Pro Asp Val Asp Leu
            35                  40                  45

Asn Lys Leu Glu Pro Trp Asp Ile Gln Glu Cys Cys Arg Ile Gly Thr
        50                  55                  60

Gly Pro Gln Asn Asp Trp Tyr Leu Phe Ser His Lys Asp Lys Lys Tyr
65                  70                  75                  80

Pro Thr Gly Thr Arg Thr Asn Arg Ala Thr Thr Val Gly Phe Trp Lys
                85                  90                  95

```
Ala Thr Gly Arg Asp Lys Ala Ile Tyr Pro Ala Ala Gly Tyr Gly His
            100                 105                 110

Ile Gly Met Arg Lys Thr Leu Val Phe Tyr Gln Gly Arg Ala Pro His
            115                 120                 125

Gly His Lys Ser Asp Trp Ile Met His Glu Tyr Arg Leu Asp Asp Ala
        130                 135                 140

Thr Thr Pro Gly Asn Asn Pro Ala Asn Gln Ala Ile Gly Asn Ala Pro
145                 150                 155                 160

Tyr Tyr Pro Gly Ser Ser Ser Ile Arg Ser Leu Val Gly Asp Gln
                165                 170                 175

Ser Ser Ala Gln Glu Asp Gly Trp Val Ile Cys Arg Val Phe Lys Lys
            180                 185                 190

Lys Asn Ile Val Val Gln Gln Ala Asp Gln Asn Gly Gly Arg
            195                 200                 205

Arg Thr Ala Ser Asn Asn Leu Val Ala Ala Gly Ala Ile Glu Leu Ser
    210                 215                 220

Arg Ser Asn Cys Ser Ser Thr Val Thr Thr Ala Ser Asp His Ala Lys
225                 230                 235                 240

Ala Thr His Met Gln Gln His Tyr Tyr Ser Ala Ser Asp Asp Ala Leu
                245                 250                 255

Asp His Ile Leu Asn Gln Tyr Met His Gly Arg Ser Ser Thr Thr Thr
                260                 265                 270

Thr Ser Cys Lys Lys Glu Thr Asn Ala Thr Asn Pro Ser Ser Ser Ala
            275                 280                 285

Leu Asp His Leu Ile Asn Ser Glu Cys His Asn Val Ser Ser Thr Leu
    290                 295                 300

Tyr Glu Lys Leu Pro Pro Leu Glu His Val Val Pro Gly Glu Leu Leu
305                 310                 315                 320

Pro Pro Thr Glu Tyr Ser Gly Asp Trp Asp Ala Leu Asp Arg Leu Ala
                325                 330                 335

Ala Tyr Glu Leu Asn Gly Leu Ser Asp Ala Ala Ser Ala Lys Thr Thr
                340                 345                 350

Asn Gly Met Pro Phe Ile Val Asp Glu Leu Gly Gly Ala Thr Ala Tyr
            355                 360                 365

Ser Gly Gly Arg Leu His Val Ser Ser Ile Thr Gly Thr Gly Asp
    370                 375                 380

Gly Asp Leu Trp Ser Leu Gly Arg Ser Val Ser Ser Leu His Ala Asp
385                 390                 395                 400

Leu Thr Ile Asn Ser Phe Asn Ala Val Gly Cys
                405                 410

<210> SEQ ID NO 44
<211> LENGTH: 399
<212> TYPE: PRT
<213> ORGANISM: Arabidopsis thaliana

<400> SEQUENCE: 44

Met Ser Lys Ser Met Ser Ile Ser Val Asn Gly Gln Ser Gln Val Pro
1               5                   10                  15

Pro Gly Phe Arg Phe His Pro Thr Glu Glu Leu Leu Gln Tyr Tyr
            20                  25                  30

Leu Arg Lys Lys Val Asn Ser Ile Glu Ile Asp Leu Asp Val Ile Arg
        35                  40                  45

Asp Val Asp Leu Asn Lys Leu Glu Pro Trp Asp Ile Gln Glu Met Cys
```

```
            50                  55                  60
Lys Ile Gly Thr Thr Pro Gln Asn Asp Trp Tyr Phe Phe Ser His Lys
 65                  70                  75                  80

Asp Lys Lys Tyr Pro Thr Gly Thr Arg Thr Asn Arg Ala Thr Ala Ala
                 85                  90                  95

Gly Phe Trp Lys Ala Thr Gly Arg Asp Lys Ile Ile Tyr Ser Asn Gly
            100                 105                 110

Arg Arg Ile Gly Met Arg Lys Thr Leu Val Phe Tyr Lys Gly Arg Ala
        115                 120                 125

Pro His Gly Gln Lys Ser Asp Trp Ile Met His Glu Tyr Arg Leu Asp
    130                 135                 140

Asp Asn Ile Ile Ser Pro Glu Asp Val Thr Val His Glu Val Val Ser
145                 150                 155                 160

Ile Ile Gly Glu Ala Ser Gln Asp Glu Gly Trp Val Val Cys Arg Ile
                165                 170                 175

Phe Lys Lys Lys Asn Leu His Lys Thr Leu Asn Ser Pro Val Gly Gly
            180                 185                 190

Ala Ser Leu Ser Gly Gly Gly Asp Thr Pro Lys Thr Thr Ser Ser Gln
        195                 200                 205

Ile Phe Asn Glu Asp Thr Leu Asp Gln Phe Leu Glu Leu Met Gly Arg
    210                 215                 220

Ser Cys Lys Glu Glu Leu Asn Leu Asp Pro Phe Met Lys Leu Pro Asn
225                 230                 235                 240

Leu Glu Ser Pro Asn Ser Gln Ala Ile Asn Asn Cys His Val Ser Ser
                245                 250                 255

Pro Asp Thr Asn His Asn Ile His Val Ser Asn Val Val Asp Thr Ser
            260                 265                 270

Phe Val Thr Ser Trp Ala Ala Leu Asp Arg Leu Val Ala Ser Gln Leu
        275                 280                 285

Asn Gly Pro Thr Ser Tyr Ser Ile Thr Ala Val Asn Glu Ser His Val
    290                 295                 300

Gly His Asp His Leu Ala Leu Pro Ser Val Arg Ser Pro Tyr Pro Ser
305                 310                 315                 320

Leu Asn Arg Ser Ala Ser Tyr His Ala Gly Leu Thr Gln Glu Tyr Thr
                325                 330                 335

Pro Glu Met Glu Leu Trp Asn Thr Thr Thr Ser Ser Leu Ser Ser Ser
            340                 345                 350

Pro Gly Pro Phe Cys His Val Ser Asn Val Leu Leu Leu Val Cys Leu
        355                 360                 365

Leu Arg Leu Gln Leu Gln Phe Trp Pro Phe Gln Pro Trp Gln Arg Gln
    370                 375                 380

Val His Phe Asp Leu Ser Ser Pro Gln Met Gln Ile Ser Leu His
385                 390                 395

<210> SEQ ID NO 45
<211> LENGTH: 96
<212> TYPE: PRT
<213> ORGANISM: Artificial Sequence
<220> FEATURE:
<223> OTHER INFORMATION: Synthetic sequence

<400> SEQUENCE: 45

Cys Cys Gly Asp Arg Gly Pro Tyr Ala Arg Ala Met Val Arg Glu Cys
 1               5                  10                  15

His Phe Ser Gly Gly Asn His Asp Pro Leu Gly Val Trp Lys Leu His
```

```
            20                  25                  30
Cys Phe Gly Asp Phe Leu Arg Leu Ala Pro Arg Ile Arg Ser Arg Phe
        35                  40                  45

Asn Ala Ala Phe Val Glu Phe Ala Val Asn Ser Asp Gly Val His Gly
    50                  55                  60

Ala Gly Thr Asn Phe Leu Pro Ala Gln Pro Gly Gly Trp Leu Phe Pro
65                  70                  75                  80

Tyr Tyr Glu Ser Leu Tyr His Pro Gly Trp Lys Tyr Leu Gln Leu Leu
                85                  90                  95
```

<210> SEQ ID NO 46
<211> LENGTH: 456
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(52)
<223> OTHER INFORMATION: Xaa can be any naturally occurring amino acid
<220> FEATURE:
<221> NAME/KEY: misc_feature
<222> LOCATION: (142)..(143)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (273)..(273)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (443)..(443)
<223> OTHER INFORMATION: Xaa can be any naturally occurring amino acid

<400> SEQUENCE: 46

```
Met Lys Gln Pro Arg Ser Arg Gln Glu Pro Arg Arg Val Gly Asn Gly
1               5                   10                  15
```

-continued

```
Ala Met Val Val Thr Met Leu Leu Ser Leu Cys Val Leu Thr Tyr Ile
            20                  25                  30

Lys Ala Arg Tyr Cys Ser Thr Pro Phe Pro Lys Xaa Ala Gln Xaa Glu
        35                  40                  45

Xaa Glu Xaa Xaa Ser Ile Asp Glu Asp Tyr Asp Ser Ser Arg Tyr Lys
50                      55                  60

Ile Thr Gly Pro Ile Gly Glu Glu Phe Asp Pro Glu Arg Pro Thr
65                  70                  75                  80

Cys Tyr Asn Thr Ser Lys Arg Ser Glu Arg Cys Ala Ala Val Gly Asp
                85                  90                  95

Ile Arg Val Asp Gly Asn His Ser Thr Ile Tyr Ile Ser Pro Leu Asp
            100                 105                 110

Arg Glu Trp Arg Thr Lys Pro Tyr Ala Arg Arg His Asp Ala Val Ala
        115                 120                 125

Met Asp Asp Val Arg Glu Phe Thr Leu Lys Pro Phe Gly Xaa Xaa Thr
130                 135                 140

Ala Val Pro Pro Leu Cys Thr Arg Asn His Ser Val Pro Ala Phe Leu
145                 150                 155                 160

Phe Ser Xaa Gly Gly Phe Ala Gly Asn Leu Tyr His Asp Tyr Thr Asp
            165                 170                 175

Val Leu Val Pro Leu Phe Thr Ser Thr His Xaa Phe Gly Gly Glu Val
        180                 185                 190

Gln Phe Leu Leu Xaa Asp Ile Lys Pro Trp Trp Xaa Asp Lys Phe Thr
195                 200                 205

Pro Leu Phe Arg Gln Leu Ser Asn Tyr Asp Val Ile Asp Val Asp Asn
210                 215                 220

Asp Gln Glu Val His Cys Phe Pro Arg Ile Val Val Gly Ala Thr Phe
225                 230                 235                 240

His Xaa Ala Met Gly Ile Asp Pro Ser Arg Ser Pro Gly Gly Val Ser
            245                 250                 255

Val Ala Asp Phe Lys Arg Leu Leu Arg Arg Ala Phe Arg Leu Glu Arg
        260                 265                 270

Xaa Val Ala Ser Arg Thr Gly Ala Pro Arg Arg Gly Lys Pro Arg Leu
275                 280                 285

Leu Ile Ile Ser Arg Lys Ser Ser Arg Arg Phe Leu Asn Glu Arg Glu
290                 295                 300

Met Ala Arg Ala Ala Xaa Ala Gly Phe Asp Val Arg Ile Ala Glu
305                 310                 315                 320

Pro Asp Asn His Thr Asp Met Pro Asn Phe Ala Arg Leu Val Asn Ser
            325                 330                 335

Ala Asp Val Met Met Gly Val His Gly Ala Gly Leu Thr Asn Met Val
        340                 345                 350

Phe Leu Pro Ser Arg Ala Val Leu Ile Gln Val Val Pro Phe Gly Gly
355                 360                 365

Leu Glu Trp Leu Thr Arg Val Thr Phe Lys Asp Pro Ala Lys Asp Met
370                 375                 380

Asp Val Asn Tyr Met Glu Tyr Asn Val Ser Leu Glu Glu Ser Ser Leu
385                 390                 395                 400

Arg Asp Gln Tyr Pro Arg Asp His Phe Tyr Leu Lys Asp Pro Tyr Asp
            405                 410                 415

Val His Lys Lys Gly Trp Asp Ala Ile Lys Thr Val Tyr Leu Asp Lys
        420                 425                 430
```

-continued

```
Gln Asn Val Arg Leu Asp Leu Asp Arg Phe Xaa Pro Thr Leu Glu Lys
        435                 440                 445

Ala Arg Asp Leu Leu Pro Ser Pro
    450                 455
```

What is claimed is:

1. A method of increasing resistance to herbivory by corn rootworm in a plant, said method comprising:
   (a) introducing into a regenerable plant cell a recombinant DNA construct comprising a polynucleotide operably linked to at least one regulatory sequence, wherein the polynucleotide encodes a polypeptide having an amino acid sequence of at least 95% sequence identity when compared to SEQ ID NO:2; and wherein the at least one regulatory sequence is a root-specific promoter, and
   (b) regenerating a transgenic plant from the regenerable plant cell after step (a), wherein the transgenic plant comprises in its genome the recombinant DNA construct; and
   wherein the transgenic plant has increased resistance to corn rootworm when compared to a control plant not comprising the recombinant DNA construct.

2. The method of claim 1, further comprising:
   (d) obtaining a progeny plant derived from the transgenic plant, wherein said progeny plant comprises in its genome the recombinant DNA construct and exhibits increased resistance to herbivory by corn rootworm when compared to a control plant not comprising the recombinant DNA construct.

3. The method of claim 1, wherein said plant is a monocot.

4. The method of claim 3, wherein said monocot is maize.

* * * * *